(12) United States Patent
Misawa et al.

(10) Patent No.: US 11,453,632 B2
(45) Date of Patent: Sep. 27, 2022

(54) 1-PHENYL-2-PHENYLETHANE DERIVATIVE

(71) Applicant: KAO CORPORATION, Tokyo (JP)

(72) Inventors: Kensuke Misawa, Utsunomiya (JP);
Takayoshi Inoue, Koto-ku (JP);
Shotaro Tsunoda, Musashino (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 17/288,427

(22) PCT Filed: Oct. 23, 2019

(86) PCT No.: PCT/JP2019/041506
§ 371 (c)(1),
(2) Date: Apr. 23, 2021

(87) PCT Pub. No.: WO2020/085373
PCT Pub. Date: Apr. 30, 2020

(65) Prior Publication Data
US 2022/0009869 A1 Jan. 13, 2022

(30) Foreign Application Priority Data
Oct. 23, 2018 (JP) .............................. JP2018-199549

(51) Int. Cl.
C07C 39/16 (2006.01)
C07D 233/18 (2006.01)
C07D 249/08 (2006.01)
A61P 5/28 (2006.01)
C07C 39/12 (2006.01)
C07C 69/16 (2006.01)
C07C 233/18 (2006.01)
C07D 205/04 (2006.01)
C07D 231/12 (2006.01)
C07D 263/32 (2006.01)
C07D 271/06 (2006.01)

(52) U.S. Cl.
CPC ................ C07C 39/16 (2013.01); A61P 5/28 (2018.01); C07C 39/12 (2013.01); C07C 69/16 (2013.01); C07C 233/18 (2013.01); C07D 205/04 (2013.01); C07D 231/12 (2013.01); C07D 249/08 (2013.01); C07D 263/32 (2013.01); C07D 271/06 (2013.01)

(58) Field of Classification Search
CPC ...... C07C 39/16; C07C 233/18; C07D 249/08
See application file for complete search history.

(56) References Cited

U.S. PATENT DOCUMENTS 3,123,615 A 3/1964 Rorig
2019/0192476 A1 6/2019 Jung et al.

FOREIGN PATENT DOCUMENTS

WO WO 2010/030787 A1 3/2010
WO WO 2016/102472 A1 6/2016
WO WO 2018/049094 A1 3/2018

OTHER PUBLICATIONS

Benign Prostatic Hyperplasia (BPH) [online] retrieved from internet on Mar. 9, 2022; URL: https://www.hopkinsmedicine.org/health.*
Starovoytov, O.N., et al., "Effects of the Hydroxyl Group on Pheny Based Ligand/ERRγ Protein Binding", Chem. Res. Toxicol., Dec. 31, 2014, vol. 27, No. 8, pp. 1371-1379.
Farzaneh, S., et al., "Estrogen Receptor Ligands: A Review (2013-2015)", Sci. Pharm., Dec. 31, 2016,vol. 84, pp. 409-427.
Delfosse, V., et al., "Structural and Functional Profiling of Environmental Ligands for Estrogen Receptors", Environmental Health, vol. 122, No. 12, Dec. 31, 2014, pp. 1306-1313.
International Search Report dated Dec. 24, 2019 in PCT/JP2019/041506 filed on Oct. 23, 2019, 3 pages.
Raine-Fenning et al., "Skin Aging and Menopause", Am. J. Clin. Dermatol., 2003, vol. 4, No. 6, pp. 371-378.
Hall et al., "Estrogen and skin: The effects of estrogen, menopause, and hormone replacement therapy on the skin", J. Am. Acad. Dermatol., 2005, vol. 53, No. 4, pp. 555-568.
Rendall et al., "The Hot Flush Beliefs Scale: A tool for assessing thoughts and beliefs associated with the experience of menopausal hot flushes and night sweats", Maturitas, The European Menopause Journal, 2008, vol. 60, pp. 158-169.
Sator et al., "The influence of hormone replacement therapy on skin ageing: A pilot study", Maturitas, The European Menopause Journal, 2001, vol. 39, pp. 43-55.

(Continued)

Primary Examiner — Shawquia Jackson
(74) Attorney, Agent, or Firm — Oblon, McClelland, Maier & Neustadt, L.L.P.

(57) ABSTRACT

Provided is a novel compound having a selective activating effect on ERβ. The present invention provides a compound represented by the following formula (1) wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, a 1-trifluoromethyl-1-hydroxymethyl group, or a 1-methylpropyl group; $R^2$ to $R^5$ are the same or different and each represent a hydrogen atom or a fluorine atom; and $R^6$ represents a hydrogen atom or an alkanoyl group having 2 to 5 carbon atoms, or a salt thereof.

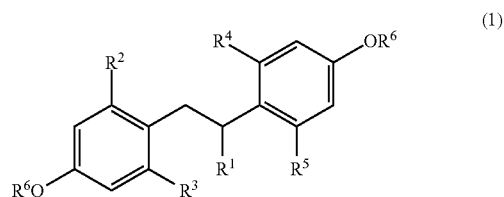

(1)

14 Claims, 7 Drawing Sheets

(56) References Cited

OTHER PUBLICATIONS

Pierard-Franchimont et al., "Skin water-holding capacity and transdermal estrogen therapy for menopause: a pilot study", Maturitas, Journal of the Climacteric & Postmenopause, 1995, vol. 22, pp. 151-154.

Pochi et al., "Endocrinologic Control of the Development and Activity of the Human Sebaceous Gland", The Journal of Investigative Dermatology, 1974, vol. 62, No. 3, pp. 191-201.

Van De Weijer et al., "Isoflavones from red clover (Promensil®) significantly reduce menopausal hot flush symptoms compared with placebo", Maturitas, The European Menopause Journal, 2002, vol. 42, pp. 187-193.

Mukherjee et al., "Orphan Nuclear Receptors as Targets for Drug Development", Pharm. Res., 2010, vol. 27, pp. 1439-1468.

Powell et al., "Intermolecular interactions identify ligand-selective activity of estrogen receptor $\alpha/\beta$ dimers", PNAS, 2008, vol. 105, No. 48, pp. 19012-19017.

Kulakosky et al., "Response element sequence modulates estrogen receptor $\alpha$ and $\beta$ affinity and activity", Journal of Molecular Endocrinology, 2002, vol. 29, pp. 137-152.

Rosenfeld et al., "Sensors and signals: a coactivator/corepressor/epigenetic code for integrating signal-dependent programs of transcriptional response", Genes & Development, 2006, vol. 20, pp. 1405-1428 (25 total pages).

Liu et al., "The genome landscape of ER$\alpha$- and ER$\beta$-binding DNA regions", PNAS, 2008, vol. 105, No. 7, pp. 2604-2609 (8 total pages).

Helguero et al., "Estrogen receptors alfa (ER$\alpha$) and beta (ER$\beta$) differentially regulate proliferation and apoptosis of the normal murine mammary epithelial cell line HC11", Oncogene, 2005, vol. 24, pp. 6605-6616.

Chang et al., "Estrogen Receptor $\beta$ Is a Novel Therapeutic Target for Photoaging", Molecular Pharmacology, 2010, vol. 77, pp. 744-750.

Meyers et al., "Estrogen Receptor-$\beta$ Potency-Selective Ligands: Structure-Activity Relationship Studies of Diarylpropionitriles and Their Acetylene and Polar Analogues", Journal of Medicinal Chemistry, 2001, vol. 44, No. 24, pp. 4230-4251.

McPherson et al., "Essential Role for Estrogen Receptor $\beta$ in Stromal-Epithelial Regulation of Prostatic Hyperplasia", Endocrinology, 2007, vol. 148, No. 2, pp. 566-574.

Masrudin et al., "Preventive effect of *Pueraria mirifica* on testosterone-induced prostatic hyperplasia in Sprague Dawley rats", Andrologia, 2015, vol. 47, pp. 1153-1159.

Waibel et al., "Bibenzyl- and stilbene-core compounds with non-polar linker atom substituents as selective ligands for estrogen receptor beta", European Journal of Medicinal Chemistry, 2009, vol. 44, No. 9, pp. 3412-3424.

Tuccinardi et al., "Receptor-based virtual screening evaluation for the identification of estrogen receptor $\beta$ ligands", Journal of Enzyme Inhibition and Medicinal Chemistry, 2015, vol. 30, No. 4, pp. 662-670.

\* cited by examiner

1-PHENYL-2-PHENYLETHANE DERIVATIVE

FIELD OF THE INVENTION

The present invention relates to a compound having high selectivity for estrogen receptor β.

BACKGROUND OF THE INVENTION

Estrogen, also called follicle hormone, regulates functions related to reproduction as female hormone in cooperation with progesterone which is corpus luteum hormone. Estrogen has been reported to have, in addition to such a function, an effect of acting on fibroblasts of the skin to promote the biosynthesis of collagen and hyaluronic acid, an effect of exhibiting an antagonistic effect against androgen to inhibit the hyperfunction of sebaceous glands activated by androgen, and an effect of reducing ultraviolet stress. Thus, the reduced ability to secrete estrogen promotes the progression of skin aging such as reduction in skin fitness or increase in wrinkles, or increases the frequency of occurrence of acne based on the excessive secretion of sebum or skin diseases such as skin roughness based on ultraviolet stress or reduced skin barrier functions.

For example, as women experience menopause, the functions of the whole skin are changed by marked decrease in estrogen concentration in blood. Particularly, in the dermis, the amount of collagen fibers is markedly decreased, resulting in conspicuous skin aging phenomena such as wrinkles or sag (Non Patent Literatures 1 and 2). Also, decreased estrogen concentrations in blood cause various symptoms of menopause disorder. Among them, hot flash is a typical symptom, which is the sudden feeling of warmth in the face or the body, causing elevated heart rates or heavy sweating (Non Patent Literature 3).

Meanwhile, it has been reported that: the hormone replacement therapy (HRT) of women after menopause ameliorates wrinkles and blood circulation; and the application of estrogen ameliorates wrinkles, elasticity, and moisture contents (Non Patent Literatures 4 and 5). It has also been reported that the application of estrogen inhibits the secretion of sebum from sebaceous glands (Non Patent Literature 6). Furthermore, it has been reported that symptoms of hot flash are markedly ameliorated by the ingestion of isoflavone, a phytoestrogen contained in soybeans or the like (Non Patent Literature 7). Estrogen is also known to be effective for preventing or ameliorating prostatic hyperplasia (Non Patent Literature 16). Estrogen is further considered to be effective for inhibiting the activation of androgen (Non Patent Literature 17).

Estrogen is known to exert its effects by binding to two types of estrogen receptors (hereinafter, referred to as ERα and ERβ) and working in cooperation therewith. Estrogen first binds to a ligand binding domain (LBD) of ERα or ERβ for conformational change, followed by the formation of dimers (three types of combinations, ERα/α, ERβ/β, and ERα/β) (Non Patent Literatures 8 and 9). The formed ER dimers are translocated into the nucleus where the dimers bind to estrogen response elements present on the genome, recruit various coupling factors there, and then control the transcriptional activity of a target gene (Non Patent Literatures 10 and 11).

Most of the target genes of ERα and ERβ are reportedly the same (Non Patent Literature 12). However, it has recently been suggested that ERα and ERβ have physiological functions different from each other due to combinations of some different target genes (Non Patent Literature 12). For example, these receptors have been reported to play opposite roles in such a way that ERα activates the proliferation of breast cancer cells, whereas ERβ inhibits this proliferation (Non Patent Literature 13). ERβ has also been reported to have a function of defending against the photoaging of the skin (Non Patent Literature 14).

Thus, ERβ is an idealistic molecule which can safely exert the effects of estrogen. If ERβ can be selectively activated, this may be useful for, for example, preventing or ameliorating skin aging symptoms ascribable to a decreased amount of estrogen, or menopause disorder such as hot flash, preventing or ameliorating prostatic hyperplasia, and inhibiting the activation of androgen.

1-Phenyl-2-phenylethane derivatives are synthesized as compounds having various substituents on a carbon chain and a phenyl ring, and have been reported to have pharmacological effects such as the activation of estrogen receptors and a protective effect against oxidative stress induced by ultraviolet ray (e.g., Patent Literature 1, Patent Literature 2, and Non Patent Literature 15). However, any compound having sufficiently high selectivity for ERP has not yet been found.

[Patent Literature 1] International Publication No. WO 2010/030787
[Patent Literature 2] International Publication No. WO 2016/102472
[Non Patent Literature 1] Nicholas et al., (2003) Am J Clin Dermatol 4: 371-378
[Non Patent Literature 2] Hall et al., (2005) J Am Acad Dermatol 53: 555-68
[Non Patent Literature 3] Rendall M J et al., (2008) Maturitas 60: 158-69
[Non Patent Literature 4] Sator et al., (2001) Maturitas 39: 43-55
[Non Patent Literature 5] PiCrard-Franchimon et al., (1995) Maturitas 22: 151-154
[Non Patent Literature 6] Peter et al., (1974) J Invest Dermatol 62: 191-201
[Non Patent Literature 7] Van de Weijer P H et al., (2002) Maturitas 42: 187-93
[Non Patent Literature 8] Mukherjee et al., (2010) Pharm Res 27: 1439-1468
[Non Patent Literature 9] Powell et al., (2008) Proc Natl Acad Sci USA 105: 19012-19017
[Non Patent Literature 10] Kulakosky et al., (2002) J Mol Endocrinol 29: 137-152
[Non Patent Literature 11] Michael et al., (2006) Genes Dev 2006 20: 1405-1428
[Non Patent Literature 12] Liu et al., (2008) Proc Natl Acad Sci USA 105: 2604-2609
[Non Patent Literature 13] Helguero et al., (2005) Oncogene 24: 6605-6616
[Non Patent Literature 14] Chang et al., (2010) Mol Pharmacol 77: 744-750
[Non Patent Literature 15] Meyers et al., (2001) J Med Chem 44: 4230-4251
[Non Patent Literature 16] Endocrinology. 2007 148: 566-74
[Non Patent Literature 17] Andrologia. 2015 47: 1153-9

DETAILED DESCRIPTION OF THE INVENTION

The present invention relates to the following 1) to 32).
1) A compound represented by the formula (1) given below or a salt thereof.

2) An ERβ activating agent comprising the compound represented by the formula (1) or the salt thereof according to 1) as an active ingredient.

3) A skin aging preventing or ameliorating agent comprising the compound represented by the formula (1) or the salt thereof according to 1) as an active ingredient.

4) A sebum secretion inhibiting agent comprising the compound represented by the formula (1) or the salt thereof according to 1) as an active ingredient.

5) An acne preventing or ameliorating agent comprising the compound represented by the formula (1) or the salt thereof according to 1) as an active ingredient.

6) A hot flash preventing or ameliorating agent comprising the compound represented by the formula (1) or the salt thereof according to 1) as an active ingredient.

7) A prostatic hyperplasia preventing or ameliorating agent comprising the compound represented by the formula (1) or the salt thereof according to 1) as an active ingredient.

8) An androgen activation inhibiting agent comprising the compound represented by the formula (1) or the salt thereof according to 1) as an active ingredient.

9) Use of the compound represented by the formula (1) or the salt thereof according to 1) for producing a skin aging preventing or ameliorating agent.

10) Use of the compound represented by the formula (1) or the salt thereof according to 1) for producing a sebum secretion inhibiting agent.

11) Use of the compound represented by the formula (1) or the salt thereof according to 1) for producing an acne preventing or ameliorating agent.

12) Use of the compound represented by the formula (1) or the salt thereof according to 1) for producing a hot flash preventing or ameliorating agent.

13) Use of the compound represented by the formula (1) or the salt thereof according to 1) for producing a prostatic hyperplasia preventing or ameliorating agent.

14) Use of the compound represented by the formula (1) or the salt thereof according to 1) for producing an androgen activation inhibiting agent.

15) The compound represented by the formula (1) or the salt thereof according to 1) for use in the prevention or amelioration of skin aging.

16) The compound represented by the formula (1) or the salt thereof according to 1) for use in the inhibition of sebum secretion.

17) The compound represented by the formula (1) or the salt thereof according to 1) for use in the prevention or amelioration of acne.

18) The compound represented by the formula (1) or the salt thereof according to 1) for use in the prevention or amelioration of hot flash.

19) The compound represented by the formula (1) or the salt thereof according to 1) for use in the prevention or amelioration of prostatic hyperplasia.

20) The compound represented by the formula (1) or the salt thereof according to 1) for use in the inhibition of androgen activation.

21) Non-therapeutic use of the compound represented by the formula (1) or the salt thereof according to 1) for preventing or ameliorating skin aging.

22) Non-therapeutic use of the compound represented by the formula (1) or the salt thereof according to 1) for inhibiting sebum secretion.

23) Non-therapeutic use of the compound represented by the formula (1) or the salt thereof according to 1) for preventing or ameliorating acne.

24) Non-therapeutic use of the compound represented by the formula (1) or the salt thereof according to 1) for preventing or ameliorating hot flash.

25) Non-therapeutic use of the compound represented by the formula (1) or the salt thereof according to 1) for preventing or ameliorating prostatic hyperplasia.

26) Non-therapeutic use of the compound represented by the formula (1) or the salt thereof according to 1) for inhibiting androgen activation.

27) A method for preventing or ameliorating skin aging, comprising administering or ingesting the compound represented by the formula (1) or the salt thereof according to 1) in an effective amount to a subject in need thereof.

28) A method for inhibiting sebum secretion, comprising administering or ingesting the compound represented by the formula (1) or the salt thereof according to 1) in an effective amount to a subject in need thereof.

29) A method for preventing or ameliorating acne, comprising administering or ingesting the compound represented by the formula (1) or the salt thereof according to 1) in an effective amount to a subject in need thereof.

30) A method for preventing or ameliorating hot flash, comprising administering or ingesting the compound represented by the formula (1) or the salt thereof according to 1) in an effective amount to a subject in need thereof.

31) A method for preventing or ameliorating prostatic hyperplasia, comprising administering or ingesting the compound represented by the formula (1) or the salt thereof according to 1) in an effective amount to a subject in need thereof.

32) A method for inhibiting androgen activation, comprising administering or ingesting the compound represented by the formula (1) or the salt thereof according to 1) in an effective amount to a subject in need thereof.

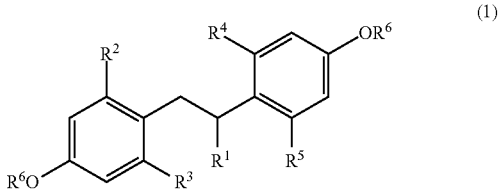

(1)

wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered saturated cyclic amino group, an alkanoylamino group having 2 to 6 carbon atoms and optionally substituted with a halogen atom, a 1-trifluoromethyl-1-hydroxymethyl group, or a 1-methylpropyl group; $R^2$ to $R^5$ are the same or different and each represent a hydrogen atom or a fluorine atom; and $R^6$ represents a hydrogen atom or an alkanoyl group having 2 to 5 carbon atoms.

BRIEF DESCRIPTION OF THE DRAWINGS

FIG. 5-1 shows the skin temperature elevation inhibitory effect of the compound of the present invention (3 and 5 days after administration). Left diagrams: raw value of skin temperature, right diagrams: changed temperature from initial value (skin temperature on measurement date–initial value)

FIG. 5-2 shows the skin temperature elevation inhibitory effect of the compound of the present invention (7, 14, and 21 days after administration). Left diagrams: raw value of skin temperature, right diagrams: changed temperature from initial value (skin temperature on measurement date–initial value)

DETAILED DESCRIPTION OF THE INVENTION

Figure 1:
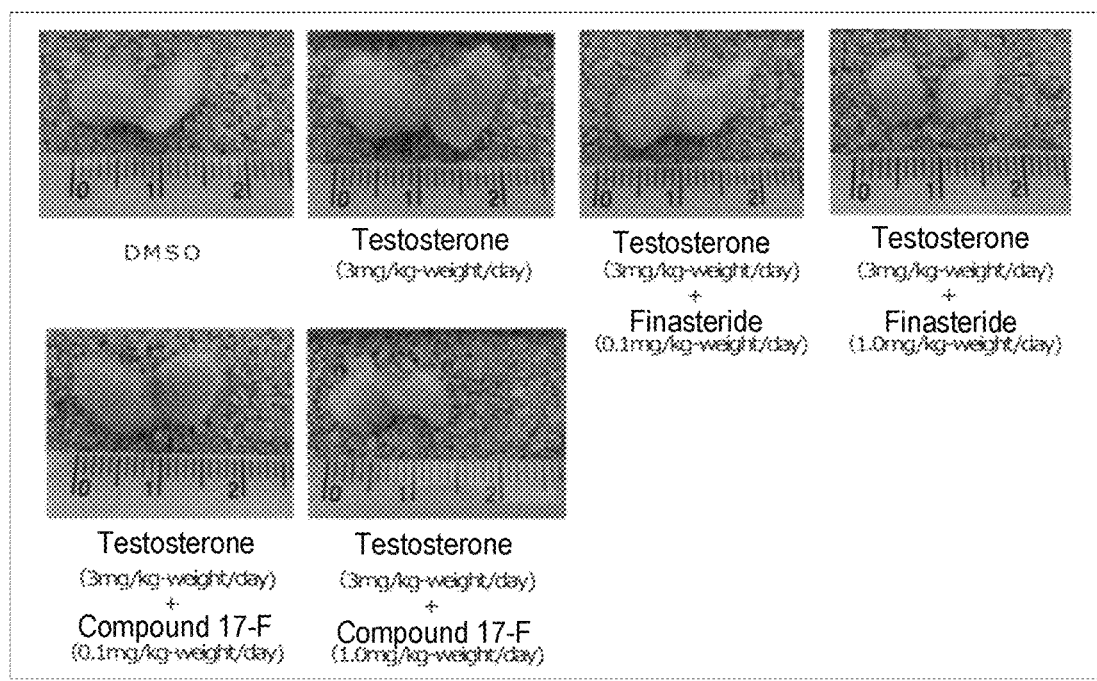
FIG. 1 shows the prostatic hyperplasia inhibitory effect of the compound of the present invention (the size of the prostate).

The present invention relates to providing a novel compound having a selective activating effect on ERβ, and use of the compound as an ERβ activating agent.

The present inventors conducted studies on substances enhancing the activity of ERβ among estrogen receptors, and consequently found that a specific 1-phenyl-2-phenylethane derivative has high selectivity for ERP and is useful as an ERP activating agent.

The compound of the present invention or a salt thereof selectively activates ERP and is safe with a low risk of developing or aggravating breast cancer, and as such, is useful as a medicament or a quasi drug capable of exerting effects such as the prevention or amelioration of aging symptoms of the skin, the inhibition of sebum secretion from sebaceous glands, the prevention or amelioration of acne, the prevention or amelioration of menopause disorder such as hot flash, the prevention or amelioration of prostatic hyperplasia, and the inhibition of androgen activation, or as a material or a preparation to be blended thereinto.

In the present specification, the term "non-therapeutic" conceptually excludes medical practice, i.e., therapeutic treatment practice on human bodies.

In the present specification, the term "amelioration" refers to change for the better in a disease, a symptom or a condition, the prevention or delay of aggravation of a disease, a symptom or a condition, or the changeover, prevention or delay of progression of a disease or a symptom.

In the present specification, the term "prevention" refers to the prevention or delay of development of a disease or a symptom in an individual, or reduction in the risk of developing a disease or a symptom in an individual.

In the present specification, the term "optionally substituted" means that a hydrogen atom of an intended group may be replaced with another group. The number of the substituent can be one or more. When two or more substituents are present, the substituents may be the same or different.

Hereinafter, symbols used in a compound represented by the formula (1) (also referred to as the "compound of the present invention") will be described.

Preferred examples of the "cycloalkyl group having 3 to 8 carbon atoms" represented by $R^1$ include a cyclopropyl group, a cyclobutyl group, a cyclopentyl group, and a cyclohexyl group. Among them, a cycloalkyl group having 3 or 4 carbon atoms is more preferred, and a cyclopropyl group is even more preferred.

The alkenyl group in the "alkenyl group having 2 to 6 carbon atoms and optionally substituted with a halogen atom" represented by $R^1$ can be linear or branched and is preferably an alkenyl group having 2 to 4 carbon atoms. Examples thereof include an ethenyl group, a 1-propenyl group, a 2-propenyl group, a 1-methylethenyl group, a 2-methyl-1-propenyl group, a 1-methyl-1-propenyl group, a 1-methyl-2-propenyl group, and a 3-butenyl group, and preferably include an ethenyl group and a 1-propenyl group. An ethenyl group is more preferred.

The halogen atom that may be used to substitute the alkenyl group is a fluorine atom, a chlorine atom, a bromine atom or an iodine atom and is preferably a fluorine atom or a chlorine atom, more preferably a fluorine atom.

Examples of the "alkenyl group having 2 to 6 carbon atoms and optionally substituted with a halogen atom" preferably include an alkenyl group having 2 to 4 carbon atoms and optionally monosubstituted or disubstituted with a fluorine atom or a chlorine atom, and more preferably include an ethenyl group monosubstituted or disubstituted with a fluorine atom or a chlorine atom, and a 1-propenyl group. The alkenyl group having 2 to 6 carbon atoms and optionally substituted with a halogen atom is more preferably an ethenyl group monosubstituted or disubstituted with a fluorine atom or a chlorine atom, even more preferably a 2,2-difluoroethenyl group, a 2,2-dichloroethenyl group, a 2-fluoroethenyl group, or a 2-chloroethenyl group, even more preferably a 2,2-difluoroethenyl group.

Examples of the "5-membered nitrogen-containing heteroaryl group" represented by $R^1$ preferably include a 5-membered heteroaryl group containing at least 1 to 3 nitrogen atoms and optionally further containing an oxygen atom. Specific examples thereof include an imidazolyl group, a pyrazolyl group, an oxazolyl group, an isoxazolyl group, a thiazolyl group, an isothiazolyl group, a triazolyl group, a tetrazolyl group, an oxadiazolyl group, a thiadiazolyl group, and a tetrazolyl group. The 5-membered nitrogen-containing heteroaryl group is more preferably a pyrazolyl group, an oxazolyl group, a triazolyl group, or an oxadiazolyl group.

Examples of the "4- to 6-membered saturated cyclic amino group" represented by $R^1$ include an azetidino group, a piperidino group, a morpholino group, a pyrrolizino group, and piperazino group, and preferably include an azetidino group.

Examples of the alkanoylamino group in the "alkanoylamino group having 2 to 5 carbon atoms and optionally substituted with a halogen atom" represented by $R^1$ can include an amino group substituted by a linear or branched alkanoyl group having 1 to 4 carbon atoms (preferably having 1 to 3 carbon atoms), and specifically include an acetylamino group, a propionylamino group, and a butyrylamino group. An acetylamino group is preferred.

The halogen atom that may be used to substitute the alkanoylamino group is preferably a chlorine atom or a fluorine atom, more preferably a fluorine atom.

The halogen atom-substituted alkanoylamino group having 2 to 5 carbon atoms is preferably a group in which one to three hydrogen atoms of an alkanoyl moiety are replaced with halogen atoms. Examples thereof include a trifluoroacetylamino group.

$R^2$ to $R^5$ are the same or different and each represent a hydrogen atom or a fluorine atom. Any one or two thereof is preferably a fluorine atom. Preferably, each of $R^2$ and $R^3$ is a fluorine atom and each of $R^4$ and $R^5$ is a hydrogen atom, or each of $R^2$ and $R^4$ is a fluorine atom and each of $R^3$ and $R^5$ is a hydrogen atom (or each of $R^2$ and $R^4$ is a hydrogen atom and each of $R^3$ and $R^5$ is a fluorine atom), from the viewpoint of ERβ selectivity.

Examples of the alkanoyl group having 2 to 5 carbon atoms represented by $R^6$ include an acetyl group, a benzoyl group, a propionyl group, a butyryl group, and an isobutyryl group. An acetyl group is preferred.

Examples of the compound of the present invention preferably include a compound in which $R^1$ is a cycloalkyl group having 3 to 8 carbon atoms, or an alkenyl group having 2 to 6 carbon atoms and optionally substituted with a halogen atom; each of $R^2$ and $R^3$ is a fluorine atom and each of $R^4$ and $R^5$ is a hydrogen atom, or each of $R^2$ and $R^4$ is a fluorine atom and each of $R^3$ and $R^5$ is a hydrogen atom (or each of $R^2$ and $R^4$ is a hydrogen atom and each of $R^3$ and $R^5$ is a fluorine atom); and $R^h$ is a hydrogen atom, from the viewpoint of ERP selectivity. Among them, $R^1$ is more preferably an alkenyl group having 2 to 6 carbon atoms and optionally substituted with a halogen atom, even more preferably an alkenyl group having 2 to 4 carbon atoms and optionally monosubstituted or disubstituted with a fluorine atom or a chlorine atom, even more preferably an ethenyl group monosubstituted or disubstituted with a fluorine atom or a chlorine atom (i.e., the formula (1A) or (1B) given below), even more preferably a 2,2-difluoroethenyl group, a 2,2-dichloroethenyl group, a 2-fluoroethenyl group, or a 2-chloroethenyl group, even more preferably a 2,2-difluoroethenyl group or a 2,2-dichloroethenyl group.

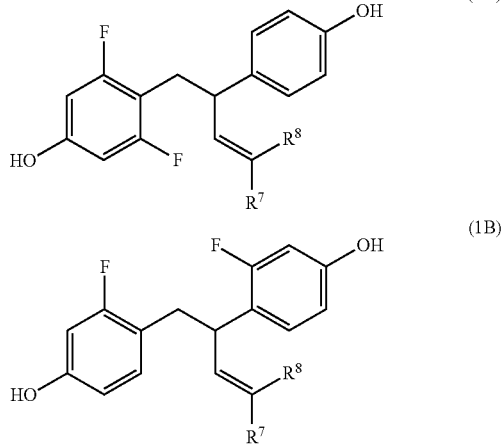

wherein $R^7$ represents a hydrogen atom, a fluorine atom or a chlorine atom, and $R^8$ represents a fluorine atom or a chlorine atom.

The salt of the compound of the present invention is preferably a pharmacologically acceptable salt. Examples thereof include: salts of inorganic bases, such as metal salts including alkali metal salts (e.g., sodium salt and potassium salt) and alkaline earth metal salts (e.g., calcium salt and magnesium salt), ammonium salts, alkali metal carbonates (e.g., lithium carbonate, potassium carbonate, sodium carbonate, and cesium carbonate), alkali metal bicarbonates (e.g., lithium bicarbonate, sodium bicarbonate, and potassium bicarbonate), and alkali metal hydroxides (e.g., lithium hydroxide, sodium hydroxide, potassium hydroxide, and cesium hydroxide); salts of organic bases, such as tri(lower) alkylamines (e.g., trimethylamine, triethylamine, and N-ethyldiisopropylamine), pyridine, quinoline, piperidine, imidazole, picoline, dimethylaminopyridine, dimethylaniline, N-(lower) alkyl-morpholines (e.g., N-methylmorpholine), 1,5-diazabicyclo[4.3.0]nonene-5 (DBN), 1,8-diazabicyclo [5.4.0]undecene-7 (DBU), and 1,4-diazabicyclo[2.2.2]octane (DABCO); salts of inorganic acids, such as hydrochloride, hydrobromide, hydroiodide, sulfate, nitrate, and phosphate; and salts of organic acids, such as formic acid, acetate, propionate, oxalate, malonate, succinate, fumarate, maleate, lactate, malate, citrate, tartrate, carbonate, picrate, methanesulfonate, ethanesulfonate, p-toluenesulfonate, and glutamate.

The compound of the present invention or the salt thereof can not only be present in an unsolvated form but also as a hydrate or a solvate. Thus, the compound of the present invention or the salt thereof includes all crystal forms and hydrates or solvates thereof.

The compound of the present invention also encompasses isomers such as geometric isomers, stereoisomers, and optical isomers, as a matter of course.

The compound of the present invention or the salt thereof can be produced by methods shown in the following Synthesis Examples or Production Examples described later, and methods equivalent thereto.

Synthesis Example 1

A compound of the formula (1) wherein $R^6$ is a hydrogen atom, and a compound of the formula (1) wherein $R^6$ is an alkanoyl group having 2 to 5 carbon atoms can be produced by, for example, the following reaction steps.

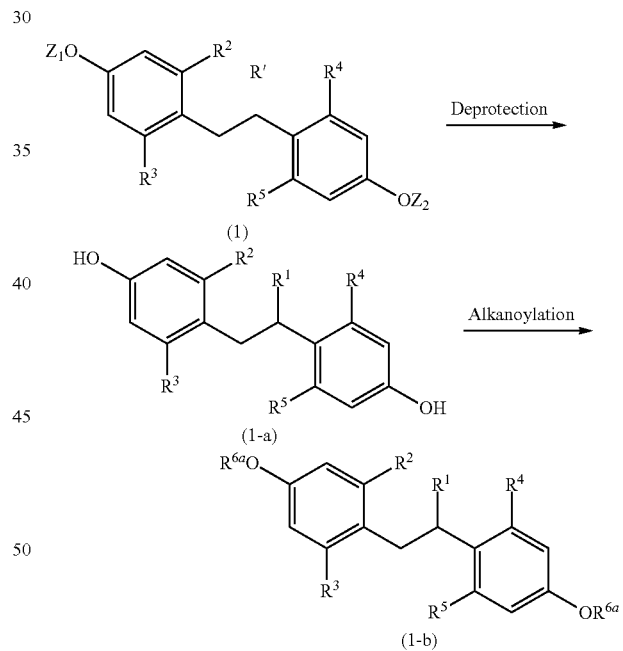

wherein $R^1$ to $R^5$ are as defined above; $R^{6a}$ represents an alkanoyl group having 2 to 5 carbon atoms; and $Z_1$ and $Z_2$ each represent a hydroxy protective group.

In this context, examples of the hydroxy protective group represented by $Z_1$ and $Z_2$ include alkyl groups (a methyl group, an ethyl group, a t-butyl group, etc.), aralkyl groups (a triphenylmethyl group, a benzyl group), trialkylsilyl groups (a t-butyldimethylsilyl group, a triisopropylsilyl group, etc.), and alkyldiarylsilyl groups (t-butyldiphenylsilyl, etc.).

The compound (1-a) of the present invention wherein $R^6$ is a hydrogen atom can be obtained by subjecting compound (I) to deprotection reaction.

This reaction is usually performed in a solution.

The solvent is not particularly limited as long as the solvent does not influence the reaction. Examples of the solvent that can be used include: halogenated hydrocarbons such as dichloromethane and dichloroethane; alcohols such as methanol and ethanol; ethers such as tetrahydrofuran, diethyl ether, dioxane, t-butyl methyl ether, and diglyme; and others such as ethyl acetate, dimethylformamide, and dimethyl sulfoxide. The reagent used is not particularly limited. Examples of the reagent that can be used include: Lewis acids such as boron trifluoride-dimethyl sulfide; protonic acids such as trifluoroacetic acid; bases such as sodium hydroxide; hydrogen gas; and fluoride ion source agents such as hydrogen fluoride and tetrabutylammonium fluoride. If necessary, a catalyst such as palladium carbon may be added. The reaction temperature is not particularly limited and is preferably, particularly, in a range from 0° C. to the reflux temperature of the solvent used.

The compound (1-b) of the present invention wherein $R^6$ is an alkanoyl group having 2 to 5 carbon atoms can be obtained by alkanoylating compound (1-a).

This reaction is usually performed in a solution. The reaction solvent is not particularly limited. For example, a base such as pyridine or triethylamine, a halogenated hydrocarbon such as dichloromethane or dichloroethane, or a mixture of two or more thereof can be used. The alkanoylating agent is not particularly limited. For example, an acid chloride represented by $R^6$—C(=O)X ($R^a$ is as defined above, and X represents a halogen atom), or an acid anhydride represented by $R^{6a}$—C(=O)OC(=O)—$R^{6a}$ can be used. If necessary, a catalyst such as 4-dimethylaminopyridine may be added. The reaction temperature is not particularly limited and is preferably, particularly, in a range from 0° C. to the reflux temperature of the solvent used.

Synthesis Example 2

A compound of the formula (1) wherein $R^1$ is a cycloalkyl group having 3 to 8 carbon atoms can be produced by, for example, the following reaction steps and a method equivalent thereto.

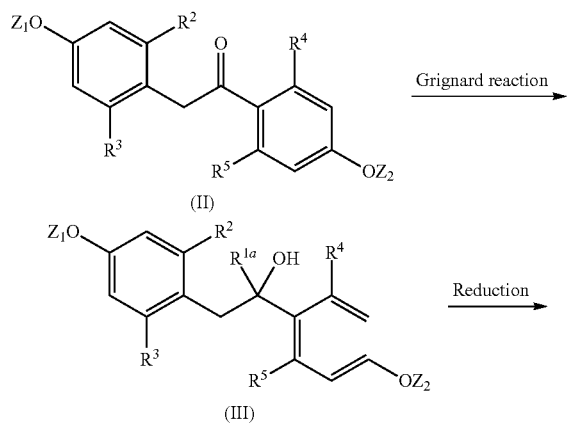

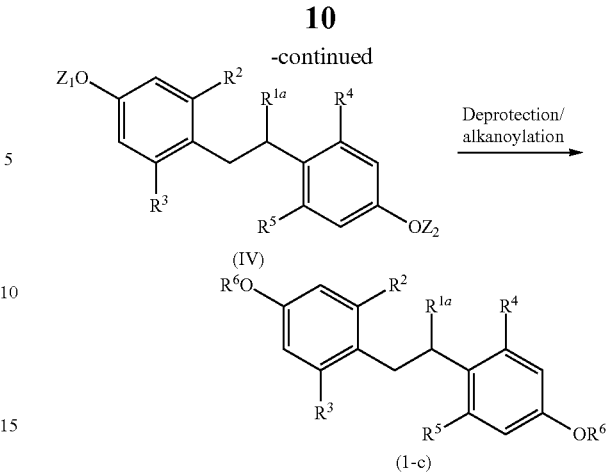

wherein $R^{1a}$ represents a cycloalkyl group having 3 to 8 carbon atoms, and $R^2$ to $R^6$, $Z_1$ and $Z_2$ are as defined above.

Compound (II) is subjected to Grignard reaction in a solvent to obtain compound (III).

This reaction is usually performed in a solution. The solvent is not particularly limited as long as the solvent does not influence the reaction. Examples of the solvent that can be used include: ethers such as tetrahydrofuran, diethyl ether, dioxane, t-butyl methyl ether, and diglyme; hydrocarbons such as hexane and toluene; and mixtures of two or more thereof. The Grignard reagent used can be a reagent represented by $R^{1a}$—MgX ($R^{1a}$ is as defined above, and X represents a halogen atom). The reaction temperature is not particularly limited and is preferably, particularly, in a range from 0° C. to the reflux temperature of the solvent used.

Compound (III) is subjected to reduction reaction in a solvent to obtain compound (IV).

This reaction is usually performed in a solution. The solvent is not particularly limited as long as the solvent does not influence the reaction. Examples of the solvent that can be used include halogenated hydrocarbons such as dichloromethane and dichloroethane. The reduction reagent used is not particularly limited. For example, a silane reduction reagent such as $R_3SiH$ (R represents an alkyl group, an aromatic group, an alkylsilyl group, or the like) can be used. The acid used is not particularly limited. For example, a Lewis acid such as $BF_3 \cdot OEt_2$ or $AlCl_3$ or a protonic acid such as trifluoroacetic acid can be used. The reaction temperature is not particularly limited and is preferably, particularly, in a range from −78° C. to room temperature.

Compound (IV) is deprotected as shown in Synthesis Example 1 and, if necessary, alkanoylated to obtain the compound (1-c) of the present invention.

Synthesis Example 3

A compound of the formula (1) wherein $R^1$ is a halogen atom-substituted alkenyl group having 2 to 6 carbon atoms (e.g., an ethenyl group) can be produced by, for example, the following reaction steps and a method equivalent thereto.

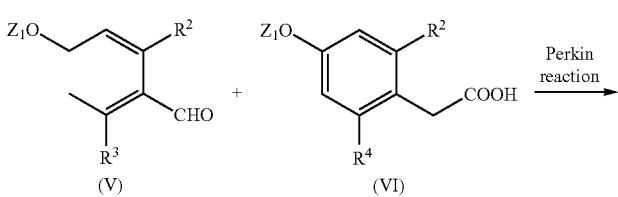
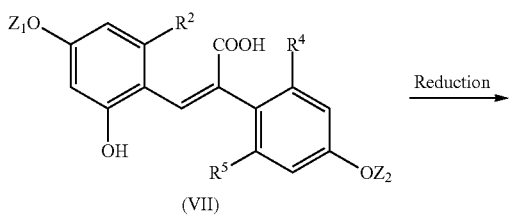

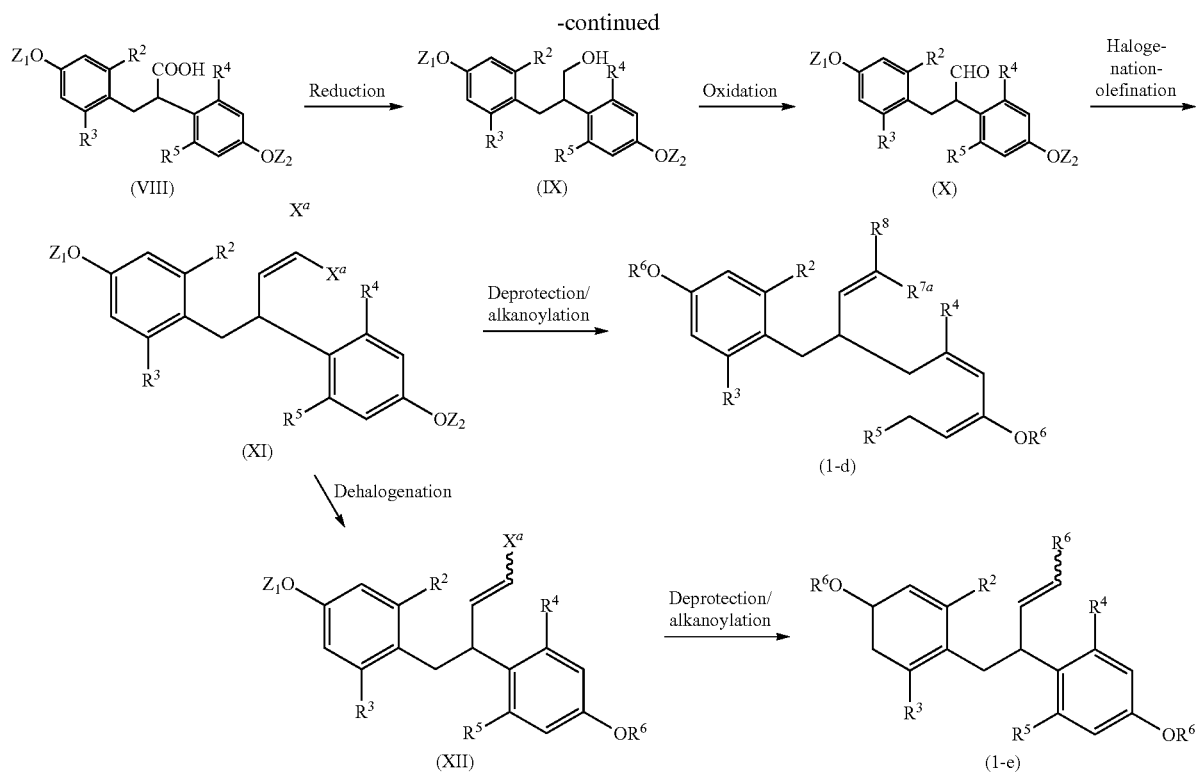

wherein $R^2$ to $R^6$, $R^8$, $Z_1$ and $Z_2$ are as defined above; $X^a$ represents a fluorine atom or a chlorine atom; and $R^{7a}$ represents a fluorine atom or a chlorine atom.

Compound (V) and compound (VI) are subjected to Perkin reaction to obtain compound (VII).

This reaction is usually performed in a solution. The solvent is not particularly limited as long as the solvent does not influence the reaction. Examples of the solvent that can be used include acid anhydrides and acid chlorides, such as acetic anhydride and acetyl chloride. The base is not particularly limited as long as the base does not influence the reaction. For example, triethylamine or pyridine can be used. The reaction temperature is not particularly limited and is preferably, particularly, in a range from 0° C. to the reflux temperature of the solvent used.

Compound (VII) is subjected to the reduction reaction of an olefin in a solvent to obtain compound (VIII).

This reaction is usually performed in a solution. The solvent is not particularly limited as long as the solvent does not influence the reaction. Examples of the solvent that can be used include: alcohols such as ethanol and methanol; others such as ethyl acetate and dimethylformamide; and mixtures of two or more thereof. The catalyst used is not particularly limited as long as the catalyst does not influence the reaction. For example, palladium carbon can be used. The reducing agent is not particularly limited. For example, hydrogen gas can be used. The reaction temperature is not particularly limited and is preferably, particularly, in a range from 0° C. to the reflux temperature of the solvent used.

Compound (VIII) is subjected to the reduction reaction of a carboxylic acid in a solvent to obtain compound (IX).

This reaction is usually performed in a solution. The solvent is not particularly limited as long as the solvent does not influence the reaction. Examples of the solvent that can be used include ethers such as tetrahydrofuran, diethyl ether, dioxane, t-butyl methyl ether, and diglyme. The reducing agent used is not particularly limited. For example, boranes, lithium aluminum hydride, or lithium borohydride can be used. The reaction temperature is not particularly limited and is preferably, particularly, in a range from −78° C. to the reflux temperature of the solvent used.

Compound (IX) is subjected to the oxidation reaction of an alcohol in a solvent to obtain compound (X).

This reaction is usually performed in a solution. The solvent is not particularly limited as long as the solvent does not influence the reaction. Examples of the solvent that can be used include halogenated hydrocarbons such as dichloromethane and chloroform. The oxidizing agent is not particularly limited. For example, the approach used employs a Dess-Martin reagent, a hypervalent iodine compound such as 2-iodoxybenzoic acid (IBX), a chromate such as pyridinium chlorochromate (PCC) or pyridinium dichromate (PDC), or dimethyl sulfoxide (DMSO) for Swern oxidation, etc. If necessary, a catalyst such as water may be added. The reaction temperature is not particularly limited and is preferably, particularly, in a range from −78° C. to the reflux temperature of the solvent used.

Compound (X) is subjected to gem-dihalogeno-olefination reaction in a solvent to obtain compound (XI).

This reaction is usually performed in a solution. The solvent is not particularly limited as long as the solvent does not influence the reaction. Examples of the solvent that can be used include: ethers such as tetrahydrofuran, diethyl ether, dioxane, t-butyl methyl ether, and diglyme; and others such as dimethylformamide, dimethyl sulfoxide, and N-methylpyrrolidone. The dihalogeno-olefinating agent is not particularly limited. For example, a Horner-Wadsworth-Emmons reagent such as $HCX_2P(O)(OEt)_2$ (X represents a fluorine atom or a chlorine atom) or a Wittig reagent based on $PR^a_3$ ($R^a$ represents an alkyl group or an aryl group) and $CF_2X^a{}_2$ or $MO_2CCF_2X^a$ ($X^a$ represents a fluorine atom or a chlorine atom, and M represents an alkali metal) can be used. If necessary, a base such as lithium diisopropylamide (hereinafter, abbreviated to LDA), t-butoxy potassium (hereinafter, referred to as t-BuOK), or n-butyllithium (hereinafter, referred to as n-BuLi) may be used. The reaction temperature is not particularly limited and is preferably, particularly, in a range from −78° C. to the reflux temperature of the solvent used.

Compound (XI) can be dehalogenated to obtain compound (XII) wherein $R^1$ is a halogen-monosubstituted alkenyl group.

This reaction is usually performed in a solution. The solvent is not particularly limited as long as the solvent does not influence the reaction. Examples of the solvent that can be used include: ethers such as tetrahydrofuran, diethyl ether, dioxane, t-butyl methyl ether, and diglyme; and aromatic hydrocarbons such as benzene and toluene. The reducing agent is not particularly limited. For example, sodium bis(2-methoxyethoxy)aluminum hydride (Red-Al®), lithium aluminum hydride (hereinafter, referred to as LAH), or lithium triethylborohydride can be used. The reaction temperature is not particularly limited and is preferably, particularly, in a range from −78° C. to the reflux temperature of the solvent used.

Compound (XI) or (XII) is deprotected as shown in Synthesis Example 1 and, if necessary, alkanoylated to obtain the compound (1-d) or (1-e) of the present invention.

Synthesis Example 4

A compound of the formula (1) wherein $R^1$ is an alkenyl group having 2 to 6 carbon atoms (e.g., a 1-propenyl group) can be produced by, for example, the following reaction steps and a method equivalent thereto.

Compound (XII) is olefinated to obtain compound (XIII).

This reaction is usually performed in a solution. The solvent is not particularly limited as long as the solvent does not influence the reaction. Examples of the solvent that can be used include: ethers such as tetrahydrofuran, diethyl ether, dioxane, t-butyl methyl ether, and diglyme; and others such as dimethylformamide, dimethyl sulfoxide, and N-methylpyrroiidone. The olefinating agent is not particularly limited. For example, $CrCl_2$ and $CH_3CHX_2$ (X represents a bromine atom or an iodine atom), or a Horner-Wadsworth-Emmons reagent such as $H_2C(Me)P(O)(OEt)_2$, or a Wittig reagent based on $PR^a{}_3$ ($R^a$ represents an alkyl group or an aryl group) and $CH(Me)X_2$ (X represents a chlorine atom, a bromine atom, or an iodine atom) can be used. If necessary, for example, a base such as LDA, t-BuOK, or n-BuLi can be used. The reaction temperature is not particularly limited and is preferably, particularly, in a range from −78° C. to the reflux temperature of the solvent used.

Compound (XIII) is deprotected as shown in Synthesis Example 1 and, if necessary, alkanoylated to obtain the compound (1-f) of the present invention.

Hereinafter, other Synthesis Examples will be shown as to compound (1-g) of the formula (1) wherein $R^1$ is a 1-methylpropyl group, compound (1-h) of the formula (1) wherein $R^1$ is a 1-trifluoromethyl-1-hydroxymethyl group, compound (1-i) of the formula (1) wherein $R^1$ is an alkanoylamino group having 2 to 6 carbon atoms and optionally substituted with a halogen atom, compound (1-j) of the formula (1) wherein $R^1$ is a 4- to 6-membered saturated cyclic amino group, and compound (1-k, 1-l, 1-m, 1-n, 1-o, 1-p, or 1-q) of the formula (1) wherein $R^1$ is a 5- or 6-membered nitrogen-containing heteroaryl group. Specifically, these compounds can be produced by methods described in corresponding Production Examples and methods equivalent thereto.

<Synthesis Example 5>: Production Example of Compound Wherein $R^1$ is 1-Methylpropyl Group (See Production Example 3)

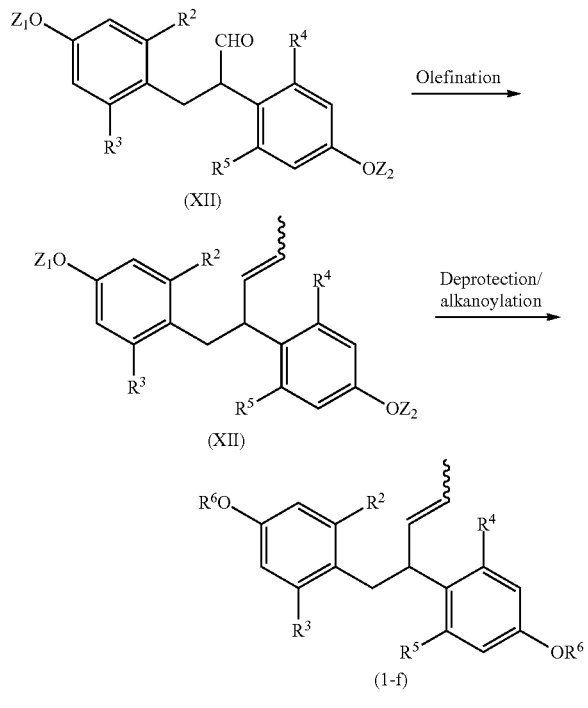

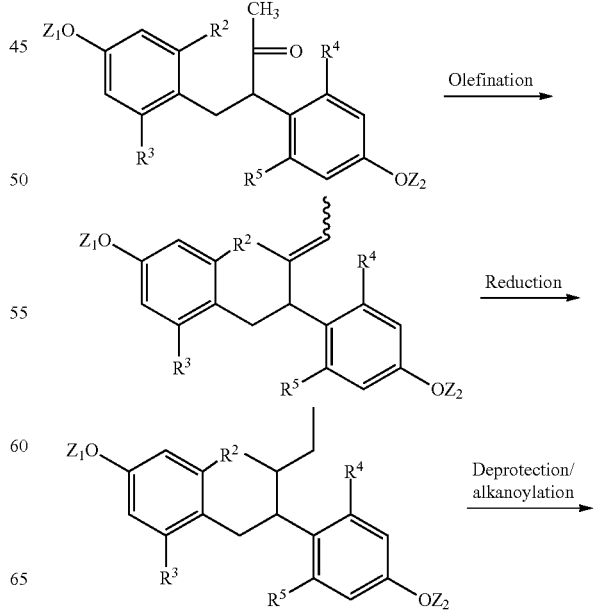

wherein $R^2$ to $R^6$, $Z_1$ and $Z_2$ are as defined above.

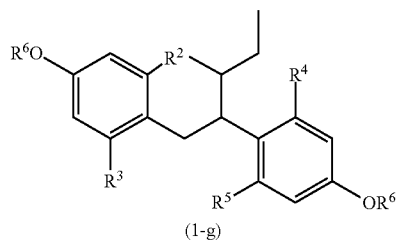

(1-g)

wherein $R^2$ to $R^6$, $Z_1$ and $Z_2$ are as defined above.

<Synthesis Example 6>: Production Example of Compound Wherein $R^1$ is 1-Trifluoromethyl-1-Hydroxymethyl Group (See Production Example 6)

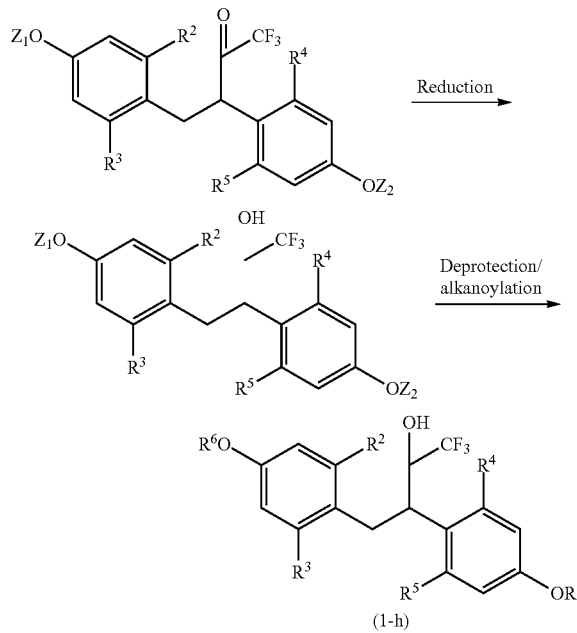

(1-h)

wherein $R^2$ to $R^6$, $Z_1$ and $Z_2$ are as defined above.

<Synthesis Example 7>: Production Example of Compound Wherein $R^1$ is an Alkanoylamino Group Having 2 to 6 Carbon Atoms and Optionally Substituted with a Halogen Atom (See Production Example 7)

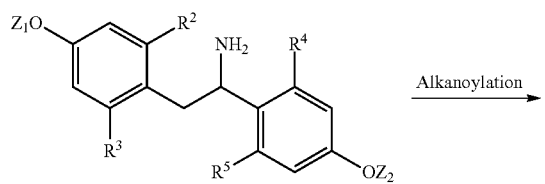

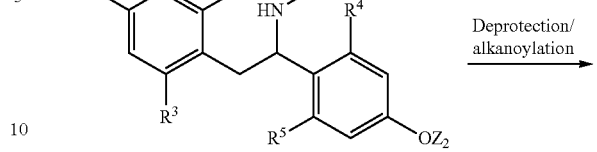

(1-i)

wherein $R^2$ to $R^6$, $Z_1$ and $Z_2$ are as defined above, and $Y^a$ represents an alkanoyl group having 2 to 6 carbon atoms and optionally substituted with a halogen atom.

<Synthesis Example 8>: Production Example of Compound Wherein $R^1$ is 4- to 6-Membered Saturated Cyclic Amino Group (See Production Example 8)

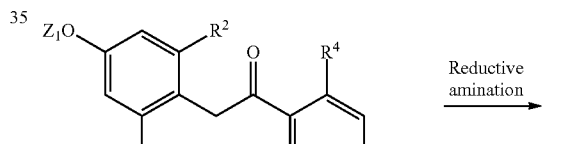

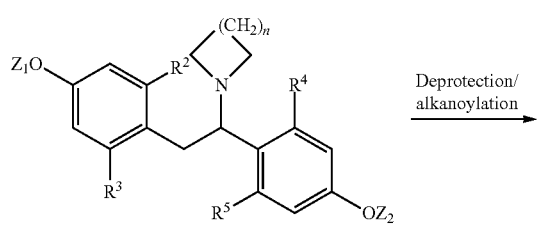

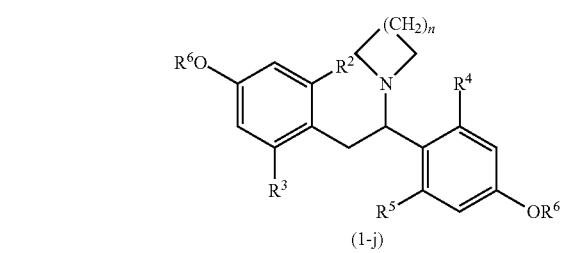

(1-j)

wherein $R^2$ to $R^6$, $Z_1$ and $Z_2$ are as defined above, and n represents an integer from 1 to 5.

<Synthesis Example 9>: Production Example of Compound Wherein R¹ is 5- or 6-Membered Nitrogen-Containing Heteroaryl Group (See Production Examples 9 to 13)
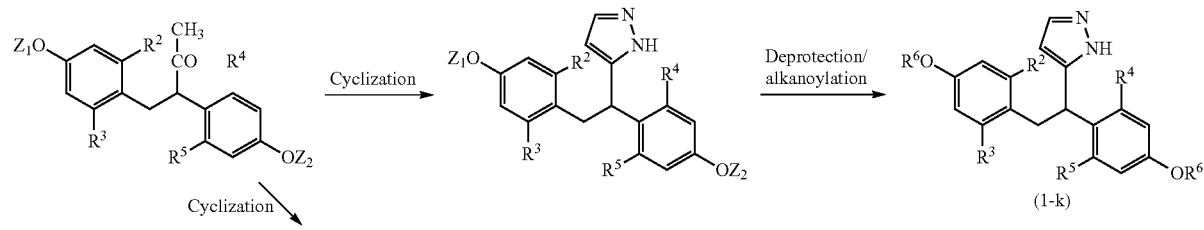
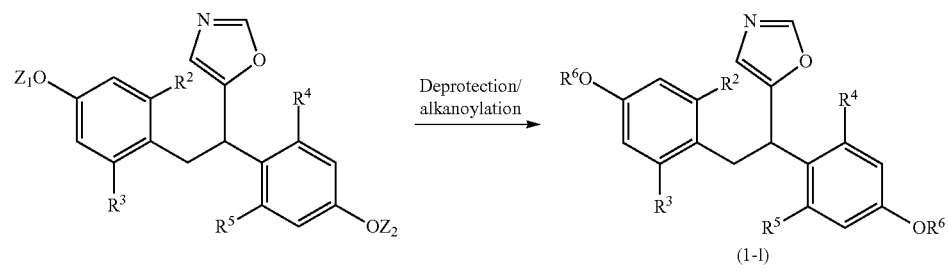
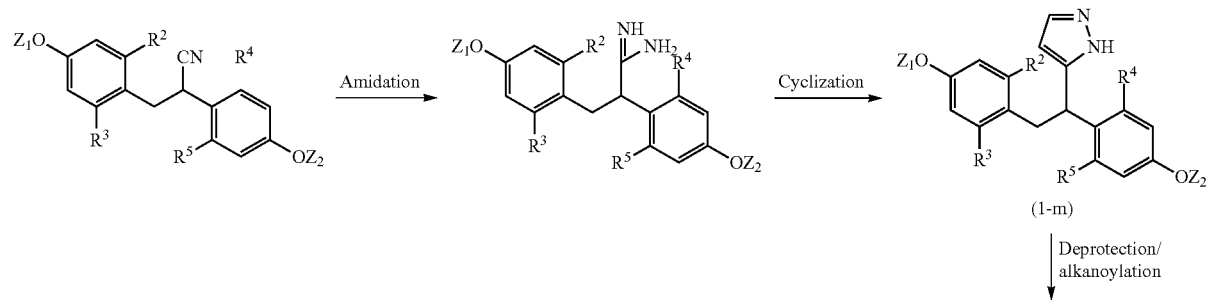
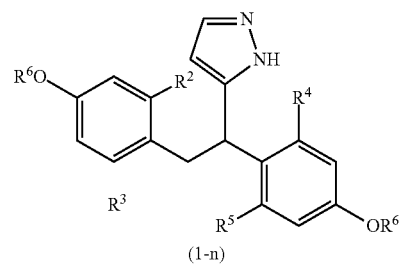

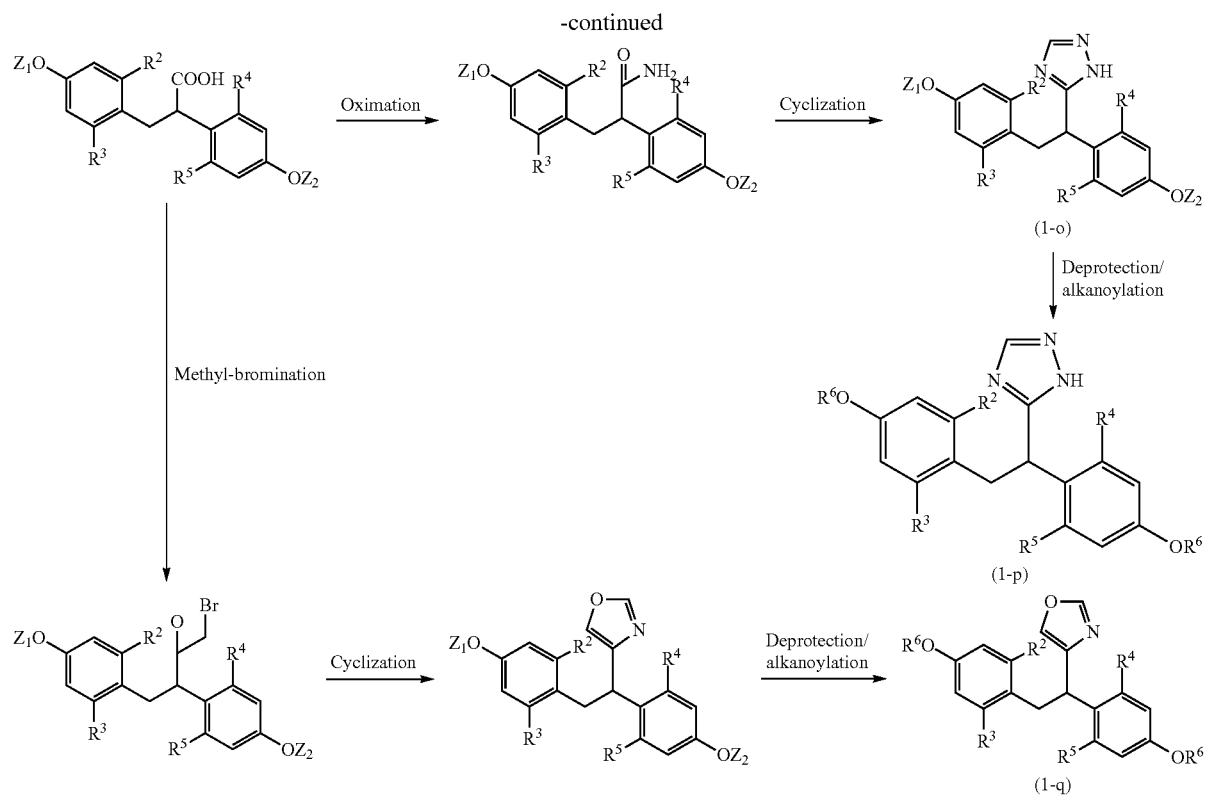

wherein $R^2$ to $R^6$, $Z_1$ and $Z_2$ are as defined above.

The compound of the present invention or the salt thereof may be a partially purified product as long as the product conforms to specifications acceptable as medicaments, quasi drugs, or cosmetics and exerts the advantageous effects of the present invention. Alternatively, the purity of the obtained partially purified product may be enhanced by appropriately combining separation and purification methods known in the art. Examples of the purification approach include organic solvent precipitation, centrifugation, ultrafiltration membrane, high-performance liquid chromatography, and column chromatography.

As shown in Examples described later, the compound of the present invention exhibited an excellent ERβ activating effect in an in vitro evaluation system exploiting a ligand binding domain (LBD) present in the molecular structure of ERβ. This evaluation system is a system exploiting difference in the sequence of the ligand binding domain (LBD) between ERα and ERβ (J Endocrinol 163: 379-383 (1999)), and enables selective activation of ERβ to be evaluated by determining the binding of a ligand to LBD and the activation of ER.

Accordingly, the ERP activation according to the present invention means higher affinity for ERβ than that for ERα, i.e., activation selective for ERβ. Specifically, ERP/ERα, a binding ratio between ERα and ERβ, is preferably 1 or more, more preferably 2 or more, even more preferably 3 or more, even more preferably 5 or more, even more preferably 10 or more. This ratio is preferably 300 or less, more preferably 200 or less. The ratio is in a range preferably from 1 to 300, more preferably from 2 to 300, even more preferably from 3 to 300, even more preferably from 5 to 300, even more preferably from 10 to 200.

The compound of the present invention exhibited an effect of activating the transcription of a target gene of ERβ in an evaluation system on the ability to activate transcription mediated by estrogen receptors (ERs) exploiting an estrogen response element (ERE, AGGTCAnnnTGACCT).

Thus, the compound of the present invention or the salt thereof is effective for, for example, preventing or ameliorating skin aging symptoms ascribable to a decreased amount of estrogen (skin wrinkles, sag (loosening), and reduction in the elasticity or fitness of the skin), preventing or ameliorating menopause disorder such as hot flash, inhibiting sebum secretion, preventing or ameliorating prostatic hyperplasia, and inhibiting androgen activation, particularly, effective for preventing, ameliorating or treating symptoms of various diseases for which the activation of ERβ is considered to be useful.

In this context, the amelioration of skin wrinkles or sag encompasses an effect of, for example, inhibiting the occurrence of wrinkles or sag, smoothing out the appearance of wrinkles, reducing or eliminating wrinkles or sag, or diminishing the appearance of wrinkles or sag.

The hot flash is a symptom ascribable to reduction in body temperature regulation function by disturbed autonomic nerves associated with a decreased amount of female hormone, and means symptoms such as local elevation of body surface temperatures, and glow, rush of blood to head, hectic flush, and excessive sweating associated therewith.

Androgen has been reported to have an effect of enhancing the secretion of sebum in the skin and an effect of enhancing the enlargement of the prostate. Meanwhile, it has been reported that the enlargement of the prostate induced by androgen is markedly inhibited by administering an ERβ activating agent to rats with the prostate enlarged by androgen (Patent Literature 17 described above). Accordingly, the activation of ERβ is considered to be able to inhibit androgen effects (anti-androgen effect).

Thus, the compound of the present invention or the salt thereof is capable of serving as an ERβ activating agent, a skin aging preventing or ameliorating agent, a sebum secretion inhibiting agent, an acne preventing or ameliorating agent, a hot flash preventing or ameliorating agent, a prostatic hyperplasia preventing or ameliorating agent, and an androgen activation inhibiting agent (hereinafter, referred to as an ERP activating agent, etc.), and can be used for producing the ERβ activating agent, etc.

The compound of the present invention or the salt thereof can be used for selectively activating ERβ, preventing or ameliorating aging symptoms of the skin, inhibiting the secretion of sebum, preventing or ameliorating acne, preventing or ameliorating hot flash, preventing or ameliorating prostatic hyperplasia, and inhibiting androgen activation, for humans. In this context, the use for humans may be therapeutic use or may be non-therapeutic use.

The ERβ activating agent, etc. may be a medicament or a quasi drug for a human or an animal which exerts each effect of selectively activating ERβ, preventing or ameliorating aging symptoms of the skin, inhibiting the secretion of sebum, preventing or ameliorating acne, preventing or ameliorating hot flash, preventing or ameliorating prostatic hyperplasia, or inhibiting androgen activation, or may be a material or a preparation which is blended for use into the medicament, etc.

The dosage form of the medicament may be any of, for example, injections, suppositories, inhalants, percutaneous absorption formulations, various formulations for external use, tablets, capsules, granules, powders, and syrups. The administration mode thereof may be any of oral administration (internal use) and parenteral administration (external use and injection).

Such pharmaceutical preparations in various dosage forms can be prepared using the compound of the present invention or the salt thereof singly or in appropriate combination with other pharmaceutically acceptable additives such as an excipient, a binder, an extender, a disintegrant, a surfactant, a lubricant, a dispersant, a buffer, a preservative, a corrigent, a flavor, a coating agent, a carrier, and a diluent.

Among these administration modes, a preferred mode is oral administration or administration for external use. The content of the compound of the present invention or the salt thereof in a preparation is generally 0.00001% by mass or more, preferably 0.0001% by mass or more, and 10% by mass or less, preferably 5% by mass or less. The content is from 0.00001 to 10% by mass, preferably from 0.0001 to 5% by mass.

The quasi drug is preferably in a form such as a skin formulation for external use or a cleansing agent, and can be provided in various dosage forms such as lotions, emulsions, gels, creams, ointments, powders, and granules according to a use method. Such quasi drugs in various dosage forms can be prepared by appropriately combining the compound of the present invention or the salt thereof with an oil component, a moisturizer, a powder, a dye, an emulsifier, a solubilizer, a cleansing agent, an ultraviolet absorber, a thickener, agents (e.g., anti-inflammatory agents, germicides, antioxidants, and vitamins), a flavor, a resin, an antibacterial and antifungal agent, plant extracts, alcohols, or the like which may be blended into a skin formulation for external use, etc.

The content of the compound of the present invention or the salt thereof in the quasi drug is usually 0.0001% by mass or more, preferably 0.001% by mass or more, more preferably 0.01% by mass or more, and 20% by mass or less, preferably 10% by mass or less, more preferably 5% by mass or less. The content is from 0.0001 to 20% by mass, preferably from 0.001 to 10% by mass, more preferably from 0.01 to 5% by mass.

The applied amount of the preparation, particularly, the medicament or the quasi drug, may vary depending on the state, body weight, sex, age or other factors of a subject, and is 0.01 mg or more, preferably 0.1 mg or more, and 100 mg or less, preferably 10 mg or less, per kg per day in terms of the compound of the present invention or the salt thereof per adult in the case of oral administration or ingestion. The amount is preferably from 0.01 mg to 100 mg/kg, more preferably from 0.1 mg to 10 mg/kg.

Examples of the subject to which the ERβ activating agent, etc. of the present invention are applied include humans who demand the prevention or amelioration of symptoms which appear due to a decreased amount of estrogen, for example, skin aging symptoms such as skin wrinkles, sag (loosening), and reduction in the elasticity or fitness of the skin, menopause disorder such as hot flash, excessive secretion of sebum, acne, prostatic hyperplasia, or androgen activation.

As for the embodiments mentioned above, the present invention discloses the following aspects.

<1> A compound represented by the following formula (1):

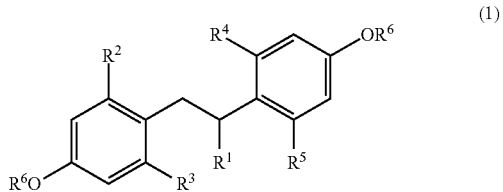

wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, a 1-trifluoromethyl-1-hydroxymethyl group, or a 1-methylpropyl group; $R^2$ to $R^5$ are the same or different and each represent a hydrogen atom or a fluorine atom; and $R^6$ represents a hydrogen atom or an alkanoyl group having 2 to 5 carbon atoms, or a salt thereof.

<2> An ERβ activating agent comprising the compound represented by the formula (1) or the salt thereof according to <1> as an active ingredient.

<3> A skin aging preventing or ameliorating agent comprising the compound represented by the formula (1) or the salt thereof according to <1> as an active ingredient.

<4> A sebum secretion inhibiting agent comprising the compound represented by the formula (1) or the salt thereof according to <1> as an active ingredient.

<5> An acne preventing or ameliorating agent comprising the compound represented by the formula (1) or the salt thereof according to <1> as an active ingredient.

<6> A hot flash preventing or ameliorating agent comprising the compound represented by the formula (1) or the salt thereof according to <1> as an active ingredient.

<7> A prostatic hyperplasia preventing or ameliorating agent comprising the compound represented by the formula (1) or the salt thereof according to <1> as an active ingredient.

<8> An androgen activation inhibiting agent comprising the compound represented by the formula (1) or the salt thereof according to <1> as an active ingredient.

<9> The compound or the salt thereof according to <1>, wherein in the formula (1), $R^1$ is a cycloalkyl group having 3 to 8 carbon atoms, or an alkenyl group having 2 to 6 carbon atoms and optionally substituted with a halogen atom; each of $R^2$ and $R^3$ is a fluorine atom and each of $R^4$ and $R^5$ is a hydrogen atom, or each of $R^2$ and $R^4$ is a fluorine atom and each of $R^3$ and $R^5$ is a hydrogen atom (or each of $R^2$ and $R^4$ is a hydrogen atom and each of $R^3$ and $R^5$ is a fluorine atom); and $R^6$ is a hydrogen atom.

<10> The compound or the salt thereof according to <1>, wherein in the formula (1), $R^1$ is an alkenyl group having 2 to 6 carbon atoms and optionally substituted with a halogen atom, more preferably $R^1$ is an alkenyl group having 2 to 4 carbon atoms and optionally monosubstituted or disubstituted with a fluorine atom or a chlorine atom, and even more preferably $R^1$ is an ethenyl group monosubstituted or disubstituted with a fluorine atom or a chlorine atom; each of $R^2$ and $R^3$ is a fluorine atom and each of $R^4$ and $R^5$ is a hydrogen atom, or each of $R^2$ and $R^4$ is a fluorine atom and each of $R^3$ and $R^5$ is a hydrogen atom (or each of $R^2$ and $R^4$ is a hydrogen atom and each of $R^3$ and $R^5$ is a fluorine atom); and $R^6$ is a hydrogen atom.

<11> The compound or the salt thereof according to <1>, wherein the formula (1) is the following formula (1A) or (1B):

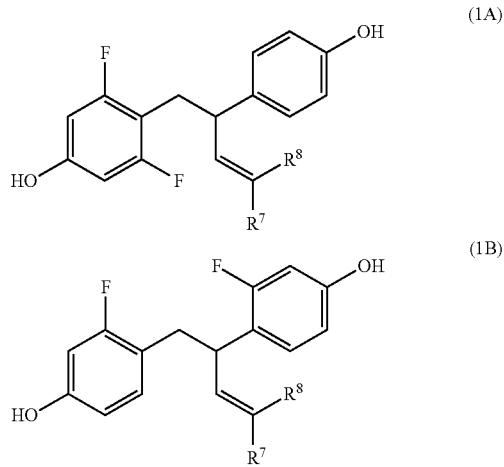

wherein $R^7$ represents a hydrogen atom, a fluorine atom or a chlorine atom, and $R^8$ represents a fluorine atom or a chlorine atom.

<12> The compound or the salt thereof according to <1>, wherein in the formula (1), $R^1$ is a 2,2-difluoroethenyl group, a 2,2-dichloroethenyl group, a 2-fluoroethenyl group, or a 2-chloroethenyl group; each of $R^2$ and $R^3$ is a fluorine atom and each of $R^4$ and $R^5$ is a hydrogen atom, or each of $R^2$ and $R^4$ is a fluorine atom and each of $R^3$ and $R^5$ is a hydrogen atom (or each of $R^2$ and $R^4$ is a hydrogen atom and each of $R^3$ and $R^5$ is a fluorine atom); and $R^6$ is a hydrogen atom.

<13> Use of the compound represented by the formula (1) or the salt thereof according to <1> for producing a skin aging preventing or ameliorating agent.

<14> Use of the compound represented by the formula (1) or the salt thereof according to <1> for producing a sebum secretion inhibiting agent.

<15> Use of the compound represented by the formula (1) or the salt thereof according to <1> for producing an acne preventing or ameliorating agent.

<16> Use of the compound represented by the formula (1) or the salt thereof according to <1> for producing a hot flash preventing or ameliorating agent.

<17> Use of the compound represented by the formula (1) or the salt thereof according to <1> for producing a prostatic hyperplasia preventing or ameliorating agent.

<18> Use of the compound represented by the formula (1) or the salt thereof according to <1> for producing an androgen activation inhibiting agent.

<19> The compound represented by the formula (1) or the salt thereof according to <1> for use in the prevention or amelioration of skin aging.

<20> The compound represented by the formula (1) or the salt thereof according to <1> for use in the inhibition of sebum secretion.

<21> The compound represented by the formula (1) or the salt thereof according to <1> for use in the prevention or amelioration of acne.

<22> The compound represented by the formula (1) or the salt thereof according to <1> for use in the prevention or amelioration of hot flash.

<23> The compound represented by the formula (1) or the salt thereof according to <1> for use in the prevention or amelioration of prostatic hyperplasia.

<24> The compound represented by the formula (1) or the salt thereof according to <1> for use in the inhibition of androgen activation.

<25> Non-therapeutic use of the compound represented by the formula (1) or the salt thereof according to <1> for preventing or ameliorating skin aging.

<26> Non-therapeutic use of the compound represented by the formula (1) or the salt thereof according to <1> for inhibiting sebum secretion.

<27> Non-therapeutic use of the compound represented by the formula (1) or the salt thereof according to <1> for preventing or ameliorating acne.

<28> Non-therapeutic use of the compound represented by the formula (1) or the salt thereof according to <1> for preventing or ameliorating hot flash.

<29> Non-therapeutic use of the compound represented by the formula (1) or the salt thereof according to <1> for preventing or ameliorating prostatic hyperplasia.

<30> Non-therapeutic use of the compound represented by the formula (1) or the salt thereof according to <1> for inhibiting androgen activation.

<31> A method for preventing or ameliorating skin aging, comprising administering or ingesting the compound represented by the formula (1) or the salt thereof according to <1> in an effective amount to a subject in need thereof.

<32> A method for inhibiting sebum secretion, comprising administering or ingesting the compound represented by the formula (1) or the salt thereof according to <1> in an effective amount to a subject in need thereof.

<33> A method for preventing or ameliorating acne, comprising administering or ingesting the compound represented by the formula (1) or the salt thereof according to <1> in an effective amount to a subject in need thereof.

<34> A method for preventing or ameliorating hot flash, comprising administering or ingesting the compound represented by the formula (1) or the salt thereof according to <1> in an effective amount to a subject in need thereof.

<35> A method for preventing or ameliorating prostatic hyperplasia, comprising administering or ingesting the compound represented by the formula (1) or the salt thereof according to <1> in an effective amount to a subject in need thereof.

<36> A method for inhibiting androgen activation, comprising administering or ingesting the compound represented by the formula (1) or the salt thereof according to <1> in an effective amount to a subject in need thereof.

EXAMPLES

Production Example 1

Synthesis of 4,4'-(1-cyclopropylethane-1,2-diyl)diphenol (compound 1), 4,4'-(1-cyclobutylethane-1,2-diyl)diphenol (compound 2), 4,4'-(1-cyclohexylethane-1,2-diyl)diphenol (compound 3), and 4,4'-(1-cyclohexylethane-1,2-diyl)diphenol (compound 4)

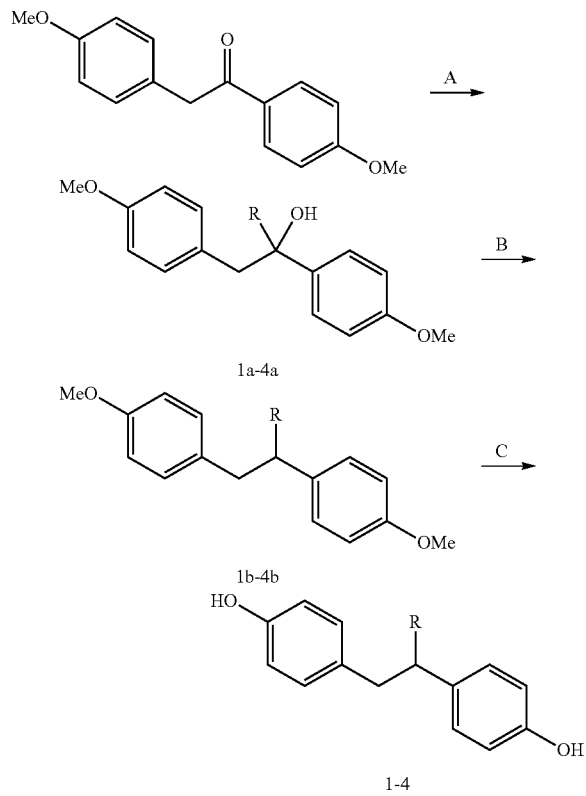

1) Step A

To deoxyanisoin, a 10-fold amount of tetrahydrofuran (hereinafter, abbreviated to THF) and 3 equivalents of RMgX (X=Cl or Br, a solution in THF) were added at room temperature in an argon atmosphere, and the mixture was stirred overnight under reflux. After confirmation of the completion of the reaction by thin-layer chromatography (hereinafter, abbreviated to TLC), the reaction solution was neutralized by the addition of a saturated aqueous solution of sodium bicarbonate under ice cooling, followed by extraction with ethyl acetate. Then, the organic layer was washed with saturated saline and dried over anhydrous magnesium sulfate. After filtration, the filtrate was concentrated, and the obtained crude product was purified by silica gel column chromatography (hexane/ethyl acetate) to obtain a product (compounds 1a to 4a).

Compound 1a: R=cyclopropyl
Colorless clear oil (1.53 g, yield: 90%)
$^1$H NMR (600 MHz, CDCl$_3$): δ 7.36-7.33 (m, 2H), 6.90-6.84 (m, 4H), 6.74-6.71 (m, 2H), 3.81 (s, 3H), 3.75 (s, 3H), 3.13 (d, J=13.4 Hz, 1H), 3.09 (d, J=13.4 Hz, 1H), 1.50 (s, 1H), 1.32-1.27 (m, 1H), 0.44-0.34 (m, 3H), 0.31-0.26 (m, 1H).
$^{13}$C NMR (150 MHz, CDCl$_3$): δ 158.32, 158.30, 138.5, 131.7, 128.5, 127.0, 113.4, 113.1, 74.4, 55.22, 55.16, 48.4, 20.8, 1.5, 0.8.

Compound 2a: R=cyclobutyl
Pale yellow clear oil (1.44 g, yield: 76%)
$^1$H NMR (600 MHz, CDCl$_3$): δ 7.20-7.16 (m, 2H), 6.83-6.80 (m, 2H), 6.75-6.71 (m, 2H), 6.70-6.66 (m, 2H), 3.80 (s, 3H), 3.74 (s, 3H), 2.95 (d, J=13.5 Hz, 1H), 2.92-2.84 (m, 1H), 2.84 (d, J=13.5 Hz, 1H), 2.22-2.14 (m, 1H), 2.00-1.92 (m, 1H), 1.84-1.76 (m, 2H), 1.72-1.64 (m, 1H), 1.62-1.54 (m, 1H).
$^{13}$C NMR (150 MHz, CDCl$_3$): δ 158.2, 158.0, 136.9, 131.4, 128.4, 127.0, 113.4, 113.1, 76.6, 55.2, 55.1, 45.0, 44.1, 22.4, 22.3, 16.8.

Compound 3a: R=cyclopentyl
Pale yellow clear oil (82.1 mg, yield: 5%)
$^1$H NMR (600 MHz, CDCl$_3$): δ 7.20-7.16 (m, 2H), 6.82-6.79 (m, 2H), 6.74-6.70 (m, 2H), 6.68-6.65 (m, 2H), 3.80 (s, 3H), 3.73 (s, 3H), 3.12 (d, J=13.5 Hz, 1H), 3.02 (d, J=13.5 Hz, 1H), 2.43 (dddd, J=8.9, 8.9, 8.8, 8.8 Hz, 1H), 1.88-1.82 (m, 1H), 1.75-1.40 (m, 6H), 1.35-1.20 (m, 2H).
$^{13}$C NMR (150 MHz, CDCl$_3$) δ 158.2, 157.8, 138.2, 131.5, 128.4, 127.1, 113.3, 112.9, 77.7, 55.15, 55.10, 49.6, 46.8, 27.6, 26.7, 26.1, 25.7.

Compound 4a: R=cyclohexyl
Colorless clear oil (1.14 g, yield: 56%)
$^1$H NMR (600 MHz, CDCl$_3$): δ 7.22-7.19 (m, 2H), 6.84-6.78 (m, 4H), 6.70-6.66 (m, 2H), 3.81 (s, 3H), 3.73 (s, 3H), 3.16 (d, J=13.6 Hz, 1H), 3.10 (d, J=13.6 Hz, 1H), 2.06-2.00 (m, 1H), 1.80-1.57 (m, 6H), 1.28-1.12 (m, 2H), 1.09-0.92 (m, 3H).
$^{13}$C NMR (150 MHz, CDCl$_3$): δ 158.2, 157.9, 136.9, 131.7, 128.5, 127.4, 113.4, 112.8, 78.4, 55.15, 55.11, 48.0, 44.3, 27.8, 27.0, 26.8, 26.6, 26.4.

2) Step B

To the compound obtained in step A, a 15-fold amount of dichloromethane was added at room temperature in an argon atmosphere, then 2 equivalents of triethylsilane and 2 equivalents of a boron trifluoride-diethyl ether complex were added under ice cooling, and the mixture was stirred for 1 hour under ice cooling. After confirmation of the completion of the reaction by TLC, the reaction solution was separated into organic and aqueous layers by the addition of water and chloroform. Then, the organic layer was dried over anhydrous magnesium sulfate. After filtration, the filtrate was concentrated, and the obtained crude product was purified by silica gel column chromatography (hexane/ethyl acetate) to obtain a product (compounds 1b to 4b).

Compound 1b: R=cyclopropyl
Pale yellow clear oil (589 mg, yield: 86%)
$^1$H NMR (600 MHz, CDCl$_3$): δ 7.04-7.01 (m, 2H), 6.92-6.88 (m, 2H), 6.81-6.78 (m, 2H), 6.73-6.70 (m, 2H), 3.78 (s, 3H), 3.75 (s, 3H), 3.00 (dd, J=13.6, 6.2 Hz, 1H), 2.90 (dd, J=13.6, 8.0 Hz, 1H), 2.02-1.97 (m, 1H), 1.03-0.96 (m, 1H), 0.55-0.49 (m, 1H), 0.39-0.34 (m, 1H), 0.10-0.00 (m, 2H).
$^{13}$C NMR (150 MHz, CDCl$_3$): δ 157.8, 157.6, 137.2, 132.7, 130.2, 128.6, 113.4, 113.3, 55.2, 52.2, 42.6, 16.9, 5.7, 3.7.

Compound 2b: R=cyclobutyl

Pale yellow clear oil (562 mg, yield: 94%)

$^1$H NMR (600 MHz, CDCl$_3$): δ 6.92-6.89 (m, 2H), 6.83-6.80 (m, 2H), 6.77-6.74 (m, 2H), 6.70-6.67 (m, 2H), 3.76 (s, 3H), 3.74 (s, 3H), 2.83 (dd, J=13.3, 4.3 Hz, 1H), 2.65 (ddd, J=14.0, 9.4, 4.3 Hz, 1H), 2.59 (dd, J=13.3, 9.4 Hz, 1H), 2.58-2.50 (m, 1H), 2.14-2.08 (m, 1H), 1.80-1.69 (m, 4H), 1.55-1.47 (m, 1H). $^{13}$C NMR (150 MHz, CDCl$_3$) δ 157.6, 157.5, 135.3, 132.8, 130.0, 129.0, 113.3, 113.2, 55.13, 55.10, 54.4, 40.9, 39.6, 28.2, 26.9, 17.6.

Compound 3b: R=cyclopentyl

Pale yellow clear oil (59.8 mg, yield: 83%)

$^1$H NMR (600 MHz, CDCl$_3$): δ 6.92-6.88 (m, 2H), 6.80-6.76 (m, 2H), 6.75-6.72 (m, 2H), 6.68-6.65 (m, 2H), 3.76 (s, 3H), 3.73 (s, 3H), 3.03 (dd, J=13.6, 4.2 Hz, 1H), 2.68 (dd, J=13.6, 10.1 Hz, 1H), 2.47 (ddd, J=10.1, 4.2 Hz, 1H), 2.13-2.05 (m, 1H), 2.04-1.96 (m, 1H), 1.70-1.36 (m, 5H), 1.34-1.26 (m, 1H), 1.02-0.94 (m, 1H). $^{13}$C NMR (150 MHz, CDCl$_3$): δ 157.5, 157.4, 136.9, 133.1, 130.0, 129.2, 113.2, 113.1, 55.1, 53.8, 45.8, 41.3, 31.9, 31.5, 25.4, 25.0.

Compound 4b: R=cyclohexyl

Colorless clear oil (333 mg, yield: quant.)

$^1$H NMR (600 MHz, CDCl$_3$): δ 6.95-6.91 (m, 2H), 6.87-6.83 (m, 2H), 6.77-6.73 (m, 2H), 6.70-6.66 (m, 2H), 3.77 (s, 3H), 3.73 (s, 3H), 3.07 (dd, J=13.6, 5.3 Hz, 1H), 2.70 (dd, J=13.6, 9.7 Hz, 1H), 2.52 (ddd, J=9.7, 6.9, 5.3 Hz, 1H), 1.94-1.89 (m, 1H), 1.76-1.70 (m, 1H), 1.67-1.57 (m, 2H), 1.55-1.46 (m, 2H), 1.28-1.19 (m, 1H), 1.17-0.93 (m, 3H), 0.83-0.74 (m, 1H).

$^{13}$C NMR (150 MHz, CDCl$_3$): δ 157.5, 157.3, 135.7, 133.5, 129.9, 129.6, 113.3, 113.0, 55.11, 55.10, 53.5, 42.3, 38.4, 31.8, 30.3, 26.60, 26.57, 26.51.

3) Step C

To the compound obtained in step B, a 20-fold amount of dichloromethane and 50 equivalents of BF$_3$·SMe$_2$ were added at room temperature in an argon atmosphere, and the mixture was stirred overnight. After confirmation of the completion of the reaction by TLC, the reaction solution was neutralized by the addition of a saturated aqueous solution of sodium bicarbonate under ice cooling, followed by extraction with ethyl acetate. The organic layer was washed with saturated saline and then dried over anhydrous magnesium sulfate. After filtration, the filtrate was concentrated, and the obtained crude product was purified by silica gel column chromatography (hexane/ethyl acetate, or chloroform/methanol) to obtain a product.

Compound 1: R=cyclopropyl

Colorless clear oil (39.7 mg, yield: 69%)

HRMS (ESI, negative mode) calc: 253.1234 [M−H]$^-$; found: 253.1240.

$^1$H NMR (600 MHz, acetone-d$_6$): δ 7.99 (brs, 2H), 7.00-6.96 (m, 2H), 6.87-6.84 (m, 2H), 6.72-6.69 (m, 2H), 6.65-6.61 (m, 2H), 2.97 (dd, J=13.6, 6.2 Hz, 1H), 2.87 (dd, J=13.6, 8.4 Hz, 1H), 2.00 (ddd, J=8.6, 8.6, 6.2 Hz, 1H), 1.06-0.98 (m, 1H), 0.52-0.45 (m, 1H), 0.33-0.26 (m, 1H), 0.11-0.05 (m, 1H), 0.04-0.02 (m, 1H).

$^{13}$C NMR (150 MHz, acetone-d$_6$): δ 156.4, 156.2, 136.9, 132.5, 131.0, 129.5, 115.6, 115.5, 53.2, 43.2, 30.6, 18.0, 6.1, 4.1.

Compound 2: R=cyclobutyl

Pale yellow clear oil (80.9 mg, yield: quant.)

HRMS (ESI, negative mode) calc 313.1445 [M+HCOOH−H]$^-$; found: 313.1440.

$^1$H NMR (600 MHz, CD$_3$OD): δ 6.82-6.78 (m, 2H), 6.72-6.68 (m, 2H), 6.62-6.58 (m, 2H), 6.55-6.51 (m, 2H), 2.78 (dd, J=13.1, 3.9 Hz, 1H), 2.60-2.48 (m, 1H), 2.57 (dd, J=9.1, 3.9 Hz, 1H), 2.50 (dd, J=13.1, 9.1 Hz, 1H), 2.15-2.08 (m, 1H), 1.84-1.65 (m, 4H), 1.55-1.47 (m, 1H).

$^{13}$C NMR (150 MHz, CD$_3$OD): δ 156.4, 156.2, 135.4, 133.0, 131.1, 130.2, 115.7, 115.6, 56.3, 42.6, 40.7, 29.3, 28.1, 18.5.

Compound 3: R=cyclopentyl

White solid (43.2 mg, yield: quant.)

Melting point: 131-132° C.

HRMS (ESI, negative mode) calc: 281.1547 [M−H]$^-$; found: 281.1539.

$^1$H NMR (600 MHz, acetone-d$_6$): δ 7.98 (brs, 1H), 7.93 (brs, 1H), 6.89-6.85 (m, 2H), 6.76-6.73 (m, 2H), 6.67-6.64 (m, 2H), 6.59-6.56 (m, 2H), 3.01 (dd, J=13.6, 4.2 Hz, 1H), 2.67 (dd, J=13.6, 10.3 Hz, 1H), 2.48 (ddd, J=10.3, 10.3, 4.2 Hz, 1H), 2.13-2.06 (m, 1H), 2.03-1.96 (m, 1H), 1.69-1.48 (m, 3H), 1.46-1.29 (m, 3H), 1.05-0.97 (m, 1H).

$^{13}$C NMR (150 MHz, acetone-d$_6$): δ 156.2, 156.0, 136.4, 132.7, 130.8, 130.0, 115.45, 115.41, 54.6, 47.0, 41.9, 32.4, 32.2, 26.0, 25.6.

Compound 4: R=cyclohexyl

White solid (89.5 mag, yield: 98%)

Melting point: 74-76° C.

HRMS (ESI, negative mode) calc: 295.1704 [M−H]$^-$; found: 295.1697.

$^1$H NMR (600 MHz, CD$_3$OD): δ 6.83-6.79 (m, 2H), 6.75-6.71 (m, 2H), 6.62-6.59 (m, 2H), 6.54-6.50 (m, 2H), 3.02 (dd, J=13.5, 5.2 Hz, 1H), 2.62 (dd, J=13.5, 10.0 Hz, 1H), 2.46 (ddd, J=9.9, 7.2, 5.2 Hz, 1H), 1.97-1.91 (m, 1H), 1.78-1.72 (m, 1H), 1.67-1.45 (m, 4H), 1.31-1.22 (m, 1H), 1.19-1.05 (m, 2H), 1.04-0.95 (m, 1H), 0.78 (ddd, J=24.4, 12.4, 3.4 Hz, 1H).

$^{13}$C NMR (150 MHz, CD$_3$OD): δ 156.3, 156.0, 135.9, 133.8, 131.0, 130.8, 115.6, 115.5, 55.1, 43.9, 39.7, 33.1, 31.7, 27.83, 27.80, 27.7.

Production Example 2 Synthesis of 4,4'-(pent-3-ene-1,2-diyl)diphenol (compound 5)

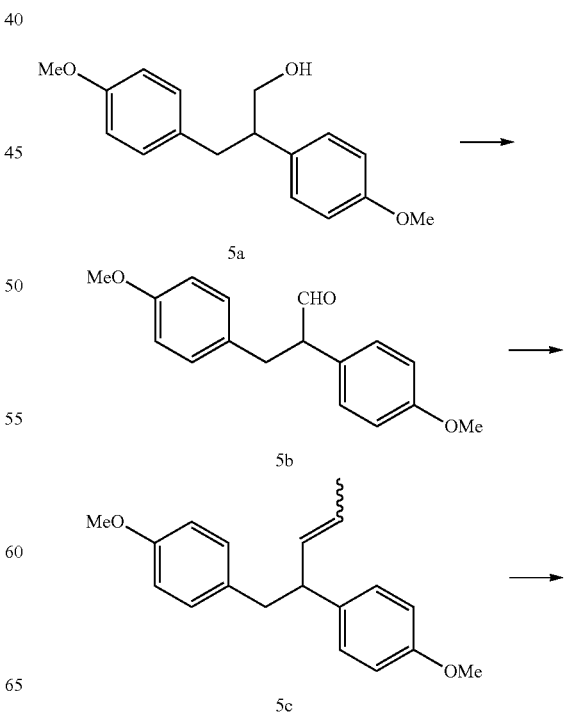

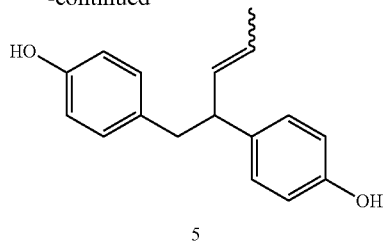

1) Compound 5a was synthesized according to the approach of the literature (Meyers et al., J. Med. Chem. 2001, 44, 4230-4251).

2) Synthesis of Compound 5b

To compound 5a (303.3 mg, 1.11 mmol), dichloromethane (15 mL) and a Dess-Martin reagent (1.21 g, 3.34 mmol) were added at room temperature in an argon atmosphere, and the mixture was stirred for 2 hours. After confirmation of the completion of the reaction by TLC, the reaction solution was added to a mixed solution of a saturated aqueous solution of sodium bicarbonate/a saturated aqueous solution of sodium thiosulfate (1/1 (volume), a total of 20 mL) for reduction and neutralization, followed by extraction with chloroform (30 mL) twice. The organic layer was washed with saturated saline (30 mL) and dried over anhydrous magnesium sulfate. After filtration, the filtrate was concentrated, and the obtained crude product (595.7 mg) was purified by silica gel column chromatography (hexane/ethyl acetate) to obtain pale yellow clear oil 5b (213.7 mg, yield: 71%).

$^1$H NMR (600 MHz, CDCl$_3$): δ 9.70 (d, J=1.6 Hz, 1H), 7.06-7.02 (m, 2H), 6.97-6.94 (m, 2H), 6.89-6.85 (m, 2H), 6.76-6.73 (m, 2H), 3.80 (s, 3H), 3.75 (s, 3H), 3.73 (ddd, J=8.0, 6.8, 1.6 Hz, 1H), 3.36 (dd, J=14.2, 6.8 Hz, 1H), 2.88 (dd, J=14.2, 8.0 Hz, 1H).

$^{13}$C NMR (150 MHz, CDCl$_3$): δ 200.2, 159.1, 158.0, 130.9, 130.1, 130.0, 127.6, 114.4, 113.7, 60.3, 55.3, 55.2, 35.3.

3) Synthesis of Compound 5c

THF (1.7 mL) and chromium chloride (257.3 mg, 2.09 mmol) were added at room temperature in an argon atmosphere. A solution of compound 5b (69.0 mg, 0.255 mmol) and CH$_3$CHI$_2$ (52 μL, 0.515 mmol) dissolved in THF (2 mL) was added thereto, and the mixture was stirred overnight. After confirmation of the completion of the reaction by TLC, the reaction solution was separated into organic and aqueous layers by the addition of diethyl ether (5 mL) and water (10 mL). Then, the organic layer was washed with saturated saline (10 mL) and dried over anhydrous magnesium sulfate. After concentration of a filtrate, the obtained crude product (152.7 mg) was purified by silica gel column chromatography (hexane/ethyl acetate) to obtain pale yellow clear oil 5c (59.3 mg, yield: 82%, E/Z=20/1 ($^1$H-NMR ratio)).

(E) Form
$^1$H NMR (600 MHz, CDCl$_3$): δ 7.06-7.02 (m, 2H), 6.95-6.91 (m, 2H), 6.82-6.79 (m, 2H), 6.76-6.73 (m, 2H), 5.61 (ddq, J=15.1, 7.5, 1.3 Hz, 1H), 5.33 (dqd, J=15.1, 6.2, 0.9 Hz, 1H), 3.78 (s, 3H), 3.76 (s, 3H), 3.41 (ddd, J=7.6, 7.5, 7.4 Hz, 1H), 2.91 (dd, J=13.6, 7.5 Hz, 1H), 2.86 (dd, J=13.6, 7.6 Hz, 1H), 1.62 (ddd, J=6.2, 1.3, 0.8 Hz, 3H).

$^{13}$C NMR (150 MHz, CDCl$_3$): δ 157.8, 157.7, 136.7, 134.6, 132.6, 130.1, 128.6, 124.9, 113.7, 113.4, 55.22, 55.17, 50.0, 42.0, 18.0.

(Z) Form
$^1$H NMR (600 MHz, CDCl$_3$): δ 7.11-7.09 (m, 2H), 7.00-6.97 (m, 2H), 6.83-6.72 (m, 4H), 5.56 (dq, J=10.1, 1.7 Hz, 1H), 5.46-5.40 (m, 1H), 3.78 (s, 3H), 3.77 (s, 3H), 3.38-3.35 (m, 1H), 2.94 (dd, J=13.6, 6.4 Hz, 1H), 2.80 (dd, J=13.6, 8.3 Hz, 1H), 1.44 (dd, J=6.8, 1.7 Hz, 3H).

$^{13}$C NMR (150 MHz, CDCl$_3$): δ 157.8, 157.7, 137.2, 133.8, 132.5, 130.1, 128.3, 124.0, 113.8, 113.4, 55.22, 55.17, 44.4, 42.7, 12.9.

4) Synthesis of Compound 5

Compound 5c (26.1 mg, 0.0924 mmol) was subjected to the approach of step C of Production Example 1 to obtain colorless clear oil 5 (9.5 mg, yield: 40%, E/Z=40/1 ($^1$H NMR ratio)).

HRMS (ESI, negative mode) calc: 253.1234[M−H]$^−$; found: 253.1244.

(E) Form
$^1$H NMR (600 MHz, acetone-d$_6$): δ 8.03 (brs, 1H), 7.98 (brs, 1H), 7.01-6.97 (m, 2H), 6.91-6.87 (m, 2H), 6.73-6.70 (m, 2H), 6.68-6.64 (m, 2H), 5.61 (ddq, J=15.1, 7.7, 1.5 Hz, 1H), 5.33 (dqd, J=15.1, 6.4, 1.0 Hz, 1H), 3.40 (ddd, J=7.5, 7.5, 7.4 Hz, 1H), 2.86 (dd, J=7.5 Hz, 13.6 Hz, 1H), 2.82-2.78 (m, 1H), 1.58 (ddd, J=6.4, 1.5, 0.7, 3H).

$^{13}$C NMR (150 MHz, acetone-d$_6$): δ 156.4, 156.3, 136.40, 136.37, 132.2, 131.0, 129.5, 124.7, 115.8, 115.6, 51.0, 42.9, 18.1.

(Z) Form
$^1$H NMR (600 MHz, acetone-d$_6$): δ 8.01 (brs, 1H), 7.08-7.05 (m, 2H), 6.97-6.94 (m, 2H), 6.75-6.73 (m, 2H), 6.69-6.67 (m, 2H), 5.58 (dq, J=9.4, 1.6 Hz, 1H), 5.38-5.34 (m, 1H), 3.82-3.77 (m, 2H), 2.90-2.88 (m, 1H), 2.78-2.72 (m, 1H), 1.43 (dd, J=6.8, 1.6 Hz, 3H).

$^{13}$C NMR (150 MHz, acetone-d$_6$): δ 156.3, 156.2, 137.0, 135.5, 132.1, 131.1, 129.2, 123.6, 115.7, 115.5, 45.4, 43.5, 13.0.

Production Example 3 Synthesis of 4,4'-(3-methylpentane-1,2-diyl)diphenol (compound 6)

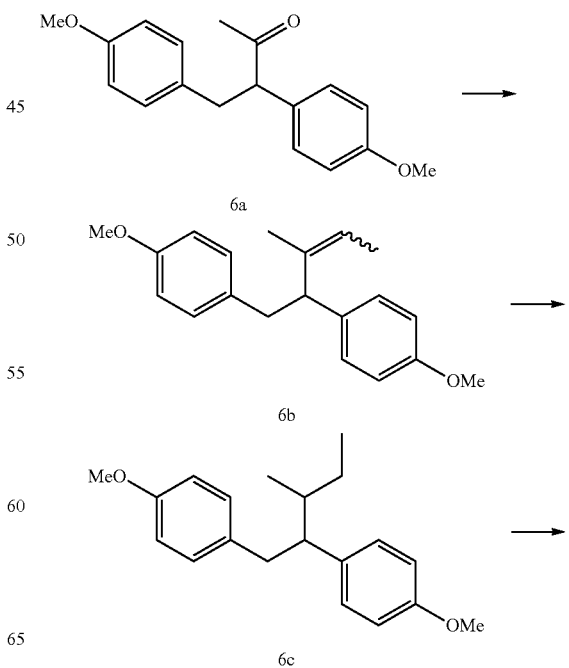

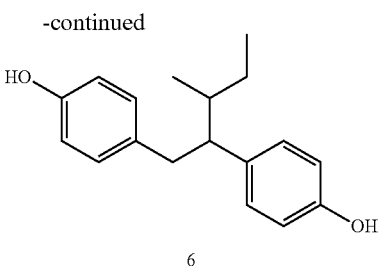

1) Compound 6a was synthesized according to the approach of the literature (Meyers et al., J. Med. Chem. 2001, 44, 4230-4251).

2) Synthesis of Compound 6b

To ethyl triphenyl phosphonium bromide (1.04 g, 2.80 mmol), THF (11 mL) and n-BuLi (1.8 mL, a solution of 15% by mass in hexane) were added under ice cooling in an argon atmosphere, and the mixture was stirred for 1 hour. Then, compound 6a (320 mg, 1.13 mmol, in THF, 5.6 mL) was added thereto, and the mixture was stirred at room temperature for 2 days. After confirmation of the completion of the reaction by TLC, a saturated aqueous solution of ammonium chloride was added thereto, followed by extraction with ethyl acetate (20 mL) three times. Then, the organic layer was washed with saturated saline and dried over anhydrous magnesium sulfate. After concentration of a filtrate, the obtained crude product (880 mg) was purified by silica gel column chromatography (hexane/ethyl acetate) to obtain colorless clear oil 6b (76.9 mg, yield: 23%, E/Z=1/7.7 ($^1$H NMR ratio)).

(Z) Form $^1$H NMR (600 MHz, CDCl$_3$): δ 7.20-7.14 (m, 2H), 7.10-7.06 (m, 2H), 6.86-6.81 (m, 2H), 6.80-6.76 (m, 2H), 5.22-5.17 (m, 1H), 4.15 (dd, J=9.9, 5.8 Hz, 1H), 3.79 (s, 3H), 3.77 (s, 3H), 3.10 (dd, J=13.7, 5.8 Hz, 1H), 2.94 (dd, J=13.7, 9.9 Hz, 1H), 1.52 (ddd, J=2.9, 1.5, 1.4 Hz, 3H), 1.45 (ddd, J=6.7, 2.8, 1.4 Hz, 3H).

$^{13}$C NMR (150 MHz, CDCl$_3$): δ 157.81, 157.77, 137.1, 135.8, 132.8, 129.7, 128.6, 120.7, 113.6, 113.5, 55.24, 55.20, 45.5, 36.5, 19.0, 13.1.

(E) Form $^1$H NMR (600 MHz, CDCl$_3$): δ 7.06-7.02 (m, 2H), 6.93-6.89 (m, 2H), 6.80-6.74 (m, 2H), 6.74-6.71 (m, 2H), 5.40-5.35 (m, 1H), 3.77 (s, 3H), 3.75 (s, 3H), 3.38 (dd, J=8.3, 7.1 Hz, 1H), 3.04 (dd, J=13.7, 7.1 Hz, 1H), 2.90 (dd, J=13.7, 8.3 Hz, 1H), 1.59-1.56 (m, 3H), 1.48-1.47 (m, 3H).

$^{13}$C NMR (150 MHz, CDCl$_3$): δ 157.84, 157.58, 137.9, 135.8, 133.1, 129.9, 128.9, 119.0, 113.40, 113.35, 55.18, 55.16, 38.6, 14.5, 13.4.

3) Synthesis of Compound 6c

To compound 6b (43.3 mg, 0.146 mmol), ethanol (1.5 mL) and 10% Pd/C (8.7 mg, 20 wt % (Tokyo Chemical Industry Co., Ltd., approximately 55% product wetted with water)) were added at room temperature in an argon atmosphere, and the mixture was stirred for 5.5 hours in a hydrogen atmosphere. After confirmation of the completion of the reaction by TLC, the reaction solution was filtered through celite, and the filter cake was washed with ethanol and ethyl acetate. After concentration of a filtrate, the obtained crude product (67.8 mg) was purified by silica gel column chromatography (hexane/ethyl acetate) to obtain colorless clear oil 6c (38.2 mg, yield: 88%, racemic mixtures of (2R(2S),3R(3S))- and (2R(2S),3S(3R))-diastereomers (1:1, $^1$H NMR ratio)).

$^1$H NMR (600 MHz, CDCl$_3$): δ 7.00-6.92 (m, 2H), 6.92-6.87 (m, 1H), 6.87-6.82 (m, 1H), 6.77-6.72 (m, 2H), 6.62-6.55 (m, 2H), 3.76 (s, 1.5H), 3.75 (s, 1.5H), 3.73 (s, 1.5H), 3.72 (s, 1.5H), 3.03 (dd, J=13.5, 4.8 Hz, 0.5H), 3.00 (dd, J=13.5, 5.7 Hz, 0.5H), 2.78 (dd, J=13.6, 9.1 Hz, 0.5H), 2.74-2.68 (m, 1H), 2.61 (ddd, J=10.1, 6.8, 4.6 Hz, 0.5H), 1.66-1.58 (m, 1H), 1.51-1.39 (m, 1H), 1.16-1.07 (m, 0.5H), 0.97 (d, J=6.8 Hz, 1.5H), 0.96-0.90 (m, 0.5H), 0.88 (t, J=6.8 Hz, 1.5H), 0.82 (t, J=7.4 Hz, 1.5H), 0.76 (d, J=6.8 Hz, 1.5H).

$^{13}$C NMR (150 MHz, CDCl$_3$): δ 157.65, 157.57, 157.5, 157.4, 135.9, 135.1, 133.5, 129.9, 129.84, 129.81, 129.6, 113.4, 113.3, 113.2, 113.1, 55.12, 55.11, 52.9, 51.6, 39.4, 38.8, 38.5, 38.1, 29.7, 27.6, 26.5, 17.1, 15.7, 11.6, 11.5.

4) Synthesis of Compound 6

Compound 6c (19.1 mg, 0.0640 mmol) was subjected to the approach of step C of Production Example 1 to obtain colorless clear oil 6 (17.0 mg, yield: 98%).

HRMS(ESI, negative mode) calc: 269.1547[M−H]$^−$; found: 269.1548.

$^1$H NMR (600 MHz, CDCl$_3$): δ 6.93-6.87 (m, 2H), 6.85-6.82 (m, 1H), 6.80-6.77 (m, 1H), 6.70-6.65 (m, 2H), 6.64-6.58 (m, 2H), 4.55 (d, J=1.0 Hz, 0.5H), 4.53 (d, J=1.2 Hz, 0.5H), 4.51 (d, J=1.0 Hz, 0.5H), 4.49 (d, J=1.1 Hz, 0.5H), 3.02 (dd, J=13.8, 4.8 Hz, 0.5H), 3.00 (dd, J=13.8, 5.9 Hz, 0.5H), 2.74 (dd, J=13.6, 9.3 Hz, 0.5H), 2.70-2.64 (m, 1H), 2.58 (dd, J=6.3, 4.0 Hz, 0.5H), 2.57 (dd, J=6.3, 4.0 Hz, 0.5H), 1.65-1.58 (m, 1H), 1.52-1.38 (m, 1H), 1.17-1.09 (m, 0.5H), 0.98 (d, J=6.9 Hz, 1.5H), 0.96-0.90 (m, 0.5H), 0.89 (t, J=7.4, 6.9 Hz, 1.5H), 0.81 (dd, J=6.9, 6.8 Hz, 1.5H), 0.75 (d, J=6.8 Hz, 1.5H).

$^{13}$C NMR (150 MHz, CDCl$_3$): δ 153.5, 153.4, 153.3, 153.2, 136.1, 135.3, 133.64, 133.63, 130.1, 130.05, 129.98, 129.7, 114.8, 114.73, 114.65, 114.57, 53.0, 51.7, 39.4, 38.9, 38.6, 38.2, 27.5, 26.5, 17.1, 15.8, 11.52, 11.45.

Production Example 4 Synthesis of 4,4'-(4,4-difluorobut-3-ene-1,2-diyl)diphenol (compound 7) and (4,4-difluorobut-3-ene-1,2-diyl) bis(4,1-phenylene) diacetate (compound 7-Ac)

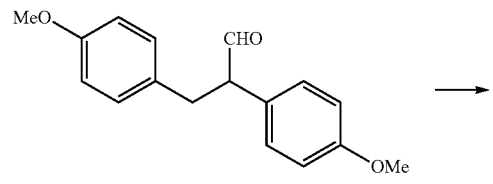

5b

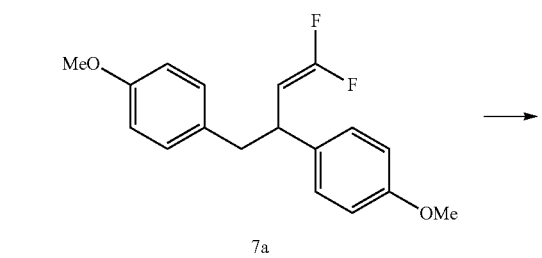

7a

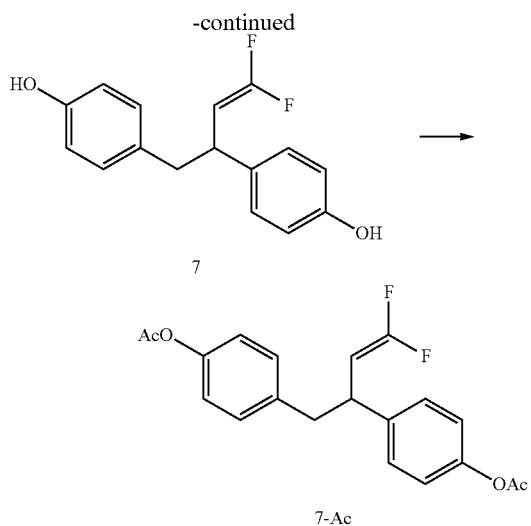

1) Synthesis of Compound 7a

THF (1 mL) was added at room temperature in an argon atmosphere. HCF$_2$P(O)(OEt)$_2$ (290 μL, 1.85 mmol) and LDA (1.62 mL, a 1.13 M solution in hexane, 1.83 mmol) were added thereto under a condition of −78° C., and the mixture was stirred for 2 hours. Then, compound 5b (70.7 mg, 0.262 mmol, 2.5 mL of a solution in THF) was added thereto, and the mixture was stirred overnight under reflux conditions. After confirmation of the completion of the reaction by TLC, the reaction solution was allowed to cool, and a saturated aqueous solution of ammonium chloride (30 mL) was added thereto under ice cooling, followed by extraction with ethyl acetate (20 mL) twice. Then, the organic layer was washed with saturated saline (30 mL) and dried over anhydrous magnesium sulfate. After filtration, the filtrate was concentrated, and the obtained crude product was purified by silica gel column chromatography (hexane/ethyl acetate) to obtain pale yellow solid 7a (55.7 mg, yield: 70%).

Melting point: 56-58° C.

$^1$H NMR (600 MHz, CDCl$_3$) δ 7.09-7.06 (m, 2H), 6.98-6.94 (m, 2H), 6.85-6.81 (m, 2H), 6.79-6.76 (m, 2H), 4.39 (ddd, J=24.8, 10.2, 2.7 Hz, 1H), 3.79 (s, 3H), 3.78 (s, 3H), 3.69-3.63 (m, 1H), 2.95 (dd, J=13.7, 6.7 Hz, 1H), 2.82 (dd, J=13.7, 8.4 Hz, 1H).

$^{13}$C NMR (150 MHz, CDCl$_3$): δ 158.2, 158.0, 155.8 (dd, J=287.3, 287.3 Hz), 135.5, 131.3, 130.1, 128.1, 113.9, 113.6, 82.0 (dd, J=20.1, 20.1 Hz), 55.3, 55.2, 42.7, 40.88, 40.86.

2) Synthesis of Compound 7

Compound 7a (23.3 mg, 0.0766 mmol) was subjected to the approach of step C of Production Example 1 to obtain colorless clear oil 7 (21.1 mg, yield: 100%).

Melting point: 108-110° C.

HRMS (ESI, negative mode) calc: 275.0889 [M−H]$^-$; found: 275.0885.

$^1$H NMR (600 MHz, DMSO-d$_6$): δ 8.17 (brs, 1H), 8.08 (brs, 1H), 7.12-7.08 (m, 2H), 7.00-6.96 (m, 2H), 6.78-6.75 (m, 2H), 6.73-6.69 (m, 2H), 4.66 (ddd, J=25.6, 10.5, 3.1 Hz, 1H), 3.67-3.60 (m, 1H), 2.92 (dd, J=13.5, 6.4, 0.8 Hz, 1H), 2.79 (m, 1H).

$^{13}$C NMR (150 MHz, DMSO-d$_6$): δ 156.9, 156.6, 156.5 (dd, J=286.0, 284.0 Hz), 154.6, 135.5, 131.3, 131.0, 129.0, 116.1, 115.8, 83.3 (dd, J=19.8, 19.8 Hz), 43.5, 42.11, 42.08.

3) Synthesis of Compound 7-Ac

To compound 7 (59.0 mg, 0.213 mmol), pyridine (0.86 mL) and acetic anhydride (0.65 mL) were added at room temperature in an argon atmosphere, and the mixture was stirred for 4 hours. After confirmation of the completion of the reaction by TLC, 4 N hydrochloric acid (1 mL) was added thereto under ice cooling, followed by extraction with ethyl acetate (20 mL) twice. Then, the organic layer was washed with saturated saline (20 mL) and dried over anhydrous magnesium sulfate. After filtration, the filtrate was concentrated and azeotroped with toluene. Then, the obtained crude product (91.2 mg) was purified by silica gel column chromatography (hexane/ethyl acetate) to obtain white solid 7-Ac (69.7 mg, yield: 91%).

Melting point: 79-80° C.

IR (ATR, cm$^{-1}$): 1759, 1743

$^1$H NMR (600 MHz, CDCl$_3$): δ 7.19-7.15 (m, 2H), 7.08-7.04 (m, 2H), 7.04-7.00 (m, 2H), 6.99-6.95 (m, 2H), 4.41 (ddd, J=24.5, 10.2, 2.5 Hz, 1H), 3.77-3.71 (m, 1H), 3.03 (dd, J=13.7, 6.4 Hz, 1H), 2.89 (dd, J=13.7, 8.7 Hz, 1H), 2.30 (s, 3H), 2.28 (s, 3H).

$^{13}$C NMR (150 MHz, CDCl$_3$): δ 169.5, 155.9 (dd, J=287.8, 287.8 Hz), 149.3, 149.1, 140.6, 136.4, 130.0, 128.1, 121.7, 121.3, 81.4 (dd, J=22.0, 19.8 Hz), 42.7, 40.9 (d, J=4.4 Hz), 21.2.

Production Example 5 Synthesis of 4,4'-(4-fluorobut-3-ene-1,2-diyl)diphenol (compound 8)

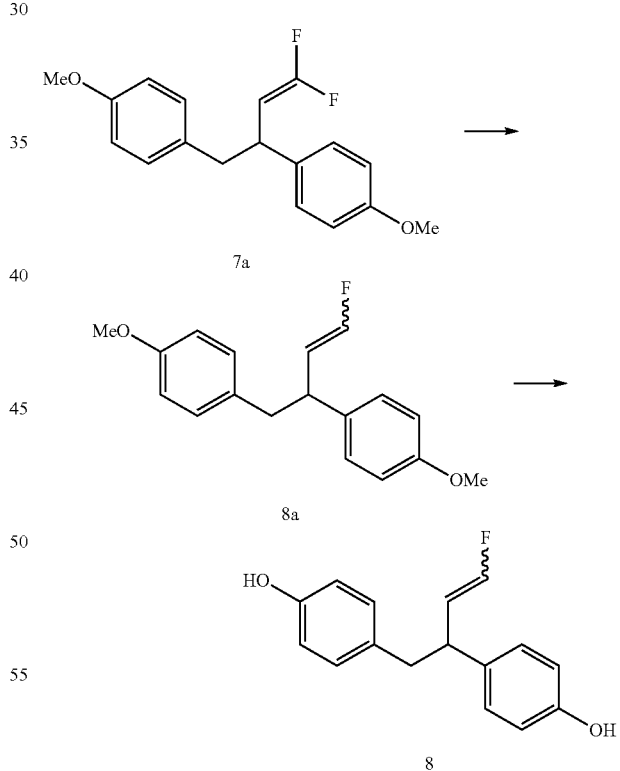

1) Synthesis of Compound 8a

To compound 7a (30.6 mg, 0.101 mmol), toluene (1 mL) and sodium bis(2-methoxyethoxy)aluminum hydride 85 μL, a 3.6 M solution in toluene, 0.306 mmol) (Tokyo Chemical Industry Co., Ltd.) were added at room temperature in an argon atmosphere, and the mixture was stirred overnight. Then, sodium bis(2-methoxyethoxy)aluminum hydride (175

μL, a 3.6 M solution in toluene, 0.630 mmol) was added thereto, and the mixture was stirred for 9 hours under reflux conditions. After confirmation of the completion of the reaction by TLC, the reaction solution was allowed to cool and adjusted to pH=4 by the addition of diethyl ether (3 mL) and 1 N hydrochloric acid (3 mL) under ice cooling.

Then, after extraction with hexane/diethyl ether (1/1) (10 mL) twice, the extract was washed with saturated saline (3 mL) and dried over anhydrous magnesium sulfate. After filtration, the filtrate was concentrated, and the obtained crude product (50.6 mg) was purified by silica gel column chromatography (hexane/ethyl acetate) to obtain pale yellow solid 8a (12.5 mg, yield: 43%, E/Z=1:4.8 ($^1$H NMR ratio))

(Z) Form $^1$H NMR (600 MHz, CDCl$_3$) δ 7.08-7.04 (m, 2H), 6.96-6.93 (m, 2H), 6.84-6.81 (m, 2H), 6.79-6.75 (m, 2H), 6.32 (ddd, J=85.1, 11.0, 1.0 Hz, 1H), 5.55 (ddd, J=19.5, 11.0, 8.2 Hz, 1H), 3.79 (s, 3H), 3.77 (s, 3H), 3.40-3.36 (m, 1H), 2.95 (dd, J=13.8, 6.9 Hz, 1H), 2.86 (dd, J=13.8, 8.0 Hz, 1H).

$^{13}$C NMR (150 MHz, CDCl$_3$): δ 158.2, 157.9, 149.2 (d, J=255.3 Hz), 135.4 (d, J=2.2 Hz), 131.6, 130.2, 128.4, 115.2 (d, J=9.4 Hz), 113.9, 113.6, 55.3, 55.2, 43.7 (d, J=8.8 Hz), 42.2.

(E) Form $^1$H NMR (600 MHz, CDCl$_3$): δ 7.13-7.09 (m, 2H), 7.00-6.97 (m, 2H), 6.84-6.81 (m, 2H), 6.79-6.75 (m, 2H), 6.40 (ddd, J=85.2, 4.7, 0.8 Hz, 1H), 4.95 (ddd, J=42.1, 10.0, 4.7 Hz, 1H), 4.07-4.02 (m, 1H), 3.78 (s, 3H), 3.77 (s, 3H), 2.96 (dd, J=13.7, 7.0 Hz, 1H), 2.85 (dd, J=13.7, 8.2 Hz, 1H).

$^{13}$C NMR (150 MHz, CDCl$_3$): δ 158.1, 157.9, 147.0 (d, J=258.3 Hz), 135.8, 131.7, 130.1, 128.3, 114.4 (d, J=5.2 Hz), 113.9, 113.5, 55.24, 55.18, 42.2, 40.6 (d, J=3.3 Hz).

2) Synthesis of Compound 8

Compound 8a (12.5 mg, 0.0437 mmol) was subjected to the approach of step C of Production Example 1 to obtain colorless clear oil 8 (8.9 mg, yield: 79%, E/Z=1:4.5 ($^1$H NMR ratio)).

HRMS (ESI, negative mode) calc: 257.0987 [M−H]$^-$; found: 257.0983

(Z) Form $^1$H NMR (600 MHz, DMSO-d$_6$) δ 8.12 (brs, 1H), 8.05 (brs, 1H), 7.08-7.03 (m, 2H), 6.95-6.90 (m, 2H), 6.77-6.72 (m, 2H), 6.71-6.66 (m, 2H), 6.52 (ddd, J=86.2, 11.0, 0.9 Hz, 1H), 5.60 (ddd, J=20.0, 11.0, 9.1 Hz, 1H), 3.47-3.41 (m, 1H), 2.92-2.76 (m, 1H), 2.87 (dd, J=13.4, 7.5 Hz, 1H).

$^{13}$C NMR (150 MHz, DMSO-d$_6$): δ 156.7, 156.5, 149.9 (d, J=253.1 Hz), 135.5 (d, J=2.2 Hz), 131.5, 131.0, 129.3, 116.7 (d, J=8.8 Hz), 116.0, 115.7, 44.4 (d, J=9.1 Hz), 43.0 (d, J=2.2 Hz).

(E) Form $^1$H NMR (600 MHz, DMSO-d$_6$): δ 8.12 (brs, 1H), 8.05 (brs, 1H), 7.09-7.06 (m, 2H), 6.96-6.94 (m, 2H), 6.77-6.72 (m, 2H), 6.71-6.66 (m, 2H), 6.58-6.42 (m, 1H), 5.10 (ddd, J=43.1, 10.2, 4.8 Hz, 1H), 4.01-3.95 (m, 1H), 2.90 (dd, J=13.4, 6.3 Hz, 1H), 2.92-2.76 (m, 1H).

$^{13}$C NMR (150 MHz, DMSO-d$_6$): δ 156.7, 156.5, 147.7 (d, J=255.3 Hz), 135.8 (d, J=1.9 Hz), 131.5, 130.9, 129.2, 116.0, 115.9 (d, J=4.7 Hz), 115.7, 43.3, 41.8 (d, J=3.6 Hz).

Production Example 6 Synthesis of 4,4'-(4,4,4-trifluoro-3-hydroxybutane-1,2-diyl)diphenol (compound 9)

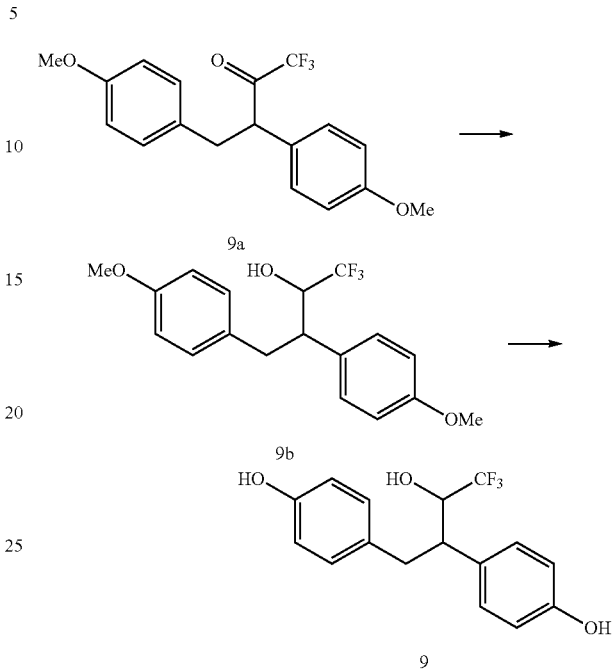

1) Compound 9a was synthesized according to the approach of the literature (Meyers et al., J. Med. Chem. 2001, 44, 4230-4251).

2) Synthesis of Compound 9b

To compound 9a (25.0 mg, 0.0806 mmol), methanol (1 mL) was added at room temperature in an argon atmosphere. Then, sodium borohydride (3.0 mg, 0.0806 mmol) was added thereto under ice cooling, and the mixture was stirred at room temperature for 4 hours. Then, sodium borohydride (3.0 mg, 0.0806 mmol) was further added thereto, and the mixture was stirred at room temperature for 1 hour. After confirmation of the completion of the reaction by TLC, a saturated aqueous solution of sodium bicarbonate (3 mL) was added thereto under ice cooling, followed by extraction with ethyl acetate (10 mL) twice. Then, the organic layer was washed with saturated saline (4 mL) and dried over anhydrous magnesium sulfate. After concentration of a filtrate, the obtained crude product (36.1 mg) was purified by silica gel column chromatography (hexane/ethyl acetate) to obtain pale yellow clear oil 9b (18.4 mg, yield: 67%).

$^1$H NMR (600 MHz, CDCl$_3$): δ 7.21-7.17 (m, 2H), 7.08-7.04 (m, 2H), 6.88-6.05 (m, 2H), 6.82-6.78 (m, 2H), 4.07-4.00 (m, 1H), 3.80 (s, 3H), 3.78 (s, 3H), 3.23 (ddd, J=9.0, 6.8, 3.2 Hz, 1H), 3.13 (dd, J=13.7, 9.0 Hz, 1H), 2.93 (dd, J=13.7, 6.8 Hz, 1H), 1.97 (d, J=8.8 Hz, 1H).

$^{13}$C NMR (150 MHz, CDCl$_3$): δ 159.0, 158.2, 131.0, 130.09, 130.06, 129.7, 125.0 (q, J=283.2 Hz), 114.00, 113.95, 71.2 (q, J=29.5 Hz), 55.2, 46.4, 37.9.

3) Synthesis of Compound 9

Compound 9b (18.4 mg, 0.0541 mmol) was subjected to the approach of step C of Production Example 1 to obtain colorless clear oil 9 (15.8 mg, yield: 94%).

$^1$H NMR (600 MHz, acetone-d$_6$): δ 8.08 (brs, 2H), 7.18-7.15 (m, 2H), 7.02-6.98 (m, 2H), 6.72-6.68 (m, 4H), 5.31 (d, J=6.6 Hz, 1H), 4.22-4.15 (m, 1H), 3.13-3.08 (m, 2H), 2.90-2.84 (m, 1H).

$^{13}$C NMR (150 MHz, acetone-d6): δ 157.0, 156.6, 131.6, 131.4, 131.3, 131.0, 126.8 (q, J=283.5 Hz), 115.9, 115.4, 71.7 (q, J=28.7 Hz), 47.8, 39.5.

Production Example 7 Synthesis of N-(1,2-bis(4-hydroxyphenyl)ethyl)-2,2,2-trifluoroacetamide (compound 10)

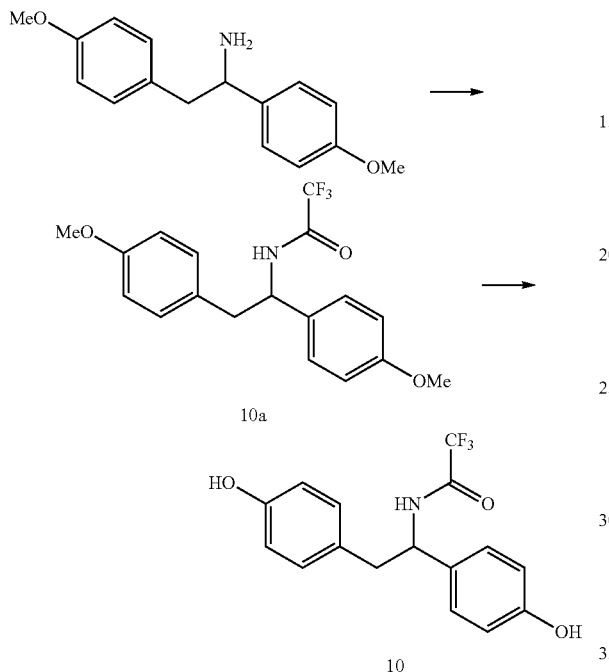

1) Synthesis of Compound 10a

To 1,2-bis(4-methoxyphenyl)ethan-1-amine (271.1 mg, 1.05 mmol), dichloromethane (9.8 mL) was added at room temperature in an argon atmosphere. Pyridine (1.7 mL, 21.1 mmol) and trifluoroacetic anhydride (1.5 mL, 10.6 mmol) were added thereto under ice cooling, and the mixture was stirred at room temperature for 3 hours. After confirmation of the completion of the reaction by TLC, water (5 mL) was added thereto under ice cooling, followed by extraction with chloroform (50 mL) twice. Then, the organic layer was washed with saturated saline (30 mL) and dried over anhydrous magnesium sulfate. After filtration, the filtrate was concentrated, and the obtained crude product was purified by silica gel column chromatography (hexane/ethyl acetate) to obtain white solid 10a (167.2 mg, yield: 45%).

Melting point: 101-103° C.

$^1$H NMR (600 MHz, CDCl3): δ 7.14-7.10 (m, 2H), 6.96-6.92 (m, 2H), 6.88-6.84 (m, 2H), 6.79-6.76 (m, 2H), 6.44 (d, J=7.3 Hz, 1H), 5.15 (ddd, J=14.8, 7.2, 7.1 Hz, 1H), 3.80 (s, 3H), 3.77 (s, 3H), 3.11 (dd, J=14.3, 7.1 Hz, 1H), 3.09 (dd, J=14.3, 7.2 Hz, 1H).

$^{13}$C NMR (150 MHz, CDCl3): δ 159.3, 158.6, 156.3 (q, J=37.0 Hz), 131.3, 130.3, 128.1, 127.8, 115.8 (q, J=288.3 Hz), 114.2, 114.0, 55.3, 55.2, 54.9, 41.0.

2) Synthesis of Compound 10

Compound 10a (88.0 mg, 0.249 mmol) was subjected to the approach of step C of Production Example 1 to obtain white solid 10 (69.0 mg, yield: 85%).

Melting point: 184-186° C.

HRMS (ESI, negative mode) calc: 324.0853 [M−H]−; found: 324.0856.

$^1$H NMR (600 MHz, CD3OD): δ 7.16-7.13 (m, 2H), 7.00-6.96 (m, 2H), 6.75-6.72 (m, 2H), 6.67-6.64 (m, 2H), 5.02 (t, J=7.9 Hz, 1H), 3.00 (d, J=7.9 Hz, 2H).

$^{13}$C NMR (150 MHz, CD3OD): δ 158.14 (q, J=36.8 Hz), 158.06, 157.1, 133.1, 131.2, 130.1, 129.1, 117.6 (q, J=286.8 Hz), 116.3, 116.1, 56.9, 41.9.

Production Example 8 Synthesis of 4,4'-(1-(azetidin-1-yl)ethane-1,2-diyl)diphenol (compound 11)

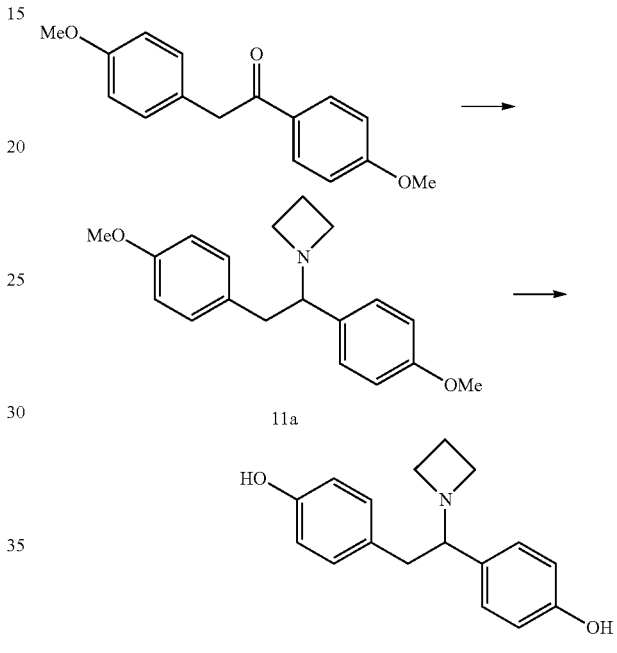

1) Synthesis of Compound 11a

To deoxyanisoin (331.0 mg, 1.29 mmol), methanol/acetic acid (15.0 mL/1.5 mL), azetidine (130 μL, 1.93 mmol), and 2-picoline borane (207.6 mg, 1.94 mmol) were added at room temperature in an argon atmosphere, and the mixture was stirred overnight. Then, the reaction mixture was further stirred overnight under reflux. After confirmation of the completion of the reaction by TLC, 1 N hydrochloric acid (20 mL) was added thereto, and the mixture was separated into organic and aqueous layers with ethyl acetate (20 mL). To the aqueous layer, a 1 N aqueous sodium hydroxide solution (50 mL) was added, and the mixture was stirred at room temperature. Then, after extraction with ethyl acetate (50 mL) three times, the extract was dried over anhydrous magnesium sulfate. After filtration, the filtrate was concentrated, and the obtained crude product (292.5 mg) was purified by silica gel column chromatography (chloroform/methanol) to obtain pale yellow clear oil 11a (173.1 mg, yield: 45%).

$^1$H NMR (600 MHz, CDCl3) δ 7.04-6.98 (m, 2H), 6.80-6.73 (m, 4H), 6.70-6.66 (m, 2H), 3.77 (s, 3H), 3.74 (s, 3H), 3.26-3.14 (m, 3H), 3.09-3.02 (m, 2H), 2.92 (dd, J=13.2, 4.2 Hz, 1H), 2.60 (dd, J=13.2, 9.4 Hz, 1H), 2.06-1.96 (m, 2H).

$^{13}$C NMR (150 MHz, CDCl3): δ 158.6, 157.7, 132.7, 130.9, 130.5, 129.2, 113.32, 113.29, 75.9, 55.1, 54.2, 40.6, 16.8.

2) Synthesis of Compound 11

Compound 11a (86.3 mg, 0.290 mmol) was subjected to the approach of step C of Production Example 1 to obtain white solid 11 (63.2 mg, yield: 81%).

Melting point: 230-232° C. (decomposition)

HRMS (ESI, positive mode) calc: 270.1489 [M+H]$^+$; found: 270.1494.

$^1$H NMR (600 MHz, CD$_3$OD): δ 7.11-7.05 (m, 2H), 6.86-6.82 (m, 2H), 6.76-6.73 (m, 2H), 6.63-6.59 (m, 2H), 4.01 (brs, 1H), 3.80-3.65 (m, 2H), 3.65-3.50 (m, 2H), 3.06 (dd, J=13.5, 5.5 Hz, 1H), 2.83 (dd, J=13.5, 9.6 Hz, 1H), 2.30-2.22 (m, 2H).

$^{13}$C NMR (150 MHz, CD$_3$OD): δ 159.3, 157.4, 131.5, 130.7, 128.4, 127.2, 116.7, 116.2, 74.1, 55.1, 39.0, 17.1.

Production Example 9 Synthesis of 4,4'-(1-(1H-pyrazol-5-yl)ethane-1,2-diyl)diphenol (compound 12)

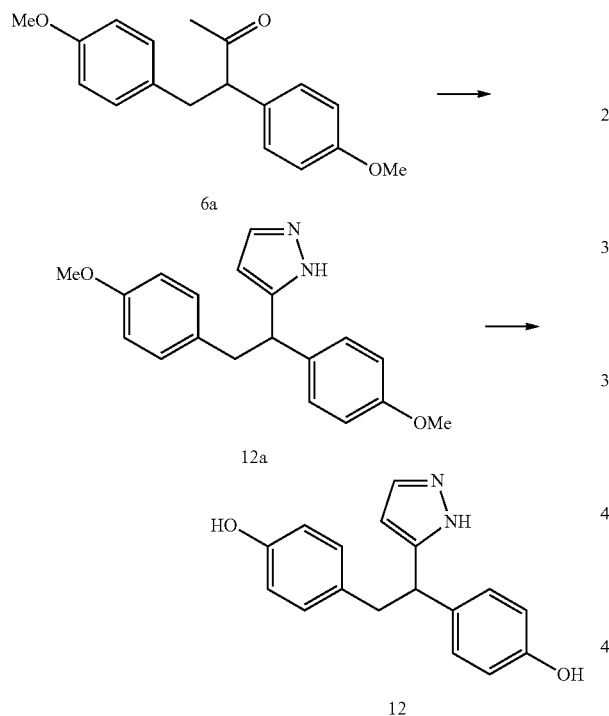

1) Synthesis of Compound 12a

To compound 6a (387.8 mg, 1.36 mmol), dimethylformamide (hereinafter, abbreviated to DMF) (7.8 mL) and DMF-dimethylacetal (1.8 mL, 13.6 mmol) were added at room temperature in an argon atmosphere, and the mixture was stirred overnight at 110° C. After confirmation of the completion of the reaction by TLC, the reaction solution was concentrated. To the obtained crude product (514.0 mg), ethanol (9.8 mL) and hydrazine monohydrochloride (286.8 mg, 4.19 mmol) were added at room temperature in an argon atmosphere, and the mixture was stirred overnight under reflux. After confirmation of the completion of the reaction by TLC, the reaction solution was concentrated. The obtained crude product (824.1 mg) was purified by silica gel column chromatography (hexane/ethyl acetate) to obtain pale yellow oil 12a (335.4 mg, yield: 88%).

HRMS (ESI, positive mode) calc: 309.1598 [M+H]$^+$; found: 309.1582.

$^1$H NMR (600 MHz, CDCl$_3$): δ 7.46 (d, J=1.9 Hz, 1H), 7.12-7.07 (m, 2H), 6.96-6.92 (m, 2H), 6.82-6.79 (m, 2H), 6.75-6.71 (m, 2H), 6.11 (d, J=1.9 Hz, 1H), 4.21 (dd, J=7.8 Hz, 1H), 3.77 (s, 3H), 3.75 (s, 3H), 3.36 (dd, J=13.7, 7.3 Hz, 1H), 3.15 (dd, J=13.7, 8.3 Hz, 1H).

$^{13}$C NMR (150 MHz, CDCl$_3$): δ 158.3, 157.9, 134.6, 131.8, 130.0, 129.0, 113.8, 113.5, 103.7, 55.2, 55.2, 45.5, 41.4.

2) Synthesis of Compound 12

Compound 12a (80.1 mg, 0.260 mmol) was subjected to the approach of step C of Production Example 1 to obtain colorless clear oil 12 (20.6 mg, yield: 28%).

HRMS (ESI, negative mode) calc: 279.1139 [M−H]$^-$; found: 279.1139.

$^1$H NMR (600 MHz, CD$_3$OD): δ 7.45 (s, 1H), 7.02-6.95 (m, 2H), 6.85-6.80 (m, 2H), 6.67-6.62 (m, 2H), 6.58-6.54 (m, 2H), 6.18 (s, 1H), 4.14 (dd, J=8.3, 7.6 Hz, 1H), 3.25 (dd, J=13.6, 7.6 Hz, 1H), 3.07 (dd, J=13.6, 8.3 Hz, 1H).

$^{13}$C NMR (150 MHz, CD$_3$OD): δ 156.9, 156.5, 152.8, 135.6, 132.3, 131.1, 130.0, 116.0, 115.8, 104.2, 49.9, 47.1, 42.8.

Production Example 10 Synthesis of 4,4'-(1-(oxazol-5-yl)ethane-1,2-diyl)diphenol (compound 13)

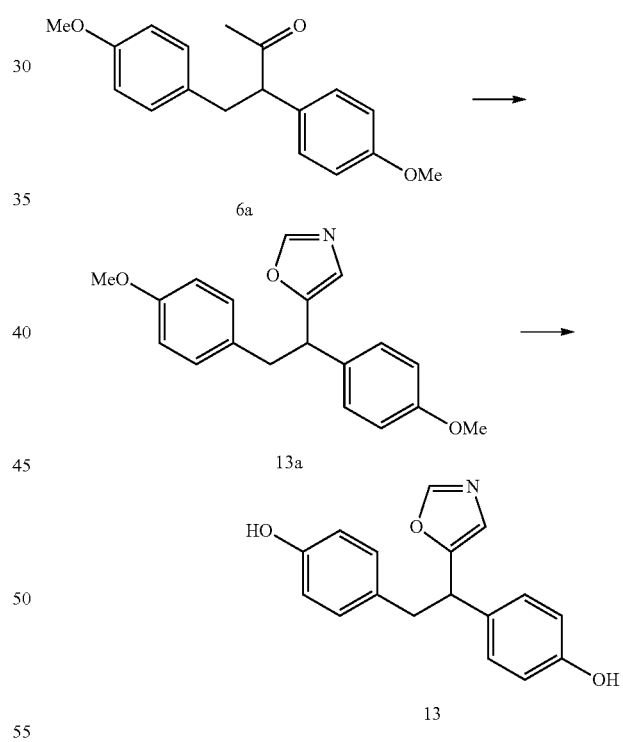

1) Synthesis of Compound 13a

To compound 6a (182.6 mg, 0.642 mmol), dimethyl sulfoxide (3.8 mL) and I$_2$ (182.6 mg, 0.719 mmol) were added at room temperature in an argon atmosphere, and the mixture was stirred at room temperature for 1 hour and then stirred at 110° C. for 1 hour. Then, glycine (97.0 mg, 1.29 mmol) was added thereto, and the mixture was stirred at 110° C. for 1.5 hours. After confirmation of the completion of the reaction by TLC, the reaction solution was allowed to cool, and water (30 mL) was added thereto, followed by extraction with ethyl acetate (70 mL) three times. The organic layer was reduced with a saturated aqueous solution of sodium thiosulfate (30 mL), washed with saturated saline (50 mL), and dried over anhydrous magnesium sulfate. After filtration, the filtrate was concentrated, and the obtained crude product (217.8 mg) was purified by silica gel column chromatography (hexane/ethyl acetate) to obtain purple-brown oil 13a (32.1 mg, yield: 16%).

HRMS (ESI, positive mode) calc: 310.1438 [M+H]$^+$; found: 310.1426.

$^1$H NMR (600 MHz, CDCl$_3$) δ 7.78 (s, 1H), 7.10-7.06 (m, 2H), 6.92-6.88 (m, 2H), 6.84-6.80 (m, 2H), 6.77 (s, 1H), 6.75-6.72 (m, 2H), 4.16 (dd, J=8.3, 7.3 Hz, 1H), 3.78 (s, 3H), 3.75 (s, 3H), 3.32 (dd, J=13.7, 7.3 Hz, 1H), 3.09 (dd, J=13.7, 8.3 Hz, 1H).

$^{13}$C NMR (150 MHz, CDCl$_3$): δ 158.5, 158.0, 154.6, 150.4, 132.6, 130.9, 129.9, 128.9, 122.6, 113.9, 113.6, 55.23, 55.16, 44.7, 40.2.

2) Synthesis of Compound 13

Compound 13a (21.9 mg, 0.0708 mmol) was subjected to the approach of step C of Production Example 1 to obtain yellow-brown oil 13 (15.5 mg, yield: 78%).

HRMS (ESI, negative mode) calc: 280.0979 [M−H]$^-$; found: 280.0981.

$^1$H NMR (600 MHz, CD$_3$OD): δ 8.07 (s, 1H), 7.04-7.00 (m, 2H), 6.86-6.83 (m, 2H), 6.80 (s, 1H), 6.70-6.66 (m, 2H), 6.60-6.57 (m, 2H), 4.17 (dd, J=8.1, 7.7 Hz, 1H), 3.25 (dd, J=13.7, 7.7 Hz, 1H), 3.04 (dd, J=13.7, 8.1 Hz, 1H).

$^{13}$C NMR (150 MHz, CD$_3$OD): δ 157.5, 157.1, 156.8, 152.5, 133.0, 131.3, 131.1, 130.1, 122.7, 116.2, 115.9, 46.0, 41.3.

Production Example 11 Synthesis of 4,4'-(1-(1,2,4-oxadiazol-3-yl)ethane-1,2-diyl)diphenol (compound 14)

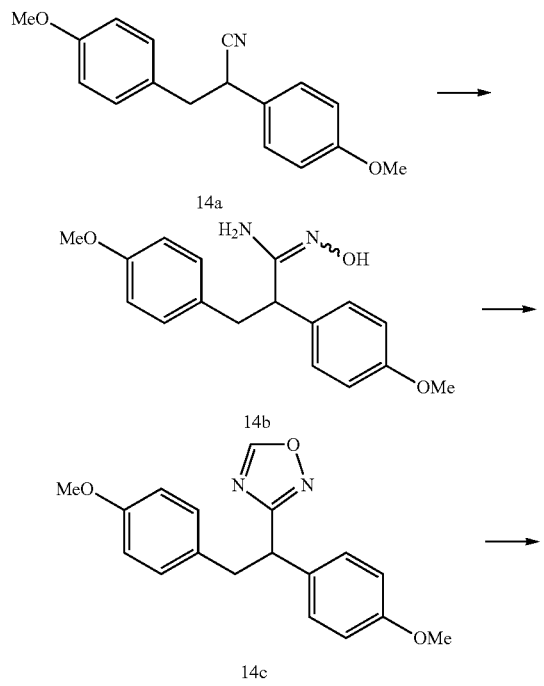

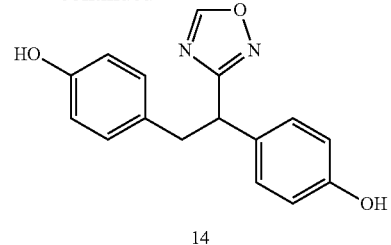

1) Compound 14a was synthesized according to the approach of the literature (Meyers et al., J. Med. Chem. 2001, 44, 4230-4251).

2) Synthesis of Compound 14b

Potassium carbonate (155.5 mg, 1.13 mmol), water (1.0 mL), and hydroxylamine hydrochloride (78.3 mg, 1.13 mmol) were added at room temperature in an argon atmosphere, and the mixture was stirred for 30 minutes. Then, compound 14a (299.4 mg, 1.12 mmol, in ethanol, 3.5 mL) was added thereto, and the mixture was stirred overnight under reflux. Then, hydroxylamine hydrochloride (82.5 mg, 1.19 mmol) and potassium carbonate (154.3 mg, 1.12 mmol) were added thereto, and the mixture was further stirred overnight. After confirmation of the completion of the reaction by TLC, the reaction solution was allowed to cool and filtered. After concentration of the filtrate, the obtained crude product (291.7 mg) was purified by silica gel column chromatography (hexane/ethyl acetate) to obtain pale yellow clear oil 14b (45.1 mg, yield: 13%).

HRMS (ESI, positive mode) calc 301.1547 [M+H]$^1$; found: 301.1532.

$^1$H NMR (600 MHz, CDCl$_3$) δ 7.15-7.11 (m, 2H), 6.96-6.92 (m, 2H), 6.84-6.80 (m, 2H), 6.75-6.72 (m, 2H), 4.36 (brs, 2H), 3.78 (s, 3H), 3.75 (s, 3H), 3.57 (dd, J=8.8, 6.6 Hz, 1H), 3.31 (dd, J=13.8, 6.6 Hz, 1H), 2.94 (dd, J=13.8, 8.8 Hz, 1H).

$^{13}$C NMR (150 MHz, CDCl$_3$): δ 158.7, 157.9, 155.5, 131.8, 131.5, 130.0, 129.1, 114.0, 113.5, 55.2, 55.1, 49.3, 37.6.

3) Synthesis of Compound 14c

To compound 14b (27.3 mg, 0.0909 mmol), DMF (0.3 mL), trimethyl orthoformate (0.2 mL, 1.09 mmol), and a boron trifluoride-diethyl ether complex (1 drop (approximately 1 μL)) were added at room temperature in an argon atmosphere, and the mixture was stirred overnight. After confirmation of the completion of the reaction by TLC, the reaction solution was concentrated, and the obtained crude product (40.1 mg) was purified by silica gel column chromatography (hexane/ethyl acetate) to obtain white solid 14c (11.5 mg, yield: 42%).

Melting point: 79-81° C.

HRMS (ESI, positive mode) calc: 311.1390 [M+H]$^+$; found: 311.1397.

$^1$H NMR (600 MHz, CDCl$_3$): δ 8.59 (s, 1H), 7.28-7.25 (m, 2H), 7.00-6.96 (m, 2H), 6.85-6.82 (m, 2H), 6.75-6.72 (m, 2H), 4.40 (dd, J=8.3, 7.6 Hz, 1H), 3.78 (s, 3H), 3.75 (s, 3H), 3.46 (dd, J=13.9, 8.3 Hz, 1H), 3.24 (dd, J=13.9, 7.6 Hz, 1H).

$^{13}$C NMR (150 MHz, CDCl$_3$): δ 171.3, 164.5, 158.7, 158.1, 131.6, 130.7, 130.0, 129.1, 114.0, 113.7, 55.2, 55.1, 44.6, 39.7.

4) Synthesis of Compound 14

Compound 14c (8.0 mg, 0.0258 mmol) was subjected to the approach of step C of Production Example 1 to obtain white solid 14 (7.8 mg, yield: quant.).

Melting point: 163-164° C.

HRMS (ESI, positive mode) calc: 283.1077 [M+H]+; found: 283.1083.

$^1$H NMR (600 MHz, CD$_3$OD): δ 9.09 (s, 1H), 7.15-7.11 (m, 2H), 6.90-6.86 (m, 2H), 6.70-6.67 (m, 2H), 6.60-6.57 (m, 2H), 4.31 (dd, J=8.7, 7.4 Hz, 1H), 3.34 (dd, J=13.7, 8.7 Hz, 1H), 3.13 (dd, J=13.7, 7.4 Hz, 1H).

$^{13}$C NMR (150 MHz, CD$_3$OD): δ172.5, 167.2, 157.7, 156.9, 132.2, 131.15, 131.11, 130.2, 116.3, 116.0, 46.2, 41.2.

Production Example 12 Synthesis of 4,4'-(1-(4H-1,2,4-triazol-3-yl)ethane-1,2-diyl)diphenol (compound 15)

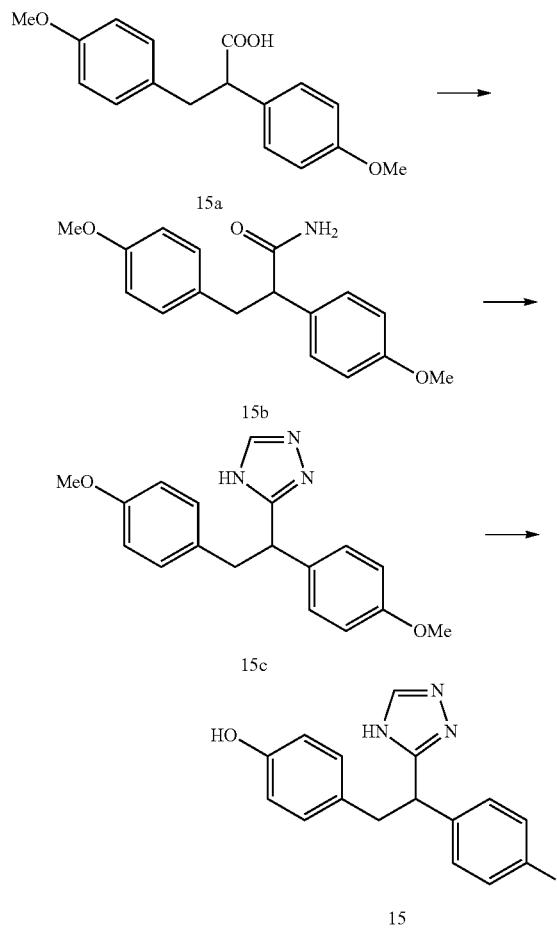

1) Compound 15a was synthesized according to the approach of the literature (Meyers et al., J. Med. Chem. 2001, 44, 4230-4251).

2) Synthesis of Compound 15b

To compound 15a (506.9 mg, 1.77 mmol), DMF (15 mL) was added at room temperature in an argon atmosphere. 1-Hydroxybenzotriazole (264.1 mg, 1.95 mmol) and 1-ethyl-3-(3-dimethylaminopropyl)carbodiimide hydrochloride (376.2 mg, 1.96 mmol) were added thereto under ice cooling, and the mixture was stirred for 10 minutes. Then, an aqueous solution of 25% by mass of ammonia (5.1 mL) was added thereto, and the mixture was stirred overnight at room temperature. After confirmation of the completion of the reaction by TLC, the reaction solution was added to water (30 mL), followed by extraction with hexane/ethyl acetate (1/1) (50 mL) three times. Then, the organic layer was washed with saturated saline (50 mL) and dried over anhydrous magnesium sulfate. After filtration, the filtrate was concentrated, and the obtained crude product (150 mg) was purified by silica gel column chromatography (chloroform/methanol) to obtain white solid 15b (58.9 mg, yield: 12%).

Melting point: 190-191° C.

IR (ATR, cm$^{-1}$): 1672

HRMS (ESI, positive mode) calc: 286.1438 [M+H]+; found: 286.1449.

$^1$H NMR (600 MHz, DMSO-d$_6$): δ 7.35 (d, J=1.7 Hz, 1H), 7.27-7.23 (m, 2H), 7.08-7.04 (m, 2H), 6.86-6.82 (m, 2H), 6.80-6.76 (m, 2H), 6.72 (d, J=1.7 Hz, 1H), 3.71 (s, 3H), 3.69 (s, 3H), 3.62 (dd, J=9.0, 6.3 Hz, 1H), 3.17 (dd, J=13.6, 9.0 Hz, 1H), 2.72 (dd, J=13.6, 6.3 Hz, 1H).

$^{13}$C NMR (150 MHz, DMSO-d$_6$): δ 174.3, 157.8, 157.3, 132.7, 131.8, 129.6, 128.6, 113.4, 113.3, 54.9, 54.8, 52.1, 37.8.

3) Synthesis of Compound 15c

To compound 15b (48.7 mg, 0.171 mmol), DMF-dimethylacetal (1.5 mL) was added at room temperature in an argon atmosphere, and the mixture was stirred at 120° C. for 1 hour and then allowed to cool. Then, the reaction solution was concentrated. To the obtained crude product (48.7 mg), acetic acid (1.2 mL) and hydrazine monohydrate (10.5 L, 0.216 mmol) were added at room temperature in an argon atmosphere, and the mixture was stirred at 90° C. for 1.5 hours. After confirmation of the completion of the reaction by TLC, the reaction solution was allowed to cool and concentrated. To the obtained crude product (145.3 mg), a saturated aqueous solution of sodium bicarbonate (20 mL) was added, followed by extraction with ethyl acetate (25 mL) three times. Then, the extract was washed with saturated saline (20 mL) and dried over anhydrous magnesium sulfate. After filtration, the filtrate was concentrated, and the obtained crude product (47.1 mg) was purified by silica gel column chromatography (hexane/ethyl acetate) to obtain white solid 15c (29.2 mg, yield: 55%).

Melting point: 136-138° C.

HRMS (ESI, positive mode) calc: 310.1550 [M+H]+; found: 310.1556.

$^1$H NMR (600 MHz, CDCl$_3$): δ 10.32 (brs, 1H), 8.01 (s, 1H), 7.21-7.17 (m, 2H), 6.96-6.92 (m, 2H), 6.85-6.82 (m, 2H), 6.74-6.71 (m, 2H), 4.28 (dd, J=8.2, 7.4 Hz, 1H), 3.78 (s, 3H), 3.74 (s, 3H), 3.56 (dd, J=13.9, 7.4 Hz, 1H), 3.20 (dd, J=13.9, 8.2 Hz, 1H).

$^{13}$C NMR (150 MHz, CDCl$_3$): δ 161.5, 158.7, 158.0, 148.9, 132.2, 131.1, 130.0, 129.2, 114.1, 113.6, 55.3, 55.1, 45.9, 40.6.

4) Synthesis of Compound 15

Compound 15c (27.2 mg, 0.0879 mmol) was subjected to the approach of step C of Production Example 1 to obtain white solid 15 (19.7 mg, yield: 80%).

Melting point: 246-248° C. (decomposition)

HRMS (ESI, negative mode) calc: 280.1092 [M−H]−; found: 280.1092.

$^1$H NMR (600 MHz, CD$_3$OD): δ 7.99 (brs, 1H), 7.11-7.07 (m, 2H), 6.87-6.84 (m, 2H), 6.70-6.66 (m, 2H), 6.59-6.55 (m, 2H), 4.27 (dd, J=9.0, 7.2 Hz, 1H), 3.36 (dd, J=13.7, 9.0 Hz, 1H), 3.14 (dd, J=13.7, 7.2 Hz, 1H).

$^{13}$C NMR (150 MHz, CD$_3$OD) δ 160.7, 157.5, 156.8, 151.5, 133.2, 131.5, 131.0, 129.9, 116.3, 115.9, 47.2, 41.7.

Production Example 13 Synthesis of 4,4'-(1-(oxa-zol-4-yl)ethane-1,2-diyl)diphenol (compound 16)

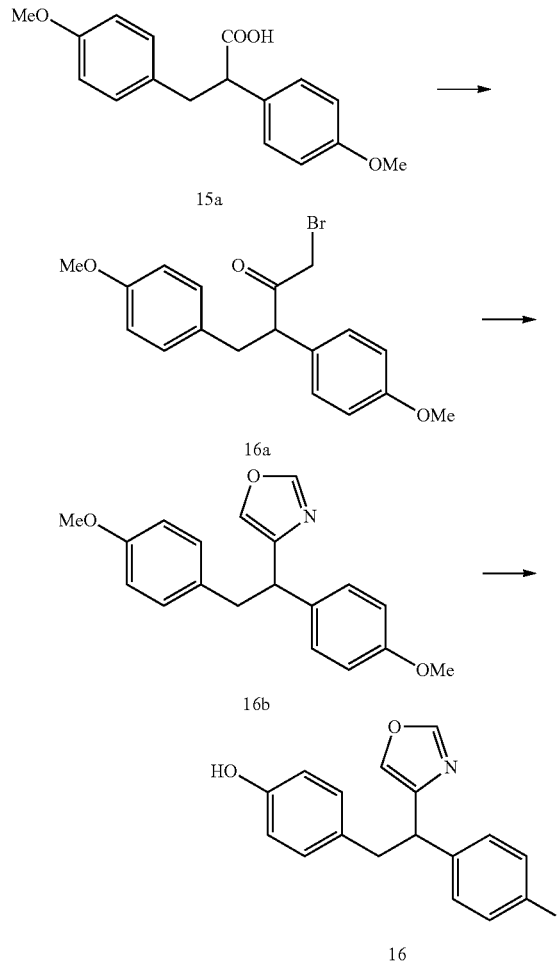

1) Synthesis of Compound 16a

To compound 15a (294.2 mg, 1.03 mmol), dichloromethane (6.6 mL) was added at room temperature in an argon atmosphere. DMF (6 μL) and oxalyl chloride (0.20 mL, 2.33 mmol) were added thereto under ice cooling, and the mixture was stirred at room temperature for 1.5 hours. Then, the reaction solution was concentrated. To the obtained crude product (340.2 mg), THF (6.2 mL) and trimethylsilyldiazomethane (1.50 mL, 3.00 mmol, a 2 M solution in diethyl ether) were added at room temperature in an argon atmosphere, and the mixture was stirred for 2 hours. Then, the reaction solution was concentrated. To the obtained crude product (394.3 mg), diethyl ether (3.8 mL) was added at room temperature in an argon atmosphere, then 48% by mass of hydrobromic acid (0.12 mL) was added under ice cooling, and the mixture was stirred for 1 hour. After confirmation of the completion of the reaction by TLC, a saturated aqueous solution of sodium bicarbonate (7 mL) was added, followed by extraction with ethyl acetate (50 mL) twice. Then, the organic layer was washed with saturated saline (30 mL) and dried over anhydrous magnesium sulfate. After filtration, the filtrate was concentrated, and the obtained crude product (395.9 mg) was purified by silica gel column chromatography (hexane/ethyl acetate) to obtain pale yellow solid 16a (258.8 mg, yield: 83%).

Melting point: 78-79° C.
IR (ATR, cm$^{-1}$): 1729
$^1$H NMR (600 MHz, CDCl$_3$): δ 7.12-7.08 (m, 2H), 6.98-6.94 (m, 2H), 6.86-6.83 (m, 2H), 6.77-6.73 (m, 2H), 4.17 (dd, J=7.5, 7.2 Hz, 1H), 3.81 (d, J=12.9 Hz, 1H), 3.79 (s, 3H), 3.76 (s, 3H), 3.72 (d, J=12.9 Hz, 1H), 3.33 (dd, J=13.9, 7.5 Hz, 1H), 2.88 (dd, J=13.9, 7.2 Hz, 1H).
$^{13}$C NMR (150 MHz, CDCl$_3$): δ 201.0, 159.1, 158.0, 131.0, 130.0, 129.5, 129.3, 114.5, 113.7, 57.2, 55.3, 55.2, 38.1, 34.2.

2) Synthesis of Compound 16b

To compound 16a (118.6 mg, 0.326 mmol), formamide (0.36 mL) was added at room temperature in an argon atmosphere, and the mixture was stirred at 110° C. for 1 hour. After confirmation of the completion of the reaction by TLC, the reaction solution was allowed to cool. Then, water (10 mL) was added thereto, followed by extraction with ethyl acetate (20 mL) three times. Then, the organic layer was washed with saturated saline (15 mL) and dried over anhydrous magnesium sulfate. After filtration, the filtrate was concentrated. Then, the obtained crude product (143.5 mg) was purified by silica gel column chromatography (hexane/ethyl acetate) to obtain pale yellow clear oil 16b (11.1 mg, yield: 11%).

$^1$H NMR (600 MHz, CDCl$_3$): δ 7.83 (d, J=0.4 Hz, 1H), 7.28 (dd, J=0.4, 0.9 Hz, 1H), 7.18-7.15 (m, 2H), 6.95-6.91 (m, 2H), 6.83-6.80 (m, 2H), 6.74-6.70 (m, 2H), 4.05 (dd, J=8.3, 7.2 Hz, 1H), 3.77 (s, 3H), 3.75 (s, 3H), 3.38 (dd, J=13.7, 7.2 Hz, 1H), 3.09 (dd, J=13.7, 8.3 Hz, 1H).
$^{13}$C NMR (150 MHz, CDCl$_3$): δ 158.3, 157.8, 151.0, 143.3, 134.8, 134.3, 131.9, 130.0, 129.1, 113.8, 113.5, 55.24, 55.17, 44.9, 40.6.

3) Synthesis of Compound 16

Compound 16b (7.4 mg, 0.0239 mmol) was subjected to the approach of step C of Production Example 1 to obtain white solid 16 (7.4 mg, yield: quant.).
Melting point: 228-229° C. (decomposition)
HRMS (ESI, negative mode) calc: 280.0979 [M−H]$^+$; found: 280.0982.
$^1$H NMR (600 MHz, CD$_3$OD) δ 8.11 (d, J=0.7 Hz, 1H), 7.59 (dd, J=0.7, 0.9 Hz, 1H), 7.04-7.00 (m, 2H), 6.86-6.82 (m, 2H), 6.68-6.64 (m, 2H), 6.59-6.55 (m, 2H), 4.00 (dd, J=8.4, 7.2 Hz, 1H), 3.26 (dd, J=13.6, 7.2 Hz, 1H), 3.00 (dd, J=13.6, 8.4 Hz, 1H).
$^{13}$C NMR (150 MHz, CD$_3$OD): δ 157.1, 156.6, 153.3, 144.5, 136.8, 134.5, 132.1, 131.1, 130.2, 116.1, 115.8, 46.3, 41.8.

Production Example 14 Synthesis of 4,4'-(4,4-difluorobut-3-ene-1,2-diyl)bis(3-fluorophenol) (compound 17-F), 4,4'-(4,4-dichlorobut-3-ene-1,2-diyl) bis(3-fluorophenol) (compound 17-Cl), 4-(4,4-difluoro-2-(4-hydroxyphenyl)but-3-en-1-yl)-3,5 (compound 18-F), and 4-(4,4-dichloro-2-(4-hydroxyphenyl)but-3-en-1-yl)-3,5-difluorophenol (compound 18-Cl)

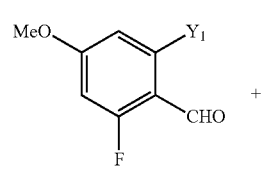

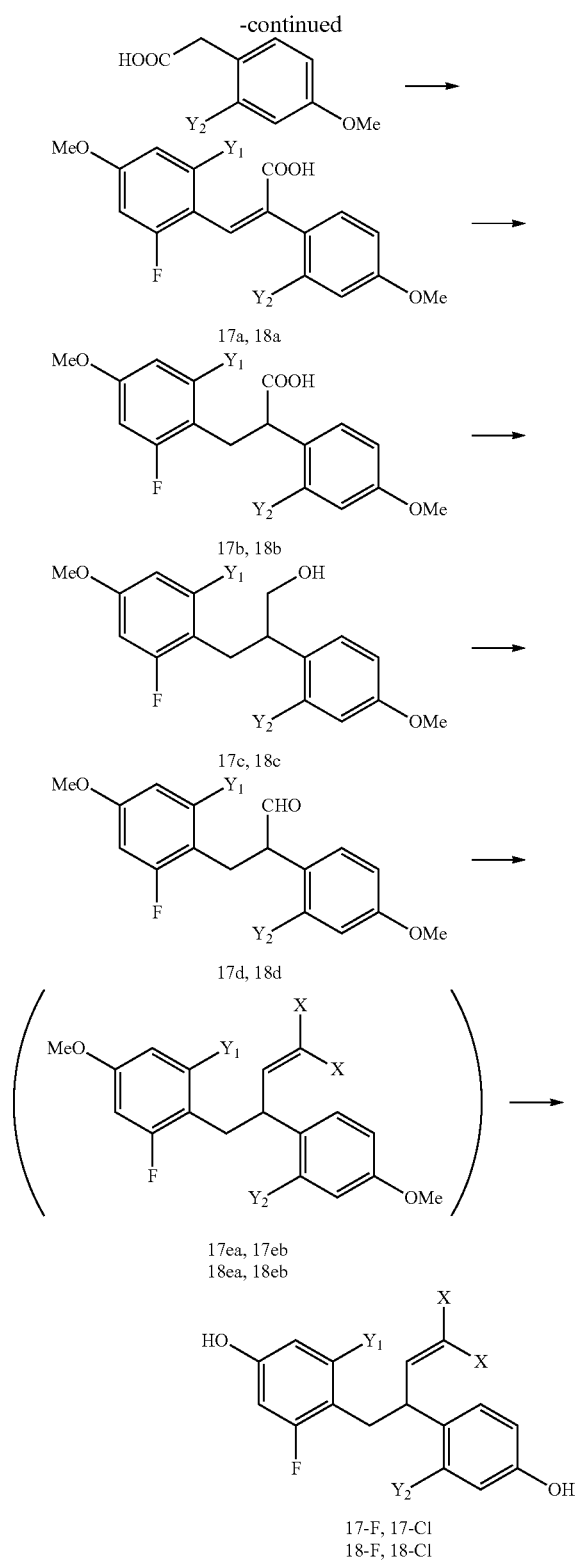

1) Synthesis of Compound 17a ($Y_1$=H, $Y_2$=F)

To 2-fluoro-4-methoxybenzaldehyde (3.39 g, 22.0 mmol), 2-fluoro-4-methoxyphenylacetic acid (3.99 g, 21.7 mmol), acetic anhydride (8.0 mL), and triethylamine (3.6 mL, 26.1 mmol) were added at room temperature in an argon atmosphere, and the mixture was stirred for 4 hours under reflux. After confirmation of the completion of the reaction by TLC, the reaction solution was allowed to cool, neutralized with a 3 N aqueous sodium hydroxide solution (90 mL) under ice cooling, and subsequently adjusted to pH 4 with 4 N hydrochloric acid (150 mL). After extraction with ethyl acetate three times, the organic layer was washed with water and saturated saline and dried over anhydrous magnesium sulfate. After filtration, the filtrate was concentrated, and the obtained crude product (891 mg) was recrystallized from hexane/ethyl acetate to obtain white solid 17a (3.29 g, yield: 47%).

Melting point: 188-191° C.

$^1$H NMR (600 MHz, CDCl$_3$): δ 8.17 (s, 1H), 7.07 (dd, J=8.4, 8.3 Hz, 1H), 6.80 (dd, J=8.9, 8.7 Hz, 1H), 6.70 (dd, J=8.3, 5.6 Hz, 1H), 6.68 (dd, J=11.4, 9.0 Hz, 1H), 6.59 (dd, J=12.1, 2.5 Hz, 1H), 6.42 (dd, J=8.9, 2.5 Hz, 1H), 3.82 (s, 3H), 3.76 (s, 3H).

$^{13}$C NMR (150 MHz, CDCl$_3$): δ 172.0, 162.6 (d, J=253.4 Hz), 162.3 (d, J=12.1 Hz), 161.2 (d, J=10.7 Hz), 160.9 (d, J=247.6 Hz), 135.4 (d, J=6.3 Hz), 132.0 (d, J=5.5 Hz), 130.4 (d, J=4.1 Hz), 124.4, 115.2, 115.0 (d, J=11.6 Hz), 110.4 (d, J=3.3 Hz), 110.3 (d, J=2.2 Hz), 102.0 (d, J=25.6 Hz), 101.4 (d, J=25.9 Hz), 55.61, 55.59.

2) Synthesis of Compound 18a ($Y_1$=F, $Y_2$=H)

White solid 18a (2.37 g, yield: 43%) was obtained by the same approach as in the preceding section 1) using 2,6-difluoro-4-methoxybenzaldehyde (3.01 g, 17.5 mmol) and 4-methoxyphenylacetic acid (2.88 g, 17.3 mmol) as starting materials.

Melting point: 159-162° C.

$^1$H NMR (600 MHz, CDCl$_3$): δ 7.71 (s, 1H), 7.14-7.10 (m, 2H), 6.81-6.77 (m, 2H), 6.35-6.31 (m, 2H), 3.78 (s, 3H), 3.75 (s, 3H).

$^{13}$C NMR (150 MHz, CDCl$_3$): δ 172.0, 161.6 (dd, J=14.0, 14.0 Hz), 160.9 (d, J=250.9 Hz), 160.8 (d, J=250.9 Hz), 159.2, 135.6, 130.7, 129.2, 127.7, 113.4, 105.7 (dd, J=19.3, 19.3 Hz), 98.11 (d, J=24.8 Hz), 98.08 (d, J=24.5 Hz), 55.8, 55.1.

3) Synthesis of Compound 17b ($Y_1$=H, $Y_2$=F)

To compound 17a (2.51 g), ethyl acetate (44.4 mL), ethanol (33.3 mL), and 10% Pd/C (Tokyo Chemical Industry Co., Ltd., approximately 55% product wetted with water) (371 mg) were added at room temperature in an argon atmosphere. Then, the mixture was stirred for 9.5 hours in a hydrogen atmosphere. After confirmation of the completion of the reaction by TLC, the reaction solution was filtered through celite. The filtrate was concentrated, and the obtained crude product (2.64 g) was recrystallized from hexane/chloroform to obtain white solid 17b (1.99 g, yield: 79%).

Melting point: 124-127° C.

$^1$H NMR (600 MHz, CDCl$_3$): δ 7.19 (dd, J=8.6, 8.5 Hz, 1H), 6.91 (dd, J=8.6, 8.5 Hz, 1H), 6.63 (ddd, J=8.6, 2.7, 0.5 Hz, 1H), 6.55 (dd, J=10.2, 2.7 Hz, 1H), 6.54 (dd, J=11.5, 2.4 Hz, 1H), 6.51 (dd, J=8.5, 2.6 Hz, 1H), 4.16 (dd, J=8.4, 7.3 Hz, 1H), 3.76 (s, 3H), 3.74 (s, 3H), 3.33 (dd, J=14.1, 7.3 Hz, 1H), 2.99 (dd, J=14.1, 8.4 Hz, 1H).

$^{13}$C NMR (150 MHz, CDCl$_3$): δ 178.05, 161.7 (d, J=245.4 Hz), 161.1 (d, J=246.5 Hz), 160.2 (d, J=11.0 Hz), 159.3 (d, J=10.7 Hz), 131.5 (d, J=6.6 Hz), 129.7 (d, J=5.5 Hz), 117.1 (d, J=16.5 Hz), 116.9 (d, J=15.4 Hz), 110.1 (d, J=3.0 Hz), 109.6 (d, J=3.0 Hz), 101.6 (d, J=25.6 Hz), 101.5 (d, J=26.1 Hz), 55.52, 55.45, 43.9, 31.0.

4) Synthesis of Compound 18b ($Y_1$=F, $Y_2$=H)

White solid compound 18b (1.80 g, yield: 89%) was obtained by the same approach as in the preceding section 3) using compound 18a (2.00 g, 6.24 mmol) as a starting material.

Melting point: 176-177° C.

$^1$H NMR (600 MHz, DMSO-df): δ 12.41 (brs, 1H), 7.16-7.12 (m, 2H), 6.85-6.81 (m, 2H), 6.64-6.58 (m, 2H), 3.75-3.65 (m, 1H), 3.72 (s, 3H), 3.71 (s, 3H), 3.15 (dd, J=14.0, 7.1 Hz, 1H), 2.95 (dd, J=14.0, 8.8 Hz, 1H).

$^{13}$C NMR (150 MHz, DMSO-d): δ 174.0, 161.34 (d, J=243.7 Hz), 161.26 (d, J=243.5 Hz), 159.1 (dd J=14.6, 14.6 Hz), 158.3, 130.3, 128.7, 113.7, 106.0 (dd, J=20.9, 20.9 Hz), 97.82 (d, J=23.7 Hz), 97.78 (d, J=24.2 Hz), 55.8, 54.9, 49.6, 25.6.

5) Synthesis of Compound 17c ($Y_1$=H, $Y_2$=F)

To compound 17b (1.00 g, 3.10 mmol), THF (31.0 mL) was added at room temperature in an argon atmosphere. LAH (6.6 mL, 6.6 mmol, a 1.0 M solution in diethyl ether) was added thereto under ice cooling, and the mixture was stirred for 4 hours. After confirmation of the completion of the reaction by TLC, ethyl acetate (5 mL) was added thereto under ice cooling. Then, water (2.5 mL), a 1 N aqueous sodium hydroxide solution (2.5 mL), and water (7.5 mL) were added dropwise thereto in this order. After filtration through celite, the filtrate was concentrated, and the obtained crude product (2.45 g) was purified by silica gel column chromatography (hexane/ethyl acetate) to obtain colorless clear oil compound 17c (0.90 g, yield: 94%).

$^1$H NMR (600 MHz, CDCl$_3$): δ 7.11 (dd, J=8.5, 8.5 Hz, 1H), 6.93 (dd, J=0.8, 8.0 Hz, 1H), 6.64 (dd, J=8.5, 2.5 Hz, 1H), 6.59-6.52 (m, 3H), 3.84-3.70 (m, 2H), 3.77 (s, 3H), 3.75 (s, 3H), 3.37 (ddd, J=8.0, 7.2. 7.0 Hz, 1H), 3.03 (dd, J=13.9, 7.2 Hz, 1H), 2.83 (dd, J=13.9, 8.0 Hz, 1H), 1.41 (brs, 1H).

$^{13}$C NMR (150 MHz, CDCl$_3$): δ 161.7 (d, J=245.1 Hz), 161.6 (d, J=244.3 Hz), 159.5 (d, J=11.0 Hz), 159.2 (d, J=11.0 Hz), 131.4 (d, J=6.9 Hz), 129.5 (d, J=7.4 Hz), 120.1 (d, J=14.9 Hz), 118.3 (d, J=16.5 Hz), 109.9 (d, J=2.8 Hz), 109.6 (d, J=3.3 Hz), 101.7 (d, J=27.0 Hz), 101.3 (d, J=26.4 Hz), 65.2, 55.5, 54.4, 41.9, 29.9.

6) Synthesis of Compound 18c ($Y_1$=F, $Y_2$=H)

Colorless clear oil compound 18c (0.70 g, yield: 73%) was obtained by the same approach as in the preceding section 5) using compound 18b (1.00 g, 3.10 mmol) as a starting material.

$^1$H NMR (600 MHz, CDCl$_3$): δ 7.17-7.13 (m, 2H), 6.86-6.82 (m, 2H), 6.39-6.34 (m, 2H), 3.78 (s, 3H), 3.78-3.75 (m, 2H), 3.74 (s, 3H), 3.07 (ddd, J=7.8, 7.6, 7.5 Hz, 1H), 2.94 (dd, J=13.8, 7.8 Hz, 1H), 2.83 (dd, J=13.8, 7.6 Hz, 1H), 1.39-1.33 (m, 1H).

$^{13}$C NMR (150 MHz, CDCl$_3$): δ 159.1 (dd, J=14.3, 14.3 Hz), 158.5, 133.4, 128.9, 114.0, 107.5 (dd, J=21.0, 21.0 Hz), 97.60 (d, J=23.9 Hz), 97.56 (d, J=24.2 Hz), 66.4, 55.6, 55.2, 47.5, 25.2.

7) Synthesis of Compound 17d ($Y_1$=H, $Y_2$=F)

To compound 17c (355 mg, 1.15 mmol), dichloromethane (15.2 mL) and a Dess-Martin reagent (1.47 g, 3.45 mmol) were added at room temperature in an argon atmosphere, and the mixture was stirred for 110 minutes. After confirmation of the completion of the reaction by TLC, a saturated aqueous solution of sodium bicarbonate/a saturated aqueous solution of sodium thiosulfate (1/1 (volume ratio), 20 mL) was added thereto, followed by extraction with chloroform three times. Then, the organic layer was washed with water and saturated saline and dried over anhydrous magnesium sulfate. After filtration, the filtrate was concentrated, and the obtained crude product (412 mg) was purified by silica gel column chromatography (hexane/ethyl acetate) to obtain colorless clear oil compound 17d (362 mg, yield: quant.).

$^1$H NMR (600 MHz, CDCl$_3$): δ 9.74 (s, 1H), 6.96 (dd, J=8.6, 8.5 Hz, 1H), 6.89 (dd, J=8.6, 8.4 Hz, 1H), 6.64 (ddd, J=8.6, 2.6, 0.4 Hz, 1H), 6.60 (dd, J=11.7, 2.6 Hz, 1H), 6.55 (dd, J=11.7, 2.5 Hz, 1H), 6.52 (dd, J=8.4, 2.5 Hz, 1H), 4.02 (dd, J=8.7, 6.4 Hz, 1H), 3.78 (s, 3H), 3.74 (s, 3H), 3.41 (dd, J=14.1, 6.4 Hz, 1H), 2.89 (dd, J=14.1, 8.7 Hz, 1H).

$^{13}$C NMR (150 MHz, CDCl$_3$): δ 199.3, 162.4 (d, J=16.0 Hz), 160.8 (d, J=14.9 Hz), 160.5 (d, J=11.3 Hz), 159.5 (d, J=11.0 Hz), 131.6 (d, J=6.6 Hz), 130.8 (d, J=6.1 Hz), 117.2 (d, J=16.2 Hz), 114.7 (d, J=16.2 Hz), 110.3 (d, J=3.0 Hz), 109.6 (d, J=2.5 Hz), 101.85 (d, J=26.1 Hz), 101.41 (d, J=25.6 Hz), 55.5, 55.4, 52.6, 28.0.

8) Synthesis of Compound 18d ($Y_1$=F, $Y_2$=H)

Colorless clear oil compound 18d (313 mg, yield: 86%) was obtained by the same approach as in the preceding section 7) using compound 18c (366 mg, 1.19 mmol) as a starting material.

$^1$H NMR (600 MHz, CDCl$_3$) δ 9.70 (d, J=1.6 Hz, 1H), 7.08-7.04 (m, 2H), 6.87-6.84 (m, 2H), 6.37-6.32 (m, 2H), 3.81 (ddd, J=8.8, 6.9, 1.6 Hz, 1H), 3.79 (s, 3H), 3.73 (s, 3H), 3.27 (dd, J=14.3, 6.9 Hz, 1H), 3.01 (dd, J=14.3, 8.8 Hz, 1H).

$^{13}$C NMR (150 MHz, CDCl$_3$): δ 199.8, 161.9 (d, J=244.3 Hz), 161.0 (d, J=244.3 Hz), 159.4 (dd, J=14.3, 14.3 Hz), 159.1, 129.9, 127.0, 114.4, 106.2 (dd, J=20.9, 20.9 Hz), 97.7 (d, J=6.3 Hz), 97.6 (d, J=6.6 Hz), 57.7, 55.6, 55.2, 22.7.

9) Synthesis of Compound 17ea ($Y_1$=H, $Y_2$=F, X=F) and compound 17eb ($Y_1$=H, $Y_2$=F, X=Cl)

Diethyl(difluoromethyl) phosphonate (753 μL, 4.80 mmol), THF (2.0 mL), and LDA (4.0 mL, 4.52 mmol, a 1.13 M solution in hexane) were added at −78° C. in an argon atmosphere, and the mixture was stirred for 1 hour. Then, compound 17d (200 mg, 0.653 mmol, in THF, 6.7 mL) was added thereto. The mixture was stirred at −78° C. for 30 minutes, then warmed to room temperature, stirred for 1 hour, and then stirred overnight under reflux. After confirmation of the completion of the reaction by TLC, a saturated aqueous solution of ammonium chloride was added thereto, followed by extraction with ethyl acetate three times. Then, the organic layer was washed with water and saturated saline and dried over anhydrous magnesium sulfate. After filtration, the filtrate was concentrated, and the obtained crude product (857 mg) was purified by silica gel column chromatography to obtain a colorless clear oil (66.3 mg, compound 17ea:compound 17eb=1:1 ($^1$H NMR ratio), yield: 30%).

Compound 17ea $^1$H NMR (600 MHz, CDCl$_3$) δ 7.03 (dd, J=8.5, 8.5 Hz, 1H), 6.92 (dd, J=8.4, 8.4 Hz, 1H), 6.62-6.54 (m, 4H), 4.51 (dddd, J=24.3, 10.3, 1.2, 1.2 Hz, 1H), 3.94-3.88 (m, 1H), 3.77 (s, 3H), 3.76 (s, 3H), 2.94 (dd, J=13.7, 7.2 Hz, 1H), 2.91 (dd, J=13.7, 8.4 Hz, 1H).

$^{13}$C NMR (150 MHz, CDCl$_3$) δ 161.7 (d, J=244.3 Hz), 161.1 (d, J=245.4 Hz), 159.6 (d, J=11.0 Hz), 159.5 (d, J=11.0 Hz), 156.1 (dd, J=287.8, 287.8 Hz), 131.5 (d, J=6.6 Hz), 129.1 (d, J=6.9 Hz), 121.8 (ddd, J=14.6, 1.9, 1.9 Hz), 117.8 (d, J=15.7 Hz), 109.8 (d, J=2.2 Hz), 109.6 (d, J=3.3 Hz), 101.9 (d, J=26.1 Hz), 101.4 (d, J=26.4 Hz), 80.6 (ddd, J=21.9, 19.8, 1.9 Hz), 55.53, 55.46, 34.9 (d, J=5.0 Hz), 31.6.

Compound 17eb $^1$H NMR (600 MHz, CDCl$_3$) δ 7.01 (dd, J=8.5, 8.5 Hz, 1H), 6.91 (dd, J=7.9, 7.9 Hz, 1H), 6.62-6.54 (m, 4H), 6.17 (d, J=9.7 Hz, 1H), 4.07 (ddd, J=9.7, 8.1, 7.5 Hz, 1H), 3.77 (s, 3H), 3.76 (s, 3H), 2.99 (dd, J=13.7, 8.1 Hz, 1H), 2.95 (dd, J=13.7, 7.5 Hz, 1H).

$^{13}$C NMR (150 MHz, CDCl$_3$): δ 161.8 (d, J=244.3 Hz), 161.3 (d, J=245.9 Hz), 159.8 (d, J=11.0 Hz), 159.6 (d, J=11.0 Hz), 131.6 (d, J=7.4 Hz), 131.0 (d, J=1.7 Hz), 129.7 (d, J=6.6 Hz), 121.5, 120.3 (d, J=14.3 Hz), 117.5 (d, J=16.5

Hz), 110.0 (d, J=3.0 Hz), 109.7 (d, J=3.3 Hz), 102.1 (d, J=26.4 Hz), 101.5 (d, J=26.4 Hz), 55.7, 55.6, 41.7, 33.7.

10) (Synthesis of compounds 18ea ($Y_1$=F, $Y_2$=H, X=F) and 18eb ($Y_1$=F, $Y_2$=H, X=Cl))

A colorless clear oil (81.0 mg, compound 18ea:compound 18eb=4:3 ($^1$H NMR ratio), yield: 36%) was obtained by the same approach as in the preceding section 9) using compound 18d (200 mg, 0.653 mmol) as a starting material.

Compound 18ea $^1$H NMR (600 MHz, CDCl$_3$): δ 7.11-7.07 (m, 2H), 6.80-6.76 (m, 2H), 6.35-6.30 (m, 2H), 4.37 (ddd, J=24.5, 10.4, 2.4 Hz, 1H), 3.72 (s, 3H), 3.70 (s, 3H), 3.69-3.62 (m, 1H), 2.86 (dd, J=13.6, 6.5 Hz, 1H), 2.80 (dd, J=13.6, 9.8 Hz, 1H).

$^{13}$C NMR (150 MHz, CDCl$_3$): δ 162.15 (d, J=244.8 Hz), 162.07 (d, J=244.8 Hz), 159.5 (dd, J=11.0, 11.0 Hz), 158.5, 156.3 (dd, J=287.5, 287.5 Hz), 135.4, 128.1, 114.1, 107.2 (dd, J=21.0, 21.0 Hz), 97.73 (d, J=24.2 Hz), 97.69 (d, J=23.9 Hz), 81.5 (dd, J=20.5 Hz), 55.8, 55.4, 39.2 (d, J=4.4 Hz), 28.6.

Compound 18eb $^1$H NMR (600 MHz, CDCl$_3$): δ 7.11-7.07 (m, 2H), 6.80-6.76 (m, 2H), 6.35-6.30 (m, 2H), 6.00 (d, J=10.1 Hz, 1H), 3.86 (ddd, J=10.1, 9.6, 7.2 Hz, 1H), 3.72 (s, 3H), 3.70 (s, 3H), 2.90 (dd, J=13.9, 7.2 Hz, 1H), 2.86 (dd, J=13.9 9.6 Hz, 1H).

$^{13}$C NMR (150 MHz, CDCl$_3$) δ 162.15 (d, J=244.8 Hz), 162.07 (d, J=244.8 Hz), 159.6 (dd, J=11.0, 11.0 Hz), 158.6, 133.8, 132.0, 128.4, 121.0, 114.2, 106.6 (d, J=20.9, 20.9 Hz), 97.73 (d, J=24.2 Hz), 97.69 (d, J=23.9 Hz), 55.8, 55.4, 45.6, 29.8.

11) Synthesis of Compound 17-F ($Y_1$=H, $Y_2$=F, X=F) and compound 17-Cl ($Y_1$=H, $Y_2$=F, X=Cl)

The mixture of compound 17ea and compound 17eb (33.2 mg, compound 17ea: 16.6 mg (0.0465 mmol), compound 17eb: 16.6 mg (0.0465 mmol)) synthesized as described above was subjected to the approach of step C of Production Example 1 to obtain a pale yellow solid (31.3 mg). The obtained crude product was purified by high-performance liquid chromatography (column: L-column 2 ODS, solvent system: 0.1% aqueous formic acid solution/acetonitrile (1/1), isocratic). As a result, white solid compound 17-F (7.0 mg, yield: 48%) and white solid compound 17-Cl (8.2 mg, yield: 51%) were obtained.

Compound 17-F

Melting point: 90-91° C.

HRMS (ESI, negative mode) calc 311.0701 [M–H]$^-$; found: 311.0695.

$^1$H NMR (600 MHz, CDCl$_3$): δ 6.97 (dd, J=8.6, 8.6 Hz, 1H), 6.87 (dd, J=8.4, 8.4 Hz, 1H), 6.55-6.46 (m, 4H), 4.88 (brs, 1H), 4.83 (brs, 1H), 4.50 (dddd, J=24.3, 10.4, 1.1, 1.1 Hz, 1H), 3.92-3.85 (m, 1H), 2.93 (dd, J=13.9, 7.2 Hz, 1H), 2.89 (dd, J=13.9, 8.2 Hz, 1H).

$^{13}$C NMR (150 MHz, CDCl$_3$) δ 161.6 (d, J=245.7 Hz), 161.0 (d, J=246.2 Hz), 156.1 (dd, J=288.0, 288.0 Hz), 155.4 (d, J=12.1 Hz), 155.3 (d, J=12.1 Hz), 131.7 (d, J=6.6 Hz), 129.3 (d, J=6.6 Hz), 122.1 (dd, J=15.0, 2.3 Hz), 118.1 (d, J=16.0 Hz), 111.1 (d, J=3.3 Hz), 110.9 (d, J=3.3 Hz), 103.5 (d, J=25.6 Hz), 103.0 (d, J=25.3 Hz), 80.6 (ddd, J=22.0, 19.8, 2.2 Hz), 35.0 (d, J=5.0 Hz), 34.6.

Compound 17-Cl

HRMS (ESI, negative mode) calc: 343.0110 [M–H]$^-$; found 343.0102.

$^1$H NMR (600 MHz, CDCl$_3$) δ 6.96 (dd, J=8.4, 0.4 Hz, 1H), 6.86 (dd, J=8.3, 8.3 Hz, 1H), 6.60-6.43 (m, 4H), 6.16 (d, J=9.6 Hz, 1H), 5.08 (brs, 2H), 4.05 (ddd, J=9.6, 8.0, 7.7 Hz, 1H), 2.97 (dd, J=13.6, 8.0 Hz, 1H), 2.93 (dd, J=13.6, 7.7 Hz, 1H).

$^{13}$C NMR (150 MHz, CDCl$_3$): δ 161.7 (d, J=245.4 Hz), 161.3 (d, J=246.5 Hz), 155.7 (d, J=12.1 Hz), 155.5 (d, J=11.3 Hz), 131.9 (d, J=6.6 Hz), 130.9 (d, J=1.1 Hz), 130.0 (d, J=7.2 Hz), 121.6, 120.5 (d, J=15.4 Hz), 117.8 (d, J=16.0 Hz), 111.4 (d, J=2.8 Hz), 111.1 (d, J=2.8 Hz), 103.7 (d, J=25.9 Hz), 103.2 (d, J=25.6 Hz), 41.7, 33.6.

12) Synthesis of Compound 18-F ($Y_1$=F, $Y_1$=H, X=F) and compound 18-Cl ($Y_1$=F, $Y_7$=H, X=Cl)

White solid compound 18-F (7.6 mg, yield: 37%) and white solid compound 18-Cl (6.9 mg, yield: 41%) were obtained by the same approach as in the preceding section 11) using the mixture of compound 18ea and compound 18eb (40.5 mg, compound 18ea: 22.2 mg (0.0653 mmol), compound 18eb: 18.3 mg (0.0490 mmol)) as a starting material.

Compound 18-F

HRMS (ESI, negative mode) calc 311.0701 [M–H]$^-$; found: 311.0696.

$^1$H NMR (600 MHz, CDCl$_3$) δ 7.12-7.07 (m, 2H), 6.79-6.75 (m, 2H), 6.36-6.31 (m, 2H), 4.43 (ddd, J=24.4, 10.4, 2.4 Hz, 1H), 3.72-3.66 (m, 1H), 2.91 (dd, J=13.7, 6.2 Hz, 1H), 2.84 (dd, J=13.7, 9.7 Hz, 1H).

$^{13}$C NMR (150 MHz, CDCl$_3$): δ 162.1 (d, J=245.1 Hz), 162.0 (d, J=245.1 Hz), 155.8 (dd, J=287.3, 287.3 Hz), 155.8 (dd, J=14.6, 14.6 Hz), 154.5, 135.5, 128.3, 115.5, 107.0 (dd, J=20.5, 20.5 Hz), 99.3 (d, J=6.6 Hz), 99.2 (d, J=6.6 Hz), 81.5 (dd, J=20.5, 20.5 Hz), 39.2 (d, J=4.7 Hz), 29.8.

Compound 18-Cl

HRMS (ESI, negative mode) calc: 343.0110 [M–H]$^-$; found 343.0099.

$^1$H NMR (600 MHz, CDCl$_3$) δ 7.14-7.08 (m, 2H), 6.80-6.76 (m, 2H), 6.38-6.32 (m, 2H), 6.06 (d, J=9.9 Hz, 1H), 5.44 (brs, 1H), 4.90 (brs, 1H), 3.91 (ddd, J=9.9, 8.8, 7.2 Hz, 1H), 2.94 (dd, J=13.6, 7.2 Hz, 1H), 2.91 (dd, J=13.6, 8.8 Hz, 1H).

$^{13}$C NMR (150 MHz, CDCl$_3$): δ 162.1 (d, J=245.4 Hz), 162.0 (d, J=245.4 Hz), 155.7 (dd, J=14.6, 14.6 Hz), 154.5, 133.9, 131.9, 128.6, 121.1, 115.6, 106.8 (dd, J=20.6, 20.6 Hz), 99.31 (d, J=22.8 Hz), 99.27 (d, J=22.8 Hz), 45.6, 28.5.

Production Example 15 Synthesis of 4-(1-(4-acetoxy-2,6-difluorophenyl)-4,4-difluorobut-3-en-2-yl)phenylacetate (compound 17-F—Ac)

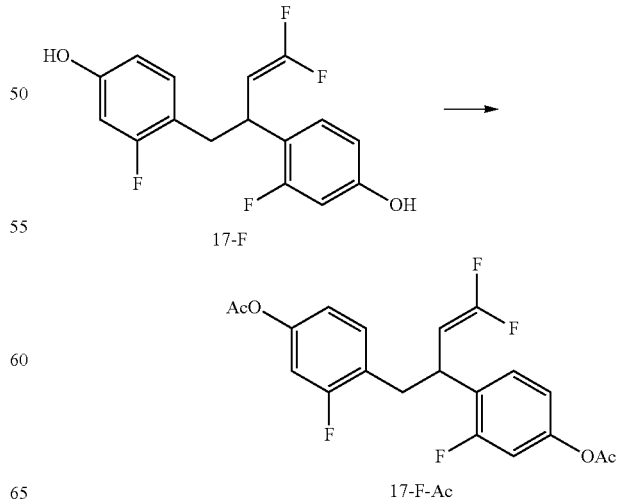

To compound 17-F (30.0 mg, 0.0961 mmol), acetic anhydride (908 µL, 9.61 mmol) and triethylamine (266 µL, 1.921 mmol) were added at room temperature, and the mixture was stirred for 3 hours. After confirmation of the completion of the reaction by TLC, 4 N hydrochloric acid was added thereto, followed by extraction with ethyl acetate three times. Then, the organic layer was washed with water and saturated saline in this order and dried over anhydrous magnesium sulfate. After filtration, the filtrate was concentrated, and the obtained crude product (55.3 mg) was purified by preparative thin-layer chromatography (hexane/ethyl acetate=2/1) to obtain colorless clear oil compound 17-F—Ac (17.8 mg, yield: 47%).

$^1$H NMR (600 MHz, CDCl$_3$): δ 7.15 (dd, J=8.5, 8.5 Hz, 1H), 7.05 (dd, J=8.3, 8.3 Hz, 1H), 6.86-6.77 (m, 4H), 4.53 (ddd, J=24.0, 10.2, 1.0 Hz, 1H), 4.03-3.96 (m, 1H), 3.02 (dd, J=13.7, 6.8 Hz, 1H), 2.99 (dd, J=13.7, 8.8 Hz, 1H), 2.29 (s, 3H), 2.28 (s, 3H).

$^{13}$C NMR (150 MHz, CDCl$_3$): δ 169.0, 160.9 (d, J=247.6 Hz), 160.3 (d, J=247.6 Hz), 156.3 (dd, J=288.7, 288.7 Hz), 150.1 (d, J=11.0 Hz), 150.0 (d, J=11.0 Hz), 131.3 (d, J=6.3 Hz), 129.0 (d, J=6.0 Hz), 127.2 (ddd, J=14.3, 1.9, 1.9 Hz), 123.3 (d, J=15.7 Hz), 117.4 (d, J=3.3 Hz), 117.1 (d, J=3.3 Hz), 109.9 (d, J=25.3 Hz), 109.4 (d, J=25.9 Hz), 79.9 (ddd, J=22.6, 19.5, 1.9 Hz), 34.9 (d, J=5.0 Hz), 34.6, 29.7.

Example 1 Evaluation of Ability of Compound to Bind to ERα and ERβ

1) Cell Culture

A human kidney-derived cell line HEK293 was cultured (37° C., 5% CO$_2$) in Dulbecco's modified Eagle medium (hereinafter, abbreviated to DMEM) containing 10% (v/v) fetal bovine serum (FBS) and penicillin/streptomycin.

2) Measurement of Binding Activity Against ERs

This measurement was carried out according to the method described in JP-B-5990058. Specifically, HEK293 cells were inoculated at a cell density of 4.0×10$^4$ cells/well to a 96-well plate. After 12 hours therefrom, the medium was replaced with a culture solution (DMEM containing 5% (v/v) charcoal-treated serum). The cells were cotransfected with pBIND-ERα for the expression of ERα LBD or pBIND-ERβ for the expression of ERβ LBD (Promega Corp.) and pGL4.35[luc2P/9XGAL4UAS/Hygro](Promega Corp.) using Lipofectamine 2000 (Invitrogen Corp.) according to the protocol attached to the product. 24 hours after transfection, the medium was replaced with a culture solution containing a test sample, followed by culture for another 24 hours. The activity measurement of firefly luciferase (index for the ligand binding activity of ER) and *Renilla reniformis* luciferase (index for the transfection efficiency of the plasmids) was carried out using Dual-Glo™ Luciferase Assay System (Promega Corp.) according to the attached protocol. The luminescence intensity of the firefly luciferase was divided by the luminescence intensity of the *Renilla reniformis* luciferase to calculate a relative light unit (RLU).

3) Results

The ability of the compounds shown in Table 1 (compounds 1, 2, 5 to 8, 10, 12 to 14, 16, 17-F, 17-Cl, 18-F and 18-Cl) to bind to ERα and ERβ were evaluated using estradiol as a positive control. All the compounds had a higher RLU value than that of a negative control at any concentration and were therefore confirmed to have the ability to bind to ER (Table 1). All the compounds were also confirmed to have higher ability to bind to ERβ than to ERα.

TABLE 1

| | ERα | | | | | | | |
|---|---|---|---|---|---|---|---|---|
| Concentration (nM) | E2 | 1 | 2 | 5 | 6 | 7 | 8 | 10 |
| 0.01 | 0.035144 | — | 0.023687 | — | — | 0.027994 | 0.005812 | — |
| 0.1 | 0.095945 | — | 0.019429 | — | — | 0.037303 | 0.005926 | — |
| 1 | 1.849409 | 0.011227 | 0.016301 | 0.006803 | 0.008097 | 0.029187 | 0.007223 | 0.008272 |
| 10 | 2.370331 | 0.010013 | 0.01763 | 0.008307 | 0.010979 | 0.061905 | 0.118394 | 0.016297 |
| 100 | 2.402706 | 0.035143 | 0.022163 | 0.318999 | 0.011825 | 1.588012 | 0.422992 | 0.011558 |

| | ERα | | | | | | | |
|---|---|---|---|---|---|---|---|---|
| Concentration (nM) | 12 | 13 | 14 | 16 | 17-F | 17-Cl | 18-F | 18-Cl |
| 0.01 | 0.006803 | 0.013624 | 0.010309 | 0.014239 | 0.02573 | 0.03467 | 0.036076 | 0.039804 |
| 0.1 | 0.020772 | 0.006796 | 0.014955 | 0.01773 | 0.060248 | 0.03125 | 0.131158 | 0.042553 |
| 1 | 0.017526 | 0.01285 | 0.020042 | 0.017143 | 0.219814 | 0.053946 | 1.177231 | 0.122034 |
| 10 | 0.011906 | 0.016113 | 0.014926 | 0.018204 | 1.873027 | 0.92 | 2.967765 | 2.2626 |
| 100 | 0.008685 | 0.014315 | 0.020472 | 0.024504 | 3.193114 | 2.706883 | 3.390669 | 3.228723 |

* Negative control: 0.00847035

| | ERβ | | | | | | | |
|---|---|---|---|---|---|---|---|---|
| Concentration (nM) | E2 | 1 | 2 | 5 | 6 | 7 | 8 | 10 |
| 0.01 | 0.078206 | — | 0.024772 | 0.016985 | — | 0.060456 | 0.012235 | — |
| 0.1 | 0.712555 | — | 0.020979 | 0.139501 | — | 0.910405 | 0.525381 | — |
| 1 | 2.4 | 0.047256 | 0.020563 | 0.974421 | 0.010457 | 1.876628 | 0.99794 | 0.015391 |
| 10 | 2.722112 | 0.780087 | 0.291745 | 1.152729 | 0.020306 | 2.074004 | 1.068063 | 0.0134 |
| 100 | 2.727074 | 0.673992 | 1.09292 | 1.216449 | 0.204136 | 2.407946 | 1.031438 | 0.221079 |

| | ERβ | | | | | | | |
|---|---|---|---|---|---|---|---|---|
| Concentration (nM) | 12 | 13 | 14 | 16 | 17-F | 17-Cl | 18-F | 18-Cl |
| 0.01 | 0.018362 | 0.012931 | 0.027083 | 0.017304 | 0.427343 | 0.041082 | 0.645222 | 0.074223 |
| 0.1 | 0.017316 | 0.018868 | 0.021879 | 0.022161 | 1.771483 | 0.116041 | 2.100612 | 0.425891 |
| 1 | 0.030733 | 0.024706 | 0.02069 | 0.017588 | 2.020747 | 1.220227 | 2.316759 | 1.818868 |

TABLE 1-continued

| 10 | 0.020661 | 0.043133 | 0.088514 | 0.067288 | 2.366838 | 1.682192 | 2.025478 | 1.997288 |
| 100 | 0.026 | 0.832168 | 0.994624 | 0.862525 | 2.186261 | 2.028628 | 2.303973 | 2.261479 |

* Negative control: 0.0118997

Note:
A hyphen "—" represent an unevaluated result

Example 2 Evaluation of Ability of Compound to Activate Transcription of ERα and ERβ

1) Experimental Method (Measurement of Transcriptional Activity Mediated by ERs)

HEK293 cells were inoculated at a cell density of $4.0 \times 10^4$ cells/well to a 96-well plate. After 12 hours therefrom, the medium was replaced with a culture solution (DMEM containing 5% (v/v) charcoal-treated serum). The cells were cotransfected with pcDNA3-ERα or pcDNA3-ERβ (Promega Corp.) and pERE and pRL-CMV (Promega Corp.) using Lipofectamine 2000 (Invitrogen Corp.) according to the protocol attached to the product. 24 hours after transfection, the medium was replaced with a culture medium containing a test sample, followed by culture for another 24 hours. Then, luciferase activity was measured using Dual-Glo™ Luciferase Assay System (Promega Corp.) according to the attached protocol. The luminescence intensity of firefly luciferase (index for the ability to activate transcription mediated by ERE) was divided by the luminescence intensity of *Renilla reniformis* luciferase (index for the transfection efficiency of the plasmids) to calculate a relative light unit (RLU).

2) Results

The ability of compounds 7, 17-F, and 18-F to activate the transcription of ERα and ERβ were evaluated using estradiol as a positive control. As a result, all the compounds had a higher RLU value than that of a negative control at any concentration and were therefore confirmed to have the ability to activate the transcription of ER. All the compounds also had a lower transcription activation concentration for ERβ than for ERα and thus confirmed to have high ERβ selectivity.

TABLE 2

| ERα | | | | |
| --- | --- | --- | --- | --- |
| Concentration (pM) | E2 | 7 | 17-F | 18-F |
| 0.01 | — | — | — | — |
| 0.1 | 0.008994 | 0.006825 | 0.008213 | 0.011939 |
| 1 | 0.008892 | 0.008059 | 0.010227 | 0.013366 |
| 10 | 0.01847 | 0.008285 | 0.018349 | 0.019708 |
| 100 | 0.049321 | 0.016208 | 0.041248 | 0.04067 |
| 1000 | 0.057426 | 0.040264 | 0.062016 | 0.063946 |
| 10000 | 0.063143 | 0.047761 | 0.054011 | 0.061524 |

* Negative control: 0.004573

| ERβ | | | | |
| --- | --- | --- | --- | --- |
| Concentration (pM) | E2 | 7 | 17-F | 18-F |
| 0.01 | 0.002577 | 0.002068 | 0.002468 | 0.003231 |
| 0.1 | 0.002274 | 0.002153 | 0.004255 | 0.00681 |
| 1 | 0.005373 | 0.00383 | 0.011038 | 0.012814 |
| 10 | 0.019689 | 0.011913 | 0.030227 | 0.034787 |
| 100 | 0.031674 | 0.023364 | 0.032375 | 0.036418 |
| 1000 | 0.035115 | 0.032532 | 0.03342 | 0.036593 |
| 10000 | 0.033687 | 0.034709 | 0.035074 | 0.037064 |

* Negative control: 0.001475
Note:
A hyphen "—" represents an unevaluated result

Example 3 Test of Efficacy of Compound 17-F on Prostate Using Testosterone-Induced Prostatic Hyperplasia Rat 1) Animal 12-week-old male Slc:SD (SPF) rats were obtained from Japan SLC, Inc. An acclimatization period was established for 1 week after receipt. During the acclimatization period, the rats were allowed to freely ingest a powder diet (AIN-93G).

2) Implantation of Osmotic Pump

After body weight measurement, back hair was shaved under isoflurane (AbbVie GK) inhalation anesthesia, and carprofen was subcutaneously administered to the rats. Then, an incision of approximately 1 cm at the maximum was made on the cranial side in the back. An osmotic minipump Alzet (Muromachi Kikai Co., Ltd.) containing testosterone and compound 17-F or finasteride (Sigma-Aldrich Co. LLC) was subcutaneously implanted. From this osmotic pump, testosterone (3 mg/kg body weight/day) (Sigma-Aldrich Co. LLC) and compound 17-F (0.1 mg/body weight/day or 1 mg/kg body weight/day) or finasteride (0.1 mg/kg body weight/day or 1 mg/kg body weight/day) were continuously administered for 28 days. Since the implantation of the osmotic pump, the rats were allowed to freely ingest customized feed AIN-93G (Oriental Yeast Co., Ltd.) free from components derived from soybeans.

3) Photographing of Skin and Harvesting of Prostate

After a lapse of 28 days, body weights were measured, and subsequently, the rats were euthanized by blood letting under isoflurane anesthesia. Back hair was shaved, followed by photographing. Then, the abdominal cavity was opened to harvest the prostate on the ventral side. Wet weights were measured.

4) Results 4-1) Effect on Prostatic Hyperplasia

The prostate on the ventral side harvested from each individual was photographed after trimming of fat attached around the prostate. FIG. 1 shows the photograph of the typical prostate of each group. Apparently evident prostatic hyperplasia occurred in a group given testosterone alone, as compared with a DMSO administration group. Concentration-dependent decrease in the size of the prostate was visually confirmed in groups given testosterone and finasteride (anti-androgen drug used as a therapeutic drug for prostatic hyperplasia) or compound 17-F.

Figure 2:
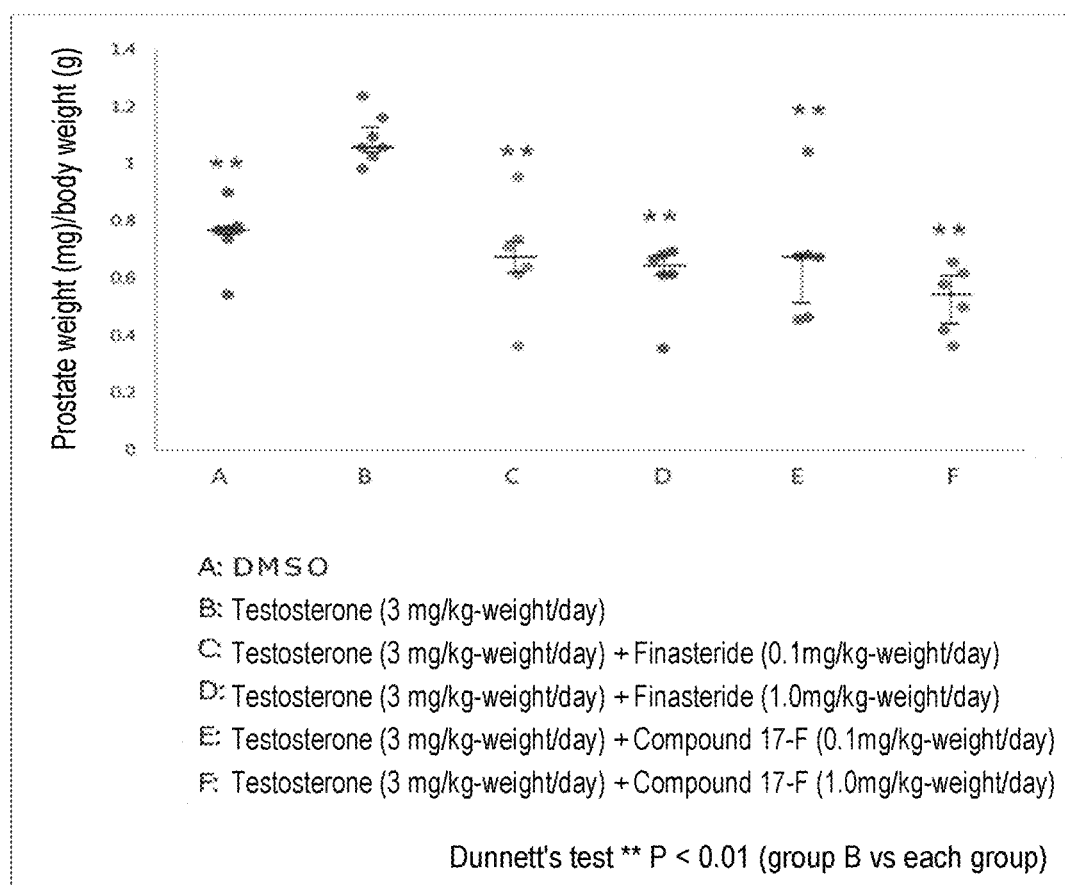
FIG. 2 shows the prostatic hyperplasia inhibitory effect of the compound of the present invention (the weight of the prostate).

The weight of the prostate was measured, and the value was corrected with the body weight. The results are shown in FIG. 2. The value was elevated in the testosterone administration group as compared with the DMSO administration group, whereas the value was decreased to almost the same level as in the DMSO administration group, in the groups given testosterone and finasteride or compound 17-F at the same time. This demonstrated that compound 17-F has a prostatic hyperplasia inhibiting effect at almost the same level as in finasteride, a therapeutic drug for prostatic hyperplasia.

4-2) Effect on Sebum Secretion

Figure 3:
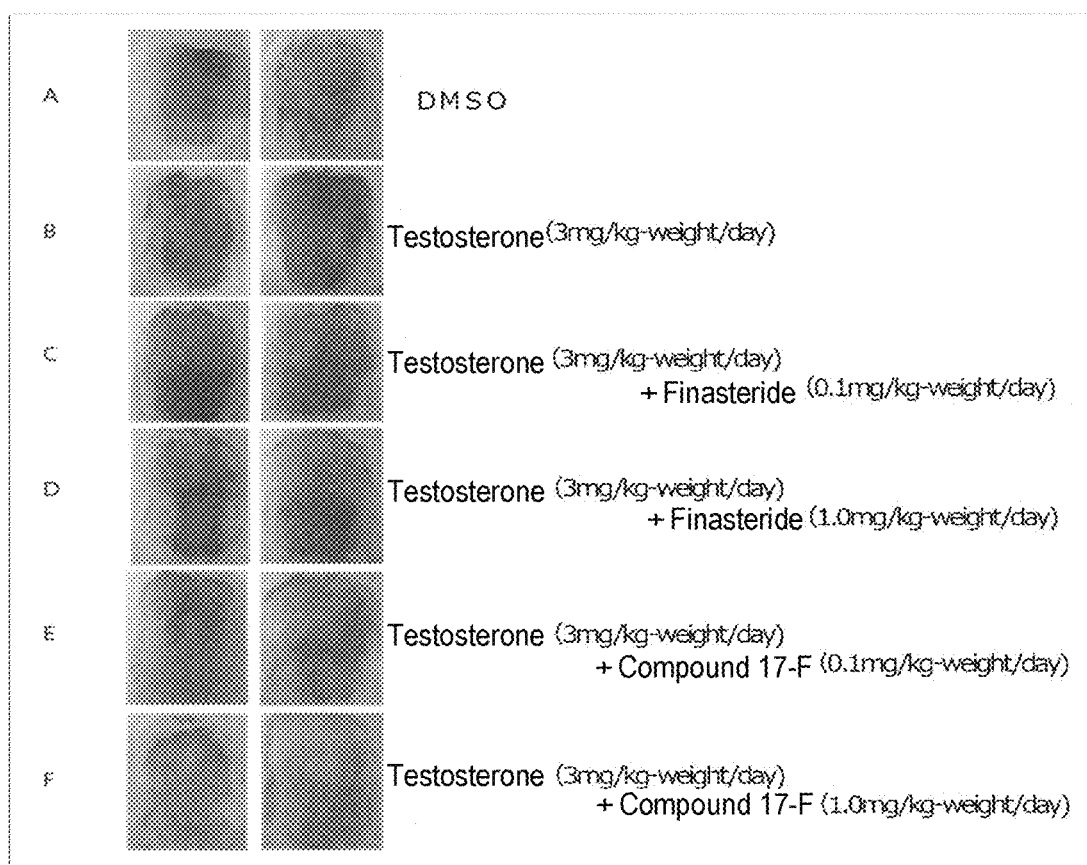
FIG. 3 shows the sebum secretion inhibitory effect of the compound of the present invention.

After blood letting, the back hair of the rats was shaved, followed by photographing (FIG. 3). The report of Arch Dermatol Res (2012) 304: 499-510 states that the back skin colors of male rats become brown with increase in their ages by week because the action of sebaceous glands is activated by the effects of androgen. In this test, evident skin browning was confirmed in the testosterone administration group as compared with the DMSO administration group. On the other hand, it was revealed that skin browning induced by testosterone was markedly inhibited in the testosterone and 17-F administration group. However, such an inhibitory effect was not confirmed in the testosterone and finasteride administration group. This suggested the possibility that compound 17-F can inhibit increased sebum secretion induced by testosterone.

Example 4 Test of Efficacy of Compound 17-F on Skin Temperature Using Ovariectomized Rat 1) Material and Method
1-1) Animal 8-week-old female Crl:CD (SD) rats were obtained from Charles River Laboratories Japan, Inc. and individually identified by the ear punching method on the receipt date. Then, an acclimatization period was established for 1 week. The animals were raised in a rearing room under a set environment involving a temperature of 22±3° C., a humidity of 50±20%, air ventilation from 13 to 17 times/hour, and a lighting time from 8:00 to 20:00. During the acclimatization period, the rats were allowed to freely ingest solid feed CRF-1 (Oriental Yeast Co., Ltd.). Since the feeding with CRF-1, the rats were allowed to freely ingest customized feed AIN-93G (Oriental Yeast Co., Ltd.) free from components derived from soybeans.

1-2) Sham Surgery and Oophorectomy Surgery (OVX)

On the end date of acclimatization and the following day, the flank cavity was opened under isoflurane anesthesia to harvest the right and left ovaries including fallopian tubes. Other non-OVX rats were subjected to only opening and suture (sham surgery). Immediately thereafter, an antibiotic was subcutaneously administered at a dose of 100 µl/animal. After the surgery, the sham surgery or OVX animals were given customized feed and raised for approximately 1 week.

1-3) Acclimatization to Skin Temperature Measurement Environment 1 week after sham surgery or OVX, the rats were placed in restrainers without anesthesia for acclimatization to a skin temperature measurement environment, and left standing for 2 minutes per animal at a measurement location equipped with an infrared radiation thermometer (Keyence Corporation, sensor head: FT-H10, amplifier unit: FT-H10).

1-4) Tail Skin Temperature Measurement

Before administration of a test substance and from 12:00 to 3:00 (dark phase) of 3, 5, 7, 14, and 21 days after the start of administration, the rats were placed in restrainers without anesthesia, and skin temperatures were measured at a site 3 cm on the tip side from the tail root using the infrared radiation thermometer. The measurement was performed for 1 minute per animal, and an average value thereof was used as a skin temperature.

1-5) Administration of Test Substance

From 1.5 hours before a shift from the light phase to the dark phase (18:30), a negative solvent (DMSO) or a test substance was subcutaneously administered at a dose of 0.5 ml/kg to the back of the neck according to Table 3 described below using a syringe and an injection needle.

TABLE 3

| Group | Test substance | Dose (µg/kg/day) | The number of animals |
|---|---|---|---|
| A | Sham surgery | Negative solvent | | 10 |
| B | OVX | Negative solvent | | 10 |
| C | OVX | Estradiol | 4 | 10 |
| D | OVX | Compound 17-F | 4 | 10 |
| E | OVX | Compound 17-F | 40 | 10 |
| F | OVX | Compound 17-F | 400 | 10 |

1-6) Organ Harvesting

After the completion of all procedures of measurement and analysis, the rats were euthanized by blood letting under isoflurane anesthesia, and the uterus was harvested. Wet weights were measured.

1-7) Statistical Analysis

Skin temperatures differed largely among individuals, and the Smirnov-Grubbs test was conducted in order to exclude outliers beforehand. Results of measuring tail skin temperatures and results of measuring uterus weights were statistically analyzed by testing using the Dunnett's test.

Figure 4:
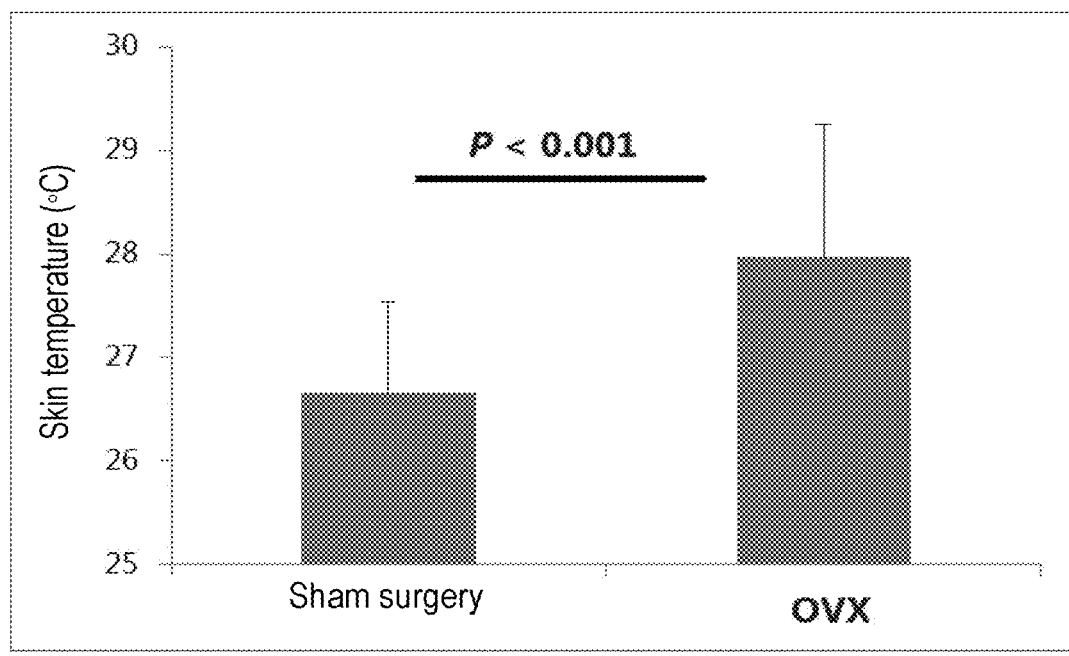
FIG. 4 shows the tail skin temperatures of ovariectomized (OVX) rats.

2) Results
2-1) Change in Skin Temperature 1 week after sham surgery or OVX, tail skin temperatures were measured using an infrared radiation thermometer before the start of administration (FIG. 4). The skin temperature was confirmed to significantly elevate in the OVX group as compared with the sham surgery group.

Figures 1, 5:
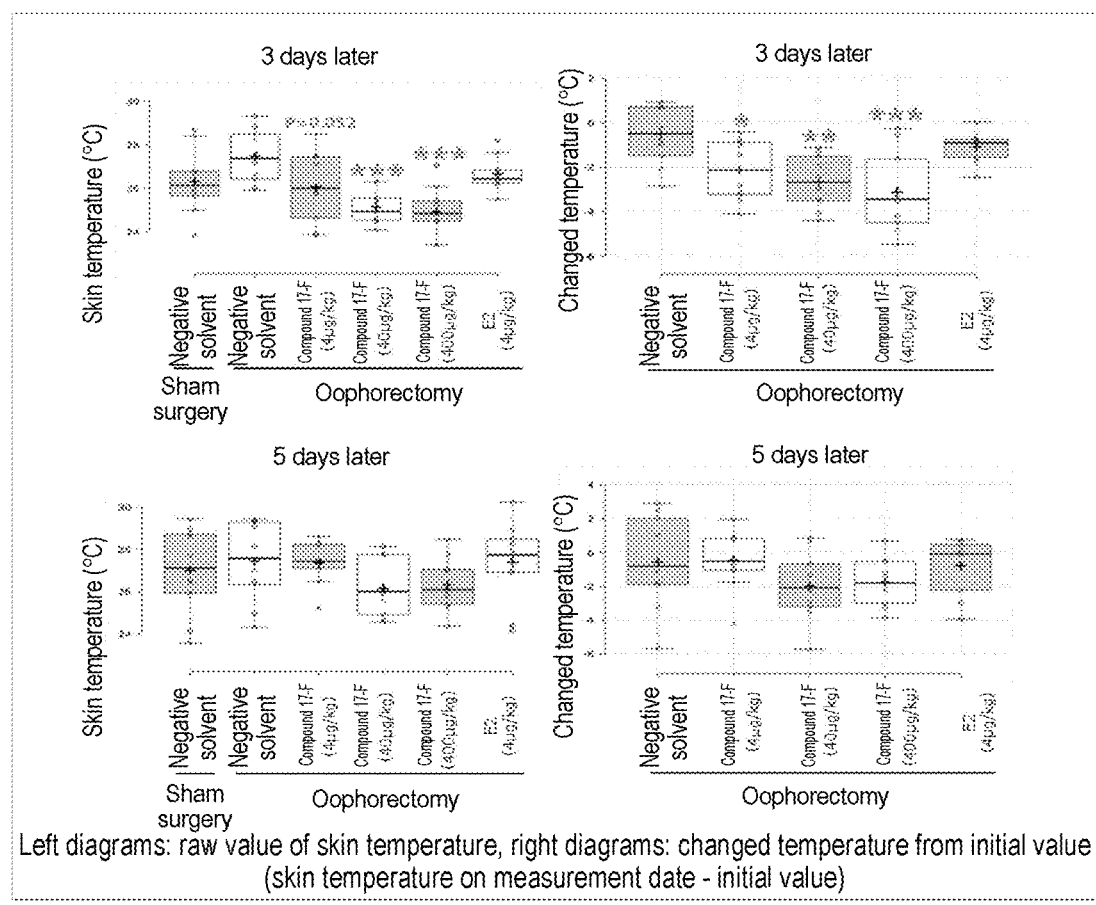
Figures 2, 5:
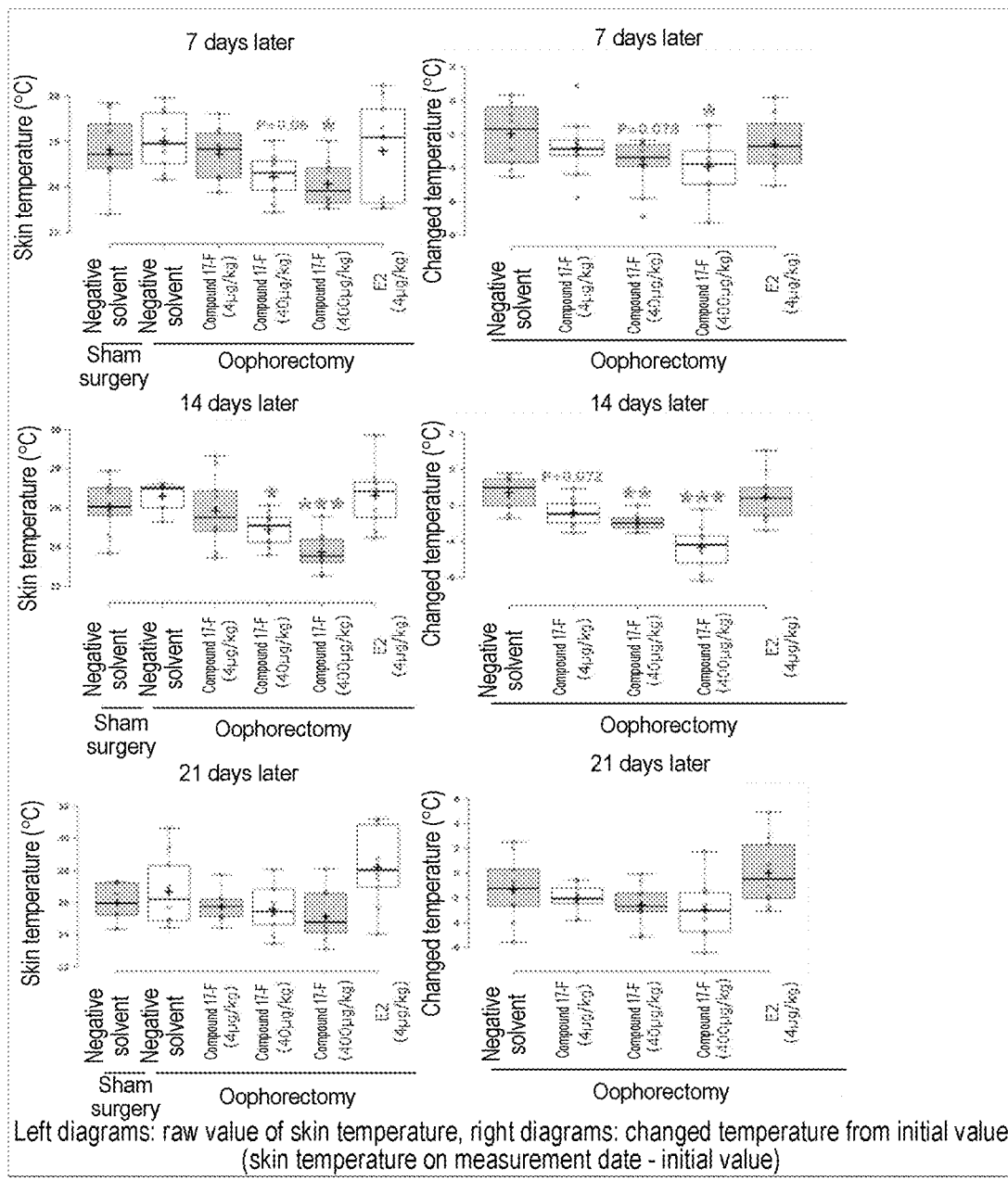

Then, grouping was performed, and the subcutaneous administration of a test sample was started from the following day. 3, 5, 7, 14, and 21 days after the start of administration, tail skin temperatures were measured (FIGS. 5-1 and 5-2). 3 days after the start of administration, a raw value of the skin temperature and a changed temperature from the initial value (skin temperature on the measurement date-initial value) were confirmed to decrease in the compound 17-F administration group (4, 40, and 400 µg/kg) as compared with a negative solvent administration group of compound 17-F. Meanwhile, the drug efficacy of the compound 17-F temporarily disappeared 5 days after the start of administration. However, 7 days after the start of administration, a raw value of the skin temperature and a changed temperature were confirmed to decrease again by the administration of compound 17-F in a manner dependent on its administration concentration. On the other hand, no inhibitory effect on skin temperatures was confirmed in an estradiol (E2) administration group serving as a positive control set this time on the basis of the previous report.

Figure 6:
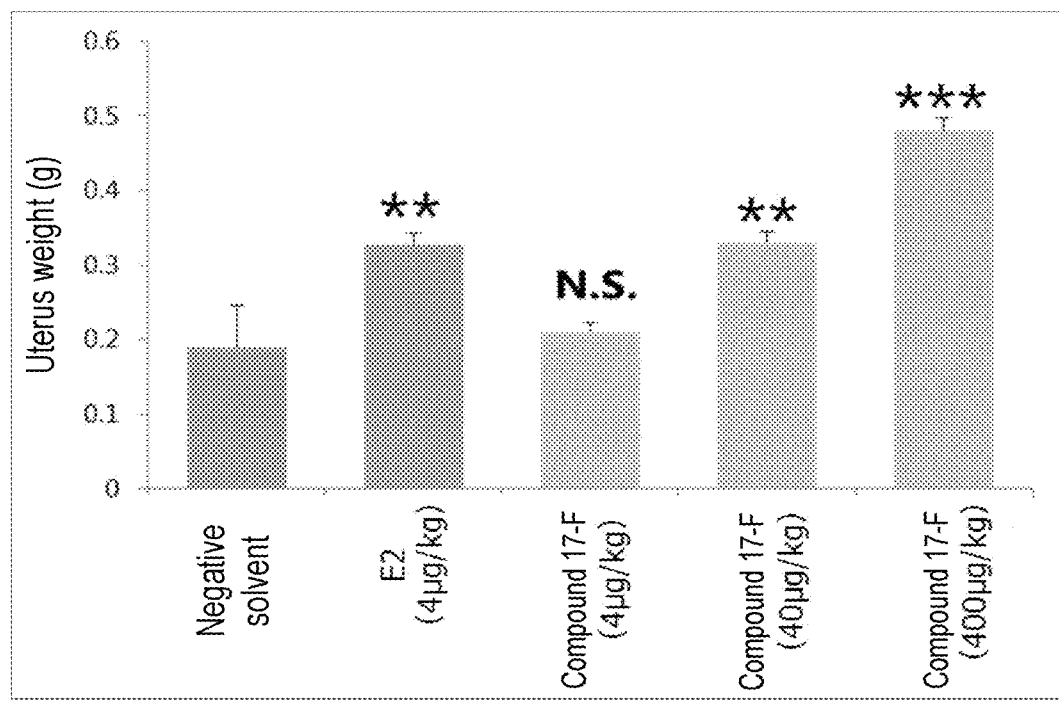
FIG. 6 shows the influence of the compound of the present invention on uterus weights.

2-2) Change in uterus weight After the completion of all procedures of measurement, the uterus was harvested by anatomy, and its wet weight was measured (FIG. 6). The uterus abundantly expresses ERα and on the other hand, rarely expresses ERP. The activation of ERα in the uterus reportedly has an effect of elevating its weight. The uterus weight was significantly increased in the E2 (estradiol) administration group as compared with the negative solvent administration group among OVX rats, whereas no change in uterus weight was confirmed in the group given compound 17-F (4 ig/kg) at the same dose as in E2. However, it was revealed that the uterus weight was elevated in a concentration-dependent manner as the dose of compound 17-F was increased. This demonstrated that a low-concentration region of compound 17-F is effective for inhibiting hot flash and on the other hand, does not influence uterus weights, i.e., does not activate ERα.

The invention claimed is:
1. A compound of formula (1):

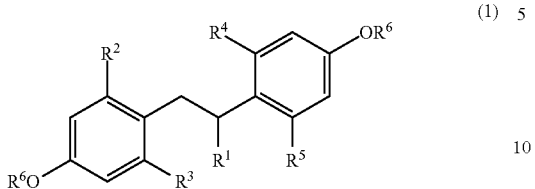

or a salt thereof,
wherein:
R¹ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, or a 1-trifluoromethyl-1-hydroxymethyl group;
R² to R⁵ are the same or different and each represent a hydrogen atom or a fluorine atom; and
R⁶ represents a hydrogen atom or an alkanoyl group having 2 to 5 carbon atoms.

2. A method for activating ERβ comprising administering to a subject in need thereof an effective amount of a compound of formula (1) or a salt thereof:

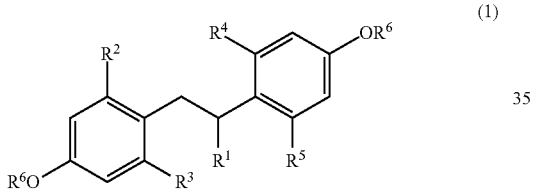

wherein:
R¹ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, or a 1-trifluoromethyl-1-hydroxymethyl group;
R² to R⁵ are the same or different and each represent a hydrogen atom or a fluorine atom; and
R⁶ represents a hydrogen atom or an alkanoyl group having 2 to 5 carbon atoms.

3. A method of preventing or ameliorating skin aging comprising administering to a subject in need thereof an effective amount of a compound of formula (1) or a salt thereof:

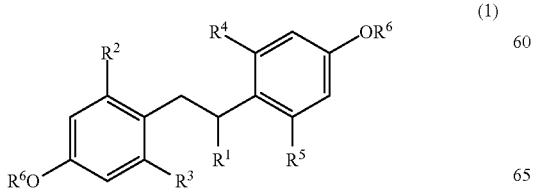

wherein:
R¹ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, a 1-trifluoromethyl-1-hydroxymethyl group, or a 1-methylpropyl group;
R² to R⁵ are the same or different and each represent a hydrogen atom or a fluorine atom; and
R⁶ represents a hydrogen atom or an alkanoyl group having 2 to 5 carbon atoms.

4. A method of inhibiting sebum secretion comprising administering to a subject in need thereof an effective amount of a compound of formula (1) or a salt thereof:

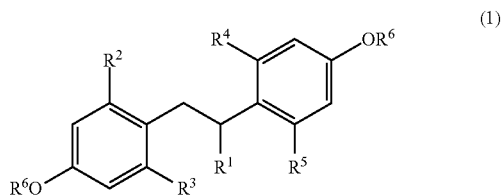

wherein:
R¹ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, a 1-trifluoromethyl-1-hydroxymethyl group, or a 1-methylpropyl group;
R² to R⁵ are the same or different and each represent a hydrogen atom or a fluorine atom; and
R⁶ represents a hydrogen atom or an alkanoyl group having 2 to 5 carbon atoms.

5. A method of ameliorating acne comprising administering to a subject in need thereof an effective amount of a compound of formula (1) or a salt thereof:

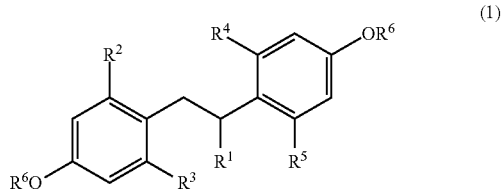

wherein:
R¹ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, a 1-trifluoromethyl-1-hydroxymethyl group, or a 1-methylpropyl group;
R² to R⁵ are the same or different and each represent a hydrogen atom or a fluorine atom; and
R⁶ represents a hydrogen atom or an alkanoyl group having 2 to 5 carbon atoms.

6. A method of ameliorating hot flash comprising administering to a subject in need thereof an effective amount of a compound of formula (1) or a salt thereof:

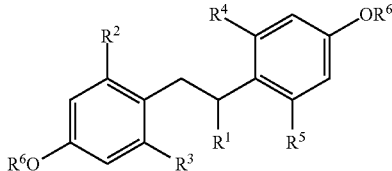

wherein:
$R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, a 1-trifluoromethyl-1-hydroxymethyl group, or a 1-methylpropyl group;
$R^2$ to $R^5$ are the same or different and each represent a hydrogen atom or a fluorine atom; and
$R^6$ represents a hydrogen atom or an alkanoyl group having 2 to 5 carbon atoms.

7. A method of ameliorating prostatic hyperplasia comprising administering to a subject in need thereof an effective amount of a compound of formula (1) or a salt thereof:

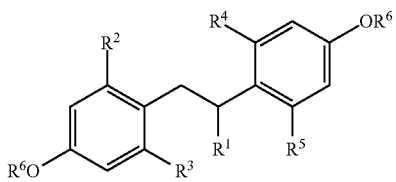

wherein:
$R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, a 1-trifluoromethyl-1-hydroxymethyl group, or a 1-methylpropyl group;
$R^2$ to $R^5$ are the same or different and each represent a hydrogen atom or a fluorine atom; and
$R^6$ represents a hydrogen atom or an alkanoyl group having 2 to 5 carbon atoms.

8. A method for inhibiting androgen activation comprising administering to a subject in need thereof an effective amount of a compound of formula (1) or a salt thereof:

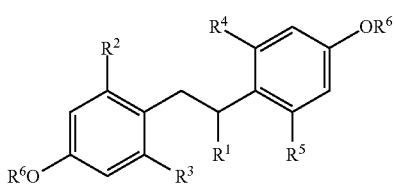

wherein:
$R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, a 1-trifluoromethyl-1-hydroxymethyl group, or a 1-methylpropyl group;
$R^2$ to $R^5$ are the same or different and each represent a hydrogen atom or a fluorine atom; and
$R^6$ represents a hydrogen atom or an alkanoyl group having 2 to 5 carbon atoms.

9. The method according to claim 3, wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, or a 1-trifluoromethyl-1-hydroxymethyl group.

10. The method according to claim 4, wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, or a 1-trifluoromethyl-1-hydroxymethyl group.

11. The method according to claim 5, wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, or a 1-trifluoromethyl-1-hydroxymethyl group.

12. The method according to claim 6, wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, or a 1-trifluoromethyl-1-hydroxymethyl group.

13. The method according to claim 7, wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, or a 1-trifluoromethyl-1-hydroxymethyl group.

14. The method according to claim 8, wherein $R^1$ represents a cycloalkyl group having 3 to 8 carbon atoms, an alkenyl group having 2 to 6 carbon atoms and optionally substituted with a halogen atom, a 5-membered nitrogen-containing heteroaryl group, a 4- to 6-membered cyclic amino group, an alkanoylamino group having 2 to 6 carbon atoms and optionally substituted with a halogen atom, or a 1-trifluoromethyl-1-hydroxymethyl group.

* * * * *